US008802128B2

(12) United States Patent
Robinson et al.

(10) Patent No.: US 8,802,128 B2
(45) Date of Patent: *Aug. 12, 2014

(54) STEROID-CONTAINING SUSTAINED RELEASE INTRAOCULAR IMPLANTS AND RELATED METHODS

(75) Inventors: Michael R. Robinson, Irvine, CA (US); Scott M. Whitcup, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 1390 days.

This patent is subject to a terminal disclaimer.

(21) Appl. No.: 11/491,353

(22) Filed: Jul. 21, 2006

(65) Prior Publication Data

US 2007/0298074 A1 Dec. 27, 2007

Related U.S. Application Data

(63) Continuation-in-part of application No. 11/473,947, filed on Jun. 23, 2006.

(51) Int. Cl.
*A61F 2/02* (2006.01)
*A61K 31/54* (2006.01)
*A61K 31/56* (2006.01)
*A61K 31/58* (2006.01)
*A61K 31/573* (2006.01)
*A61K 31/575* (2006.01)
*A61K 31/137* (2006.01)
*A61K 31/4164* (2006.01)
*A61K 31/4168* (2006.01)
*A61K 9/00* (2006.01)

(52) U.S. Cl.
CPC .............. *A61K 9/0051* (2013.01); *A61K 31/58* (2013.01)
USPC ........... 424/428; 514/171; 514/174; 514/176; 514/180; 514/227.2; 514/392; 514/396; 514/400; 514/401; 514/653

(58) Field of Classification Search
CPC ..... A61K 9/0051; A61K 31/54; A61K 31/56; A61K 31/58; A61K 31/573; A61K 31/575; A61K 31/4164; A61K 31/4168; A61K 31/137; A61F 2/02
USPC .................. 424/428; 514/171, 174, 176, 180, 514/227.2, 392, 396, 400, 401, 653
See application file for complete search history.

(56) References Cited

U.S. PATENT DOCUMENTS

| 3,416,530 | A | 12/1968 | Ness |
| 3,432,592 | A | 3/1969 | Speiser |
| 3,845,770 | A | 11/1974 | Theeuwes et al. ............ 128/260 |
| 3,914,402 | A | 10/1975 | Shell |
| 3,916,899 | A | 11/1975 | Theeuwes et al. ............ 128/260 |
| 3,921,632 | A | 11/1975 | Bardani |
| 3,961,628 | A | 6/1976 | Arnold |
| 3,986,510 | A | 10/1976 | Higuchi et al. |
| 4,008,864 | A | 2/1977 | Torphammar et al. . 242/107.4 R |
| 4,014,334 | A | 3/1977 | Theeuwes et al. |
| 4,063,064 | A | 12/1977 | Saunders et al. ........... 219/121 L |
| 4,088,864 | A | 5/1978 | Theeuwes et al. ...... 219/121 LM |
| 4,144,317 | A | 3/1979 | Higuchi et al. ................. 424/21 |
| 4,180,646 | A | 12/1979 | Choi et al. |
| 4,186,184 | A | 1/1980 | Zaffaroni |
| 4,200,098 | A | 4/1980 | Ayer et al. ..................... 128/260 |
| 4,201,210 | A | 5/1980 | Hughes et al. |
| 4,285,987 | A | 8/1981 | Ayer et al. ......................... 427/3 |
| 4,300,557 | A | 11/1981 | Refojo et al. |
| 4,304,765 | A | 12/1981 | Shell et al. ...................... 424/14 |
| 4,327,725 | A | 5/1982 | Cortese et al. ............... 128/260 |
| 4,402,979 | A | 9/1983 | Shen et al. |
| 4,451,254 | A | 5/1984 | Dinius et al. |
| 4,474,451 | A | 10/1984 | Mizokami .................... 354/418 |
| 4,478,818 | A | 10/1984 | Shell et al. |

(Continued)

FOREIGN PATENT DOCUMENTS

| CA | 1333770 | 10/1988 |
| CA | 2336703 | 1/2000 |

(Continued)

OTHER PUBLICATIONS

Robert R. Ruffolo, Jr. and James E. Waddell, "Receptor Interactions of Imidazolines. IX. Cirazoline is an Alpha-1 Adrenergic Agonist and an Alpha-2 Adrenergic Antagonist", The Journal of Pharmacology and Experimental Therapeutics, 1982, 222(1), 29-63.*
Tom R. Walters, "Development and Use of Brimonidine in Treating Acute and Chronic Elevations of Intraocular Pressure: A Review of Safety, Efficacy, Dose Response, and Dosing Studies", Survey of Ophthalmology, Nov. 1996, vol. 41, Supplement 1, S19-S26.*
U.S. Appl. No. 07/357,394, filed May 1989.
U.S. Appl. No. 10/820,563, filed Apr. 2004.
Aguilar, H.E., et al. "Vancomycin Levels After Intravitreal Injection," Retina, 1995; 15:428-432.
Ahmad, M., et al. "Ortho Ester Hydrolysis: Direct Evidence for a Three-Stage Reaction Mechanism," Journal of American Chemistry, 1979; 101(10):2669-2677.

(Continued)

Primary Examiner — John Pak
Assistant Examiner — Nathan W Schlientz
(74) Attorney, Agent, or Firm — Barbara C. Potts; Joel B. German; Debra D. Condino

(57) ABSTRACT

Biocompatible intraocular implant systems are formulated for discontinuous or intermittent release of therapeutic levels of a therapeutic agent (such as a steroid) to minimize development of side effects associated with continuous or long term use of such agent. The implant system may comprise one or more implant, and preferably, although not necessarily, also contains an auxiliary agent having an activity effective to lessen at least one side effect associated with said therapeutic agent compared to the use of an otherwise identical implant system lacking said auxiliary agent. The implants containing the therapeutic agent and auxiliary agent may be placed in an eye to treat one or more ocular conditions while reducing the ocular side effects otherwise accompanying the use of such therapeutic agent.

2 Claims, 35 Drawing Sheets

(56) References Cited

U.S. PATENT DOCUMENTS

| | | | |
|---|---|---|---|
| 4,494,274 A | 1/1985 | Thurlow | 16/110 A |
| 4,521,210 A | 6/1985 | Wong | 604/8 |
| 4,599,353 A | 7/1986 | Bito | 514/530 |
| 4,668,506 A | 5/1987 | Bawa | 424/429 |
| 4,756,911 A | 7/1988 | Drost et al. | |
| 4,801,460 A | 1/1989 | Goertz et al. | |
| 4,806,337 A | 2/1989 | Snipes et al. | |
| 4,853,224 A | 8/1989 | Wong | 424/427 |
| 4,863,457 A | 9/1989 | Lee | |
| 4,865,846 A | 9/1989 | Kaufman | |
| 4,945,089 A | 7/1990 | Clark | |
| 4,959,217 A | 9/1990 | Sanders et al. | 424/473 |
| 4,966,849 A | 10/1990 | Vallee et al. | |
| 4,997,652 A | 3/1991 | Wong | 424/428 |
| 5,004,601 A | 4/1991 | Snipes | |
| 5,004,614 A | 4/1991 | Staniforth | |
| 5,006,342 A | 4/1991 | Cleary et al. | |
| 5,019,400 A | 5/1991 | Gombotz | |
| 5,028,624 A | 7/1991 | Chan et al. | 514/530 |
| 5,034,413 A | 7/1991 | Chan et al. | 514/530 |
| 5,075,115 A | 12/1991 | Brine | |
| 5,082,655 A | 1/1992 | Snipes et al. | |
| 5,164,188 A | 11/1992 | Wong | 424/428 |
| 5,169,638 A | 12/1992 | Dennis et al. | |
| 5,268,178 A | 12/1993 | Calhoun et al. | |
| 5,314,419 A | 5/1994 | Pelling | |
| 5,322,691 A | 6/1994 | Darougar et al. | |
| 5,330,992 A | 7/1994 | Eissenstat et al. | |
| 5,356,629 A | 10/1994 | Sander et al. | |
| 5,378,475 A | 1/1995 | Smith et al. | |
| 5,384,333 A | 1/1995 | Davis et al. | |
| 5,385,887 A | 1/1995 | Yim et al. | |
| 5,443,505 A | 8/1995 | Wong et al. | 623/4 |
| 5,476,511 A | 12/1995 | Gwon et al. | |
| 5,501,856 A | 3/1996 | Ohtori et al. | 424/428 |
| 5,597,897 A | 1/1997 | Ron et al. | |
| 5,601,844 A | 2/1997 | Kagayama et al. | |
| 5,656,297 A | 8/1997 | Bernstein et al. | |
| 5,660,847 A | 8/1997 | Magruder et al. | |
| 5,660,851 A | 8/1997 | Domb | |
| 5,688,819 A | 11/1997 | Woodward et al. | 514/357 |
| 5,693,335 A | 12/1997 | Xia et al. | |
| 5,707,643 A | 1/1998 | Ogura | |
| 5,755,785 A | 5/1998 | Rowsey et al. | |
| 5,766,242 A | 6/1998 | Wong et al. | 623/4 |
| 5,773,019 A | 6/1998 | Ashton et al. | |
| 5,773,021 A | 6/1998 | Gurtler et al. | |
| 5,824,072 A | 10/1998 | Wong | 623/4 |
| 5,824,074 A | 10/1998 | Koch | 623/6 |
| 5,869,079 A | 2/1999 | Wong et al. | 424/426 |
| 5,882,682 A | 3/1999 | Rork et al. | 424/473 |
| 5,902,598 A | 5/1999 | Chen et al. | |
| 5,941,250 A | 8/1999 | Aramant et al. | |
| 5,962,027 A | 10/1999 | Hughes | |
| 5,972,369 A | 10/1999 | Roorda et al. | |
| 6,045,791 A | 4/2000 | Liu | |
| 6,046,187 A | 4/2000 | Berde et al. | |
| 6,051,576 A | 4/2000 | Ashton et al. | |
| 6,063,116 A | 5/2000 | Kelleher | |
| 6,074,661 A | 6/2000 | Olejnik et al. | 424/427 |
| 6,217,895 B1 | 4/2001 | Guo et al. | 424/427 |
| 6,217,911 B1 | 4/2001 | Vaugn et al. | |
| 6,280,771 B1 | 8/2001 | Monkhouse | |
| 6,309,669 B1 | 10/2001 | Setterstrom et al. | |
| 6,329,369 B1 | 12/2001 | Chow et al. | 514/230.5 |
| 6,331,313 B1 | 12/2001 | Wong et al. | 424/427 |
| 6,369,116 B1 | 4/2002 | Wong et al. | 514/913 |
| 6,403,649 B1 | 6/2002 | Woodward et al. | 514/646 |
| 6,497,729 B1 | 12/2002 | Moussy et al. | |
| 6,534,542 B2 | 3/2003 | Chow et al. | 514/546 |
| 6,537,568 B2 | 3/2003 | Olejnik et al. | |
| 6,545,182 B2 | 4/2003 | Chow et al. | 564/587 |
| 6,548,078 B2 | 4/2003 | Guo et al. | 424/423 |
| 6,699,493 B2 | 3/2004 | Wong | 424/428 |
| 6,713,081 B2 | 3/2004 | Robinson et al. | |
| 6,726,918 B1 | 4/2004 | Wong et al. | 424/422 |
| 6,841,684 B2 | 1/2005 | Chow et al. | 548/335.1 |
| 7,048,946 B1 | 5/2006 | Wong et al. | |
| 7,091,232 B2 | 8/2006 | Chow et al. | 514/386 |
| 8,119,154 B2 | 2/2012 | Nivaggioli et al. | |
| 8,147,865 B2 | 4/2012 | Blanda et al. | |
| 8,257,730 B2 | 9/2012 | Blanda et al. | |
| 8,263,110 B2 | 9/2012 | Nivaggioli et al. | |
| 8,298,570 B2 | 10/2012 | Nivaggioli et al. | |
| 2003/0092766 A1 | 5/2003 | Chow et al. | 514/546 |
| 2004/0019098 A1 | 1/2004 | Andrews et al. | |
| 2004/0132824 A1 | 7/2004 | Gil et al. | 514/570 |
| 2004/0137059 A1 | 7/2004 | Nivaggioli et al. | 424/428 |
| 2004/0151753 A1 | 8/2004 | Chen | |
| 2004/0170665 A1 | 9/2004 | Donovan | |
| 2004/0266776 A1 | 12/2004 | Gil et al. | 514/249 |
| 2005/0048099 A1 | 3/2005 | Shiah et al. | 424/423 |
| 2005/0058696 A1 | 3/2005 | Donello et al. | 424/449 |
| 2005/0059664 A1 | 3/2005 | Gil et al. | |
| 2005/0059721 A1 | 3/2005 | Chow et al. | 514/392 |
| 2005/0059744 A1 | 3/2005 | Donello et al. | 514/367 |
| 2005/0075366 A1 | 4/2005 | Heidelbaugh et al. | 514/314 |
| 2005/0101582 A1 | 5/2005 | Lyons et al. | 514/179 |
| 2005/0181017 A1 | 8/2005 | Hughes et al. | 424/427 |
| 2005/0232966 A1 | 10/2005 | Hughes et al. | |
| 2005/0244464 A1 | 11/2005 | Hughes et al. | 424/426 |
| 2005/0244468 A1 | 11/2005 | Nivaggioli et al. | |
| 2005/0244469 A1 | 11/2005 | Whitcup et al. | 424/400 |
| 2005/0244474 A1 | 11/2005 | Huang et al. | |
| 2006/0009498 A1 | 1/2006 | Whitcup | |
| 2006/0233859 A1 | 10/2006 | Whitcup et al. | |
| 2007/0031472 A1 | 2/2007 | Blanda et al. | |
| 2008/0131486 A1 | 6/2008 | Nivaggioli et al. | |
| 2008/0138382 A1 | 6/2008 | Nivaggioli et al. | |
| 2008/0145407 A1 | 6/2008 | Huang et al. | |
| 2012/0122821 A1 | 5/2012 | Blanda et al. | |

FOREIGN PATENT DOCUMENTS

| | | | |
|---|---|---|---|
| EP | 0 052 916 | 7/1981 | |
| EP | 0 102 265 | 3/1984 | |
| EP | 0 197 718 | 3/1986 | |
| EP | 0 251 680 A | 1/1988 | |
| EP | 251680 A2 * | 1/1988 | |
| EP | 0 322 319 | 6/1989 | |
| EP | 0 430 539 | 6/1991 | |
| EP | 0 474 098 | 3/1992 | |
| EP | 0 488 401 | 6/1992 | |
| EP | 0364417 | 2/1994 | A61K 31/557 |
| EP | 0 654 256 | 5/1995 | |
| EP | 0 311 065 | 10/1998 | |
| EP | 0 992 244 | 4/2000 | |
| WO | WO 87/07141 A1 * | 12/1987 | A61K 31/56 |
| WO | WO 91/15495 | 10/1991 | |
| WO | WO 91/18940 | 12/1991 | |
| WO | WO 92/21660 | 12/1992 | |
| WO | WO 93/10141 | 5/1993 | |
| WO | WO 94/03427 | 2/1994 | |
| WO | WO 94/10202 | 5/1994 | |
| WO | WO 94/14808 | 7/1994 | |
| WO | WO 94/18956 | 9/1994 | |
| WO | WO 95/13765 | 5/1995 | |
| WO | WO 96/38174 | 12/1996 | |
| WO | WO 97/26869 | 7/1997 | |
| WO | WO 98/22130 | 5/1998 | |
| WO | WO 99/11244 | 3/1999 | |
| WO | WO 00/02564 | 1/2000 | |
| WO | WO 00/37056 | 6/2000 | |
| WO | WO 00/56340 | 9/2000 | |
| WO | WO 00/62760 | 10/2000 | |
| WO | WO 01/30323 | 5/2001 | |
| WO | WO 02/02076 | 1/2002 | |
| WO | WO 02/43785 | 6/2002 | |
| WO | WO 03/094888 | 5/2003 | |
| WO | WO 2004/026106 | 4/2004 | |
| WO | WO 2004/062649 | 7/2004 | |
| WO | WO 2005/110362 | 4/2005 | |
| WO | WO 2005/107727 A | 11/2005 | |
| WO | WO 2005/110374 A | 11/2005 | |

(56) References Cited

FOREIGN PATENT DOCUMENTS

| WO | WO 2006/017347 A | 2/2006 |
|---|---|---|
| WO | WO2006-036280 | 4/2006 |
| WO | WO 2006/093758 | 9/2006 |
| WO | WO 2007/130945 | 11/2007 |
| WO | WO2008-019198 | 2/2008 |

OTHER PUBLICATIONS

Akduman, L., et al. "The early treatment diabetic retinopathy study," *Clinical trials in ophthalmology: a summary and practice guide*, Kertes, P.S., Conway, M.D., eds. Baltimore: Williams & Wilkins, 1998; 15-35.

Algvere, P.V., et al. "Transplantation of RPE in Age-Related Macular Degeneration: Observations in Disciform Lesions and Dry RPE Atrophy," *Graefe's Archives of Clinical Experimental Ophthalmology*, 1997; 235(3):149-158.

Anderson, L.C., et al. "An Injectable Substained Release Fertility Control System," *Contraception*, 1976; 13:375-384.

Antcliff, R., et al. "The pathogenesis of edema in diabetic maculopathy," *Seminars in Ophthalmology*, 1999; 14:223-232.

Apel, A., et al. "A Subconjunctival Degradable Implant for Cyclosporine Delivery in Corneal Transplant Therapy," *Current Eye Research*, 1995; 14(8):659-667.

Araie, M. and Maurice, D.M. "The Loss of Fluorescein, Fluorescein Glucuronide and Fluorescein Isothiocyanate Dextran From the Vitreous by the anterior and Retinal Pathways," *Experimental Eye Research*, 1991; 52:27-39.

Baker, R. "Monolithic Devices," *Controlled Release of Biologically Active Agents*, New York: John Wiley & Sons, 1987; 50-75.

Barnas, U., et al. "Parameters Associated with Chronic Renal Transplant Failure," *Nephrology Dialysis Transplantation*, 1997; 12(Suppl 2):82-85.

Barza, M., et al. "Pharmacokinetics of Intravitreal Carbenicillin, Cefazolin, and Gentamicin in Rhesus Monkeys," *Investigative Ophthalmology & Visual Science*, 1983; 24:1602-1606.

Beck, R.W., et al. "The Effect of Corticosteroids for Acute Optic Neuritis on the Subsequent Development of Multiple Sclerosis," *New England Journal of Medicine*, 1993; 329(24): 1764-1769.

Bennett, W.M. and Barry, J.M. "Failure of Dexamethasone to Provide Adequate Chronic Immunosuppression for Renal Transplantation," *Transplantation*, 1979; 27(3):218-219.

Ben-Nun, J., et al. "Pharmacokinetics of Intravitreal Injection," *Investigative Ophthalmology & Visual Science* 1989; 30(6):1055-1061.

Bigar, F. and C.P. Herbort. "Corneal Transplantation," *Current Opinion in Ophthalmology*, 1992; 3(4):473-481.

Bingaman, D.P., et al. "Inhibition of preretinal neovascularization in pigs by intravitreal triamcinolone acetonide," *Investigative Ophthalmology and Visual Science*, 1995; 36(4):S401, abstract 1867.

Bloch-Michel, E. "Opening Address: Intermediate Uveitis," *Developments in Ophthalmology: Intermediate Uveitis*, W.R.F. Böke, et al. eds. Basel: Karger, 1992; 23:1-2.

Bodor, N., et al. "A Comparison of Intraocular Pressure Elevating Activity of Loteprednol Etabonate and Dexamethasone in Rabbits," *Current Eye Research*, 1992; 11(6):525-530.

Böke, W.R.F. "Clinical Picture of Intermediate Uveitis," *Developments in Ophthalmology: Intermediate Uveitis*, W.R.F. Böke, et al. eds. Basel: Karger 1992; (23):20-27.

Bolen, J.B. "Nonreceptor tyrosine protein kinases," *Oncogene*, 1993; 8(8):2025-2031.

Budavari, S., et al. eds. *The Merck Index*, 12$^{th}$ ed. Rahway, NJ: Merck and Co., 1996; Table of Contents only.

Bundgaard, H. and Møss, J. "Prodrugs of Peptides IV: Bioreversible Derivatization of the Pyroglutamyl Group by N-Acylation and N-Aminomethylation to Effect Protection against Pyroglutamyl Aminopeptidease," *Journal of Pharmaceutical Sciences*, 1989; 78(2):122-126.

Burdon, M.A. and P. McDonnell. "A Survey of Corneal Graft Practice in the United Kingdom," *Eye*, 1995; 9(Suppl):6-12.

Chacko, D.M., et al. "Survival and Differentiation of Cultured Retinal Progenitors Transplanted in the Subretinal Space of the Rat," *Biochemical and Biophysical Research Communications*, 2000; 268(3):842-846.

Challa, J.K., et al. "Exudative Macular Degeneration and Intravitreal Triamcinolone: 18 month follow up," *Australian and New Zealand Journal of Ophthalmology*, 1998; 26:277-281.

Chang, David, et al. "Phase II results of an intraocular steroid delivery system for cataract surgery," *Ophthalmology*, Jun. 1996; 106(6):1172-1177.

Chang, M., et al. "Basic Science and Clinical Aspects of Wound Healing in Glaucoma Filtering Surgery," *Journal of Ocular Pharmacology and Therapeutics*, 1998; 14(1):75-95.

Charles, J., et al. "Use of Bioerodible Polymers Impregnated with Mitomycin in Glaucoma Filtration Surgery in Rabbits," *Ophthalmology*, Apr. 1991; 98(4):503-508.

Cheng, Cheng-Kuo, et al. "Intravitreal Sustained-Release Dexamethasone Device in the Treatment of Experimental Uveitis," *Investigative Ophthalmology & Visual Science*, Feb. 1995; 36(2):442-453.

Clarkson, J.G. "Central retinal vein occlusion," *Retina*, 3$^{rd}$ ed. Ryan, S., Schachat, A.P., eds. St. Louis, MO: CV Mosby; 2001; 1368-1375.

Cuff, G. and Raouf, F. "A Preliminary Evaluation of Injection Molding as a Technology to Produce Tablets," *Pharmaceutical Technology*, 1998; 96-106.

Davis, P.A., et al. "Intraocular Implant for Controlled 5-Fluorouracil Release," *Proceedings of the 19th International Symposium of Controlled Release Bioactive Materials*, 1992; 19:339-340.

De Jong, S.J., et al. "New insights into the hydrolytic degradation of poly(lactic acid): participation of the alcohol terminus," *Polymer*, 2001; 42:2795-2802.

Di Colo, G. "Controlled Drug Release From Implantable Matrices Based On Hydrophobic Polymers," *Biomaterials*, 1992; 13(12):850-856.

Dick, J., et al. "Macular edema," *Retina*, 3$^{rd}$ ed. Ryan, S., Schachat, A.P., eds. St. Louis, MO: CV Mosby; 2001; 967-979.

Dinning, W.J. "Intermediate Uveitis: history, terminology definition pars planitis: systemic disease associations," *Developments in Ophthalmology: Intermediate Uveitis*, W.R.F. Böke, et al. eds. Basel: Karger, 1992; 3-8.

Dohlman, C., et al. "Treatment of corneal edema with a buried implant," *Transactions: American Academy of Ophthalmology and Otolaryngology*, Mar.-Apr. 1966; 267-280.

Enyedi, Laura, et al. "An Intravitreal Device Providing Sustained Release of Cyclosporine and Dexamethasone," *Current Eye Research*, 1996; 15(5):549-557.

Enzmann, V., et al. "Immunological Problems of Transplantation into the Subretinal Space," *Acta Anatomica*, 1998; 162(2-3):178-183.

Fatt, I. "Flow and Diffusion In the Vitreous Body of The Eye," *Bulletin of Mathematical Biology*, 1975; 37:85-90.

Fekrat, S. and Finkelstein, D. "The Central Vein Occlusion Study," *Clinical trials in ophthalmology: a summary and practice guide*, Kertes, P.S., Conway, M.D., eds. Baltimore, MD: Williams & Wilkins, 1998; 129-143.

Frank, R.N. "Etiologic mechanisms in diabetic retinopathy," *Retina*, 3$^{rd}$ ed. Ryan, S., Schachat,, A.P., eds. St. Louis, MO: CV Mosby; 2001; 1259-1294.

Friedrich, S., et al. "Finite Element Modeling of Drug Distribution in the Vitreous Humor of the Rabbit Eye," *Annals of Biomedical Engineering*, 1997; 25:303-314.

Gennaro, A.R. ed. *Remington: The Science and Practice of Pharmacy*, 19$^{th}$ Ed. Easton, PA: Mack Publishing Company, 1995; Table of Contents only, xv-xvi.

Gillies, M.C., et al. "Safety of an intravitreal injection of triamcinolone," *Archives of Ophthalmology*, Mar. 2004; 122:336-340.

Gilman, A.G., et al. eds. *Goodman and Gilman's: The Pharmacological Basis of Therapeutics*. 8$^{th}$ Ed. New York: Pergamon Press, 1990; Table of Contents only, xi-xvi.

Gould, L., et al. "Fifty:fifty Poly (DL Glycolic Acid-Lactic Acid) Copolymer as a Drug Delivery System for 5-Fluorouracil: A Histopathological Evaluation," *Canadian Journal of Ophthalmology*, 1994; 29(4):168-171.

(56) References Cited

OTHER PUBLICATIONS

Greenfield, R.S., et al. "Evaluation in Vitro of Adriamycin Immunoconjugates Synthesized Using an Acid-sensitive Hydrazone Linker," *Cancer Research*, 1990; 50:6600-6607.

Guan, D., et al. "The Therapeutic Window of Cyclosporine in Chinese Recipients of Renal Transplantation," *Transplantation Proceedings*, 1995; 27(1):850-851.

Hainsworth, Dean P., et al. "Sustained Release Intravitreal Dexamethasone," *Journal of Ocular Pharmacology and Therapeutics*, 1996; 12(1):57-63.

Hari, P. and Srivastava, R.N. "Pulse Corticosteroid Therapy with Methylprednisolone or Dexamethasone," *Indian Journal of Pediatrics*, 1998; 65(3):557-560.

Haynes, Robert C. Jr. "Adrenocorticotropic Hormone; Adrenocortical Steroids and their Synthetic Analogs; Inhibitors of the Synthesis and Actions of Adrenocortical Hormones," *Goodman and Gilman's: The pharmacological Basis of Therapeutics*, 8th Ed. New York: Pergamon Press, 1990; 1431-1462.

Hayreh, S.S. "Posterior Drainage of the Intraocular Fluid From the Vitreous," *Experimental Eye Research*, 1996; 5:123-144.

Heller, J. "Bioerodible Hydrogels," *Hydrogels in Medicine and Pharmacy, vol. 3: Properties and Applications*, Peppas, N. A. ed. Boca Raton: CRC Press, 1987; 138-149.

Hirano, T. "Clinical Significance of Glucocorticoid Pharmacodynamics Assessed by Antilymphocyte Action in Kidney Transplantation," *Transplantation*, 1994; 57(9):1341-1348.

Höckel, M., et al. "Prevention of Peritoneal Adhesions in the Rat With Sustained Intraperitoneal Dexamethasone Delivered by a Novel Therapeutic System," *Annales Chirurgiae et Gynaecologiae*, 1987; 76(6):306-313.

Jackanicz, T., et al. "Polyactic Acid As a Biogradable Carrier for Contraceptive Steroids" *Contraception*, 1973; 8(3):227-234.

Jaffe, G.J., et al. "Safety, Efficacy, and Pharmacokinetics of an Intravitreal Fluocinolone Sustained Drug Delivered System," *Investigative Ophthalmology & Visual Science*, 1999; 40(4):S988, abstract 5195.

Jampel, H., et al. "Glaucoma Filtration Surgery in Monkeys Using 5-Fluorouridine in Polyanhydride Disks," *Archives of Ophthalmology*, Mar. 1990; 108(3):430-435.

Jay, W.M., et al. "Intravitreal Ceftazidime in a Rabbit Model: Dose- and Time-Dependent Toxicity and Pharmacokinetic Analysis," *Journal of Ocular Pharmacology*, 1987; 3(3):257-262.

Jellinek, D., et al. "Inhibition of Receptor binding by High-affinity RNA Ligands to Vascular Endothelial Growth Factor," *Biochemistry*, 1994; 33:10450-56.

Jennings, T., et al. "Posterior sub-Tenon's injections of corticosteroids in uveitis patients with cystoid macular edema," *Japanese Journal of Ophthalmology*, 1988; 32(4):385-391.

Johnson, F. and Maurice, D. "A Simple Method of Measuring Aqueous Humor Flow With Intravitreal Fluoresceinated Dextrans," *Experimental Eye Research*, 1984; 39:791-805.

Jonas, J.B., et al. "Intraocular pressure after intravitreal injection of triamcinolone acetonide," *British Journal of Ophthalmology*, 2003; 87:24-27.

Kane, A., et al. "Intravitreal Injection of Gentamicin in Rabbits," *Investigative Ophthalmology & Visual Science*, 1981; 20(5):593-597.

Kendall, R.L and K.A. Thomas. "Inhibition of vascular endothelial cell growth factor activity by an endogenously encoded soluble receptor," *Proceedings of the National Academy of Science USA*, 1994; 90:10705-09.

Kher, V., et al. "Low-Dose Dexamethasone—An Alternative Therapy for Acute Renal Allograft Rejection," *Transplantation Proceedings*, 1992; 24(5):1725.

Kim, K.J., et al. "Inhibition of vascular endothelial growth factor-induced angiogenesis suppresses tumour growth in vivo," *Nature*, 1993; 362(6423):841-844.

Kimura, H. and Ogura, Y. "Biodegradable Polymers for Ocular Drug Delivery," *Ophthalmologica*, 2001; 215:143-155.

Kinsella, J.L., et al. "Protein Kinase C Regulates Endothelial Cell Tube Formation on Basement Membrane Matrix, Matrigel," *Experimental Cell Research*, 1992; 199:56-62.

Kochinke, F. and Wong, V.G. "Biogradable Drug Delivery System for Uveitis Treatment, Oculex Pharmaceuticals, Inc.," Slide Presentation, 1996; total pp. 20.

Kochinke, F., et al. "Biodegradable Drug Delivery System for Uveitis Treatment," *Investigative Ophthalmology & Visual Science*, Feb. 1996; 37(3):S42.

Kralinger, M.T., et al. "Slow Release of Acetysalicyclic Acid by Intravitreal Silicone Oil," *Retina: The Journal of Retinal and Vitreous Diseases*, 2001; 21(5):513-520.

Kunou, Noriyuki, et al. "Biodegradable scleral implant for controlled intraocular delivery of betamethasone phosphate," *Journal of Biomedical Materials Research*, 2000; 51(4):635-641.

Kwak, H.W. and D'Amico, D.J. "Evaluation of the Retinal Toxicity and Pharmacokinetics of Dexamethasone After Intravitreal Injection," *Archives of Ophthalmology*, 1992; 110:259-266.

Laurent, U.B.G. and Fraser, J.R.E. "Turnover of Hyaluronate in the Aqueous Humor And Vitreous Body of the Rabbit," *Experimental Eye Research*, 1983; 36:493-504.

Lee, D., et al. "Complications of Subconjunctival 5-Fluorouracil Following Glaucoma Filtering Surgery," *Ophthalmic Surgery*, Mar. 1987; 18(3):187-190.

Lee, D., et al. "Glaucoma Filtration Surgery in Rabbits Using Bioerodible Polymers and 5-Fluorouracil," *Ophthalmology*, Dec. 1987; 94(12):1523-1530.

Lee, D., et al. "The Use of Bioerodible Polymers and 5-Fluorouracil in Glaucoma Filtration Surgery," *Investigative Ophthalmology & Visual Science*, Nov. 1988; 29(11):1692-1697.

Lee, K.Y. and Wong, V.G. "Dexamethasone Posterior Segment Drug Delivery System for Treatment of Severe Uveitis," *American Uveitis Society*, 1999; Abstract.

Lee, V.H.L., et al. "Drug Delivery to the Posterior Segment" *Retina*, $3^{rd}$ ed. T.E. Ogden and A.P. Schachat eds. St. Louis: CV Mosby, 1989; 483-498.

Leopold, I.H. "Nonsteroidal and steroidal anti-inflammatory agents," *Surgical pharmacology of the Eye*, Sears, M., Tarkkanen, A., eds. New York: Raven Press, 1985; 83-133.

Marcon, I. "A double-masked comparison of betaxolol and levobunolol for the treatment of primary open-angle glaucoma," *Arquivos Brasileiros de Oftalmologia*, 1990; 53(1):27-32.

Mariani, M., et al. "Inhibition of angiogenesis by FCE 26806, a potent tyrosine kinase inhibitor," *Proceedings of the American Association for Cancer Research*, 1994; 35:381, abstract 2268.

Maurice, D.M. "The Exchange of Sodium Between The Vitreous Body and The Blood And Aqueous Humour," *Journal of Physiology*, 1957; 137:110-125.

Maurice, D.M. "Flow of Water Between Aqueous and Vitreous Compartments in the Rabbit Eye," *American Journal of Physiology*, 1987; 252 (1):F104-F108.

Maurice, D.M. "Micropharmaceutics of the Eye," *Ocular Inflammation and Therapeutics*, 1983; 1:97-102.

Maurice, D.M. and Mishima, S. "Ocular Pharmacokinetics," *Pharmacology of the Eye*, M.L. Sears ed. New York: Springer-Verlag, 1984; 19-116.

Meadows, D.L., et al. "Ocular Drug Delivery with Subconjunctival Implants," *Proceedings of the International Symposium on Controlled Release of Bioactive Materials*, Controlled Release Society, Inc., 1994; 21:593-594.

Miller, R., et al. "Degradation Rates of Oral Resorbable Implants (Polylactates and Polyglycolates): Rate Modification with Changes in PLA/PGA Copolymer Ratios," *Journal of Biomedical Materials Research*, 1977; 11(5):711-719.

Mittal, R., et al. "Treatment of Acute Rejection in Live Related Renal Allograft Recipients: A Comparison of Three Different Protocols," *Nephron*, 1977; 77(2):186-189.

Molfino, F., et al. "IOP-lowering effect of dorzolamide 2% versus brimonidine tartrate 0.2%. A prospective randomized cross over study," *Investigative Ophthalmology & Visual Science*, Mar. 1998; 39(4):S481.

(56) References Cited

OTHER PUBLICATIONS

Morita Y., et al. "Intravitreous delivery of dexamethasone sodium *m*-sulfobenzoate from poly (DL-lactic acid) implants," *Biological & Pharmaceutical Bulletin*, Feb. 1998; 21(2):188-90.

Morita, Y., et al. "Polymer Blend Implant for Ocular Delivery of Fluorometholone," *Biological & Pharmaceutical Bulletin*, 1998; 21(1):72-75.

Moseley, H., et al. "Routes of Clearance of Radioactive Water From The Rabbit Vitreous," *British Journal of Ophthalmology*, 1984; 68:145-151.

Nakamura, O., et al. "Inhibition of neovascularization and tumor growth by dexamethasone," *No To Shinkei (Brain and Nerve)*, Jan. 1992; 44(1):37-41.

Nauck, M., et al. "Corticosteroids inhibit the expression of the vascular endothelial growth factor gene in human vascular smooth muscle cells," *European Journal of Pharmacology*, 1998; 341:309-315.

Nauck, M., et al. "Induction of vascular endothelial growth factor by platelet-activating factor and platelet-derived growth factor is downregulated by corticosteroids," *American Journal of Respiratory Cell and Molecular Biology*, 1997; 16:398-406.

Ogden, T.E., et al. eds. *Retina—Basic Science and Inherited Retinal Disease vol. 1*, St. Louis: CV Mosby, 1994; Table of Contents, xxiii-xxix.

Ohtori, A. and Tojo, K. "In vivo/in Vitro Correlation of Intravitreal Delivery of Drugs With the Help of Computer Simulation," *Biological & Pharmaceutical Bulletin*, 1994; 17(2):283-290.

Olsen, T.W., et al. "Human Scleral Permeability: Effects of Age, Cryotherapy, Transscleral Diode Laser, and Surgical Thinning," *Investigative Ophthalmology & Visual Science*, 1995; 36(9):1893-1903.

Oplinger, N. L., et al. "A Comparison of Corneal Autografts With Homografts," *Ophthalmic Surgery and Lasers*, 1998; 29(4):305-308.

Orth, D. "The branch vein occlusion study," *Clinical trials in ophthalmology: A summary and practice guide*, Kertes, P, and Conway, M, eds., Baltimore, MD: Williams & Wilkins, 1998: 113-127.

Park, T.G., et al. "A new preparation method for protein loaded poly (D,L-lactic-co-glycolic acid) microspheres and protein release mechanism study," *Journal of Controlled Release*, 1998; 55: 181-191.

Patel, N. P., et al. "Indications for and Outcomes of Repeat Penetrating Keratoplasty, 1989-1995," *Ophthalmology*, 2000; 107(4):719-724.

Pearson, P.A., et al. "Clearance and Distribution of Ciprofloxacin After Intravitreal Injection," *Retina*, 1993; 13:326-330.

Pe'er, J., et al. "Vascular endothelial growth factor by platelet-activating factor upregulation in human central retinal vein occlusion," *Ophthalmology*, 1998; 105:412-416.

Peyman, G.A. and Herbst, R. "Bacterial endophthalmitis," *Archives of Ophthalmology*, 1974; 91(5):416-418.

Peyman, G.A., et al. "A Technique for Retinal Pigment Epithelium Transplantation for Age-Related Macular Degeneration Secondary to Extensive Subfoveal Scarring," *Ophthalmic Surgery*, 1991; 22(2):102-108.

Pinar, V. "Intermediate Uveitis," *Massachusetts Eye & Ear Infirmary Immunology Service*, Boston.

Plowman, G.D., et al. "Receptor Tyrosine Kinases as Targets for Drug Intervention," *Drug News & Perspectives*, 1994; 7(6): 334-339.

Rao, K.V., et al. "Successful Renal Transplantation in a Patient With Anaphylactic Reaction to Solu-Medrol (Methylprednisolone Sodium Succinate)," *American Journal of Medicine*, 1982; 72(1):161-163.

Rao, N.A., et al. "Intraocular Inflammation and Uveitis," *Basic and Clinical Science Course*, Section 9, San Francisco: American Academy of Ophthalmology, 1998-1999; 57-80, 102-103, 152-156.

Renfro, L. and Snow, J.S. "Ocular Effects of Topical and Systemic Steroids," *Dermatologic Clinics*, 1992; 10:505-512.

Riordan-Eva, P., et al. "Orbital floor steroid injections in the treatment of uveitis," *Eye*, 1994; 8(1):66-69.

Robin, Jeffrey B., et al. "The Histopathology of Corneal Neovascularization," *Archives of Ophthalmology*, 1985; 103(2):284-287.

Roff, W.J. and Scott, J.R. eds. *Handbook of Common Polymers*, Cleveland: CRC Press, 1971; Table of Contents.

Rootman, D.S., et al. "Toxicity and Pharmacokinetics of Intravitreally Injection Ciprofloxacin in Rabbit Eyes," *Canadian Journal of Ophthalmology*, 1992; 27(6):277-282.

Sasaki, H., et al. "Drug Absorption Behavior After Periocular Injections," *Biological & Pharmaceutical Bulletin*, 1999; 22(9):956-960.

Schindler, R.H., et al. "The Clearance of Intravitreal Triamcinolone Acetonide," *American Journal of Ophthalmology*, 1982; 93(4):415-417.

Scholes, G.N., et al. "Clearance of Triamcinolone From Vitreous," *Archives of Ophthalmology*, 1985; 103(10):1567-1569.

Schwartz, B. "The Response of Ocular Pressure to Corticosteroids," *International Ophthalmology Clinics*, 1966; 6:929-989.

Shields, Bruce M. "Glaucoma Filtering Procedures," *A Study Guide for Glaucoma*, Baltimore: Williams & Wilkins, 1982; 453-476.

Skalka, H.W. and Prchal, J.T. "Effect of Corticosteroids on Cataract Formation," *Archives of Ophthalmology*, 1980; 98(10):1773-1777.

Smith, T., et al. "Sustained-release subconjunctival 5-Fluorouracil," *Ophthalmic Surgery and Lasers*, Sep. 1996; 27(9):763-767.

Stewart, W., et al. "Washout periods for brimonidine 0.2% and latanoprost 0.005%," *American Journal of Ophthalmology*, Jun. 2001; 131(6):798-799.

Taba, K.E., et al. "Intravitreal sustained release fluocinolone implant inhibits experimental choroidal neovascularization," *Investigative Ophthalmology & Visual Science*, Mar. 1999; 40(4):S172, abstract 920.

Takano, S.,et al. "Inhibition of Angiogenesis by a Novel Diaminoanthraquinone that Inhibits Protein Kinase C," *Molecular Biology of the Cell*, 1993; 4:358A, abstract 2076.

Tan, D.T.H., et al. "Randomized Clinical Trial of a New Dexamethasone Delivery System (Surodex) for Treating of Post-Cataract Surgery Inflammation," *Ophthalmology*, 1999; 106(2):223-231.

Tennant, J.L. "Cystoid maculopathy," *Current concepts in cataract surgery: selected proceedings of the fifth biennial cataract surgical congress*, Emery, J.M. ed. St. Louis: CV Mosby, 1978; 360-362.

Theng, J.T.S., et al. "Pharmacokinetic and Toxicity Study of an Intraocular Cyclosporine DDS in the Anterior Segment of Rabbit Eyes," *Investigative Ophthalmology & Visual Science*, Nov. 2003; 44(11):4895-4899.

Tracy, M.A., et al. "Factors affecting the degradation rate of poly(lactide-co-glycolide) microspheres in vivo and in vitro," *Biomaterials*, 1999; 20:1057-1062.

Tsubota, K. "Ocular Surface Management in Corneal Transplantation, A Review," *Japanese Journal of Ophthalmology*, 1999; 43(6):502-508.

*The United States Pharmacopeia, The National Formulary*, "USP 24/NF 19," 2000; 1941-1951.

Weisbecker, C.A., et al., eds. *Physicians' Desk Reference for Ophthalmology 27th ed.*, Montvale, NJ: Medical Economics Company, 1998; 7-8, 278-279.

Wingate, R.J., et al. "Intravitreal Triamcinolone and Elevated Intraocular Pressure," *Australian and New Zealand Journal of Ophthalmology*, Dec. 1999; 27(6):431-2.

Wright, P.S., et al. "Inhibition of Angiogenesis In Vitro and In Ovo with an Inhibitor of Cellular Protein Kinases, MDL 27032," *Journal of Cellular Physiology*, 1992; 152(3):448-457.

Xu, J., et al. "Permeability and Diffusion in Vitreous Humor: Implications for Drug Delivery," *Pharmaceutical Research*, 2000; 17(6):664-669.

Zhou, T., et al. "Development of a Multiple-Drug Delivery Implant for Introcular Management of Proliferative Vitreoretinopathy," *Journal of Controlled Release*, 1998; 55:281-295.

U.S. Appl. No. 60/587,092, filed Jul. 12, 2004, Whitcup.
U.S. Appl. No. 07/386,835, filed Jul. 27, 1989, Chan et al.
U.S. Appl. No. 11/303,462, filed Dec. 15, 2005, Hughe et al.
U.S. Appl. No. 11/473,947, filed Jun. 23, 2006, Whitcup et al.
Ahmad, M. et al., J. Amer. Chem. Soc. 101, 2669 (1979).

(56) References Cited

OTHER PUBLICATIONS

Andreau, K., et al., *Induction of apoptosis by dexamethasone in the B cell lineage*, Immunopharmacology Jul. 1998:40(1):67-76.

Beck, R.W., et al., A randomized, controlled trial of corticosteroids in the treatment of acute optic neuritis. The Optic Neuritis Study Group, *N. Engl J Med.* Feb. 27, 1992;326(9):634-5.

Bito, L. Z., Applied Pharmacology in the Medical Treatment of Glaucomas, Drance, S. M. and Neufeld, A. H. eds., New York, Grune & Stratton, 1984, pp. 477-505.

Bito, L. Z., Arch. Ophthalmol. 105, 1036 (1987).

Bito, L. Z., Biological Protection With Prostaglandins Cohen, M. M., ed., Boca Raton, Fla., CRC Press Inc., 1985, pp. 231-252.

Brubaker, Mechanism of Action of Bimatoprost (Lumigan™), Surv Ophthalmol 45 (Suppl 4):S347-S351 (2001).

Chen, et al., Lumigan®: A Novel Drug for Glaucoma Therapy, Optom In Pract, 3:95-102 (2002).

Coleman, et al., A 3-Month Randomized Controlled Trial of Bimatoprost (LUMIGAN) versus Combined Timolol and Dorzolamide (Cosopt) in Patients with Glaucoma or Ocular Hypertension, Ophthalmology 110(12): 2362-8 (2003).

Druilhe, A., et al., *Glucocorticoid-induced apoptosis in human eosinophils: mechanisms of action*, Apoptosis Oct. 2003;8(5):481-95.

Encyclopedia of Polymer Science and Technology, vol. 3, published by Interscience Publishers, Inc., New York, latest edition.

Goldberg, Ivan, in *Aust. Preser. 25*, 142 (2002).

Goodman & Gilman's The Pharmacological Basis of Therapeutics, ninth edition, McGraw Hill (1996).

Heller, Biodegradable Polymers in Controlled Drug Delivery, In: CRC Critical Reviews in Therapeutic Drug Carrier Systems, vol. 1, CRC Press, Boca Raton, FL 1987, pp. 39-90.

Heller, J. et al., Methods in Enzymology 112, 422-436 (1985).

Heller, J., J. Adv. Polymer Sci. 107, 41 (1993).

Inoue, M.; et al., *Vitreous Concentrations Of Triamcinolone Acetonide In Human Eyes After Intravitreal Or Subtenon Injection.* Am. J. Ophthalmol. 2004;138:1046-8.

Jaffe GJ, et al., *Safety And Pharmacokinetics Of An Intraocular Fluocinolone Acetonide Sustained Delivery Device*, Invest. Ophthalmol. Vis. Sci. 2000;41:3569-75.

Jeong, J. H. et al, Bioconj. Chem. 14, 473 (2003).

Kang SW et al., Macular grid photocoagulation after intravitreal triamcinolone acetonide for diffuse diabetic macular edema, *Arch Ophthalmol.* May 2006;124(5):653-8.

Mathebula, S. D. in *The South African Optometrist,* Sep. 2005, pp. 89-95.

Migita, K., et al., *Apoptosis Induction In Human Peripheral Blood T Lymphocytes By High-Dose Steroid Therapy.* Transplantation 1997;63:583-7.

Nilsson et al., Invest. Ophthalmol. Vis. Sci. 28(suppl), 284 (1987).

Rahil, J. et al, J. Am. Chem. Soc. 103, 1723 (1981).

Schimmer B.P. and Parker K.L. ACTH: *Adrenocortical Steroids and their Synthetic Analogs,* 10$^{th}$ ed. in The Pharmacological Basis of Therapeutics 1657 (Hardman J.G. and Limbard L.L., editors, McGraw-Hill, 2001).

Scott, J. R. and W. J. Roff, Handbook of Common Polymers, Section 64, (1971) published by CRC Press, Cleveland, Ohio.

Siebold et al., Prodrug 5, 3 (1989).

Starr, M. S., Exp. Eye Res. 1971, 11, pp. 170-177.

Turcotte, J.G., et al., *Rejection Crises In Human Renal Transplant Recipients: Control With High Dose Methylprednisolone Therapy,* Arch. Surg. 1972;105:230-6.

USP 23; NF 18 (1995) pp. 1790-1798.

Watson et al., Ophthalmology 103:126 (1996).

Woodward et al., AGN 2024 (Lumigan®): A Synthetic Prostamide Analog that Lowers Primate Intraocular Pressure by Virtue of Its Inherent Pharmacological Activity, ARVO 2002.

Woodward et al., The Pharmacology of Bimatoprost (LumiganTM), Surv Ophthalmol 45 (Suppl 4) S337-S345 (2001).

U.S. Appl. No. 10/837,356, filed Apr. 30, 2004.
U.S. Appl. No. 11/118,288, filed Apr. 29, 2005.
U.S. Appl. No. 11/474,149, filed Jun. 23, 2006.
U.S. Appl. No. 11/932,373, filed Oct. 31, 2007.
U.S. Appl. No. 12/031,656, filed Feb. 14, 2008.
U.S. Appl. No. 12/031,659, filed Feb. 14, 2008.
U.S. Appl. No. 13/356,934, filed Jan. 24, 2012.
U.S. Appl. No. 13/613,636, filed Sep. 13, 2012.

\* cited by examiner

STEROID-CONTAINING SUSTAINED RELEASE INTRAOCULAR IMPLANTS AND RELATED METHODS

CROSS REFERENCE

This application is a continuation in part of U.S. patent application Ser. No. 11/473,947 filed Jun. 23, 2006, which prior application is incorporated herein by reference in its entirely.

BACKGROUND

The present invention generally relates to devices and methods to treat an eye of a patient, and more specifically to intraocular implants that provide extended release of a therapeutic agent to an eye in which the implant is placed.

Steroids, such as the corticosteroid, fluocinolone acetonide (1,4-pregnadien-6α, 9α-difluoro-11β, 16 α, 17, 21-tetrol-3, 20-dione 16, 17-acetonide), are usually given topically, systemically, or periocularly, as an injection, to treat uveitis. All three methods of delivery have drawbacks, e.g., topical corticosteroids do not treat diseases in the back on the eye, systemic corticosteroids are often associated with many unwanted side effects, and periocular injections may sometimes cause globe perforation, periocular fibrosis and ptosis.

An alternative that may circumvent the drawbacks of the above-mentioned delivery methods is to use sustained-released drug delivery systems. In 2000, Jaffe et al. reported using compressed pure fluocinolone acetonide pellets coated with silicone and polyvinyl alcohol as a fluocinolone sustained delivery device (Jaffe, G. J. et al., Journal of Ophthalmology and Vision Surgery, Vol 41, No. 11, October 2000). They obtained release rates of 1.9±0.25 μg/day (6 months) and 2.2±0.6 μg/day (45 days) for the 2-mg device and 15-mg device, respectively. The duration of release for the 2-mg and 15-mg device was estimated to be 2.7 and 18.6 years, respectively. U.S. Pat. Nos. 6,217,895 and 6,548,078 disclose sustained release implants for delivering a corticosteroid, such as fluocinolone acetonide, to an eye. However, fluocinolone acetonide intravitreal implants made by Control Delivery Systems (the assignee of U.S. Pat. Nos. 6,217,895 and 6,548,078) were only partially successful and led to the development of cataracts and increased intraocular pressure.

In addition, intravitreal injection of triamcinolone acetonide (KENALOG®) for treatments of non-infectious uveitis, and macular edema due to various retinal diseases has appeared to be safe and effective.

Additional biocompatible implants for placement in the eye have been disclosed in a number of patents, such as U.S. Pat. Nos. 4,521,210; 4,853,224; 4,997,652; 5,164,188; 5,443, 505; 5,501,856; 5,766,242; 5,824,072; 5,869,079; 6,074,661; 6,331,313; 6,369,116; 6,699,493, and 6,726,918.

Other intravitreal therapeutic approaches are described in U.S. application Ser. No. 10/966,764, filed Oct. 14, 2004; Ser. No. 11/039,192, filed Jan. 19, 2005; and 60/587,092, filed Jul. 12, 2004.

It would be advantageous to provide eye implantable drug delivery systems, such as intraocular implants, and methods of using such systems, that are capable of releasing a therapeutic agent at a sustained or controlled rate for extended periods of time and in amounts with few or no negative side effects.

SUMMARY

The present invention provides new drug delivery systems, and methods of using such systems, for extended or sustained drug release into an eye, for example, to achieve one or more desired therapeutic effects while minimizing an increase in ocular pressure in the eye. The drug delivery systems are in the form of implants or implant elements that may be placed in an eye.

Intraocular implants in accordance with the disclosure herein comprise a steroid and a antiglaucoma drug. The steroid and the antiglaucoma drug may be present in or on the same implant or different implants. The antiglaucoma drug may maintain the ocular pressure in the eye in an acceptable range.

Such intraocular implants may comprise a therapeutic component and a drug release sustaining component associated with the therapeutic component. In accordance with the present invention, the therapeutic component comprises, consists essentially of, or consists of, a steroid. The drug release sustaining component is associated with the therapeutic component to sustain release of a therapeutically effective amount of the steroid into an eye in which the implant is placed. The therapeutically effective amount of the steroid is preferably released into the eye for a period of time greater than about two months after the implant is placed in the eye.

In one embodiment, the intraocular implants comprise a steroid and a biodegradable polymer matrix. The steroid is associated with a biodegradable polymer matrix that releases drug, such as by degrading, at a rate effective to sustain release of a therapeutically effective amount of the steroid from the implant for a time greater or longer than about two months from a time the implant is placed in an ocular site or region of an eye. The intraocular implant is biodegradable or bioerodible and provides a sustained release of the steroid in an eye for extended periods of time, such as for more than two months, for example for about three months or more and up to about six months or more.

The biodegradable polymer component of the foregoing implants may be a mixture of biodegradable polymers, wherein at least one of the biodegradable polymers is a polylactic acid or poly(lactide-co-glycolide) polymer having a molecular weight less than 40 kiloDaltons (kD). Additionally or alternatively, the foregoing implants may comprise a first biodegradable polymer having terminal free acid groups, and a different second biodegradable polymer having terminal free acid groups. Furthermore, the foregoing implants may comprise a mixture of different biodegradable polymers, each biodegradable polymer having an inherent viscosity in a range of about 0.16 deciliters/gram (dl/g) to about 0.24 dl/g. Examples of suitable biodegradable polymers include polymers of lactic acid, glycolic acid, and mixtures thereof.

In another embodiment, intraocular implants comprise a therapeutic component that comprises a steroid, and a polymeric outer layer covering the therapeutic component. The polymeric outer layer may include one or more orifices or openings or holes that are effective to allow a liquid to pass into the implant, and to allow the steroid to pass out of the implant. The therapeutic component is provided in a core or interior portion of the implant, and the polymeric outer layer covers or coats the core. The polymeric outer layer may include one or more biodegradable portions. The implant can provide an extended release of the steroid for more or longer than about two months, and for more than about one year, and even for more than about five or about ten years.

In one embodiment, the polymeric outer layer of the implant may comprise two or more layers or coats of biodegradable material, with each such layer having a different composition or rate of degradation than the layer immediately adjoining it. For example, the polymeric outer layer of the implant may comprise concentric rings or nested coatings comprising a first layer, wherein the first layer may comprise, for example, a biodegradable polymer and the absence of a steroid, a biodegradable polymer comprising a therapeutically effective amount of a steroid, a biodegradable polymer comprising an amount of an auxiliary agent effective to reduce at least one side effect of a steroid, and a biodegradable polymer comprising a therapeutically effective amount of a steroid and an amount of an auxiliary agent effective to reduce at least one side effect of a steroid, and a biodegradable polymer without any added drug.

A second layer may also comprise, for example, a biodegradable polymer and the absence of a steroid, a biodegradable polymer comprising a therapeutically effective amount of a steroid, a biodegradable polymer comprising an amount of an auxiliary agent able to reduce at least one side effect of a steroid, and a biodegradable polymer comprising a therapeutically effective amount of a steroid and an amount of an auxiliary agent able to reduce at least one side effect of a steroid, and a biodegradable polymer without any added drug, with the additional provisos that the first and second layers are located adjoining one another in the biodegradable implant, that the first and second layers are not identical, and that the first layer is designed to erode substantially before the second layer.

Additional layers may be present; preferably, each such layer will not be identical to the layers immediately surrounding it.

It is well known that long-term ophthalmic treatment with corticosteroids must be monitored closely due to potential toxicity and long-term side effects. For example, adverse reactions listed for conventional ophthalmic dexamethasone preparations include: glaucoma (with optic nerve damage, visual acuity and field defects, and ocular hypertension), posterior subcapsular cataract formation, and secondary ocular infection from pathogens including herpes simplex. Additional hazardous side-effects upon conventional topical treatment with steroids may comprise hypertension, hyperglycemia, increased susceptibility to infection, and peptic ulcers.

An "auxiliary agent" is an agent able to reduce at least one side effect of a steroid. An auxiliary agent comprises a compound able, in the absence of the steroid, to reduce or prevent a condition associated with at least one side effect of a steroid. Thus such a compound may include, for example, one or more neuroprotective agent such as, without limitation, memantine (and other NMDA receptor antagonists), brimonidine (and other alpha 2 adrenergic receptor agonists) can be therapeutically useful in the treatment of optic nerve and retinal damage affecting loss of visual acuity and diminution of visual field; and/or one or more ocular hypotensive agent such as, without limitation, beta blockers (such as timolol), a carbonic anhydrase inhibitor, an alpha 2 adrenergic agonist (such as clonidine, brimonidine and selective alpha 2B and/or 2C receptor agonists), and a prostaglandin or prostaglandin derivative or analog (such as bimatoprost, travoprost, and latanoprost) for the treatment of ocular hypertension; and/or one or more antiviral and antibiotic drug (for example, a quinolone antibiotic such as ofloxacin, ciprofloxacin and norfloxacin) for the prevention of secondary ocular infection.

In another embodiment, the implant may include a therapeutic agent such as a steroid, and an agent able to reduce at least one side effect of a steroid, wherein art least one of such agents is covalently joined via a biodegradable linkage to a biodegradable polymer. For example, the biodegradable polymer may comprise a plurality of hydroxyl groups to which said agent may be joined by a biodegradable linkage. Biodegradable or biocleavable linkages are defined as types of specific chemical moieties or groups that can be used within the chemical substances that covalently reversibly couple or cross-link a therapeutic agent and/or an auxiliary agent to a biodegradable polymer comprised in the implant. Thus, such linkages may be contained in certain embodiments of the instant invention that provide the function of controlled release of a steroid and/or auxiliary agent. In certain embodiments of the present invention an implant system comprising one or more implant is structured such that the therapeutic agent and the auxiliary agent are released at different rates or different times following implantation of the implant(s). Biocleavable linkages or bonds can be distinguishable by their structure and function and non-limiting examples are provided here under distinct categories or types.

One such category comprises the disulfide linkages that are well known for covalent coupling. Such linkages are stable under oxidizing conditions, but can be cleaved under reducing conditions. For drug delivery, they may be more useful for shorter periods in vivo since they are cleaved relatively easily. A simple ester bond is another preferred type that may easily be formed between an acid and an alcohol. Another preferred type is any imidoester formed from alkyl imidates. Also included are maleimide bonds as with sulfhydryls or amines used to incorporate a biocleavable linkage.

Another category in this invention comprises acid-cleavable biocleavable linkages. The preferred biocleavable linkages for such release of active agents and other moieties. One such type is an acid-sensitive (or acid-labile) hydrazone linkage as described by Greenfield, et al, Cancer Res. 50, 6600-6607 (1990), and references therein.

Another type of acid-labile linkage are the polyortho or diortho ester linkage; examples of such linkages are disclosed in J. Heller, et al., METHODS IN ENZYMOLOGY 112, 422-436 (1985), J. Heller, J. ADV. POLYMER SCI. 107, 41 (1993), M. Ahmad, et al., J. AMER. CHEM. SOC. 101, 2669 (1979) and references therein. Also useful may be acid labile phosphonamide linkages disclosed by J. Rahil, et al, J. AM. CHEM. SOC. 103, 1723 (1981) and J. H. Jeong, et al, BIOCONJ. CHEM. 14, 473 (2003).

The steroid of the implants disclosed herein may be corticosteroids, or other steroids that are effective in treating ocular conditions. One example of a suitable steroid is fluocinolone or fluocinolone acetonide. Another example of a suitable steroid is triamcinolone or triamcinolone acetonide. Another example of a suitable steroid is beclomethasone or beclomethasone dipropionate. Another example of a suitable steroid is dexamethasone or a pharmacologically acceptable salt thereof. In addition, the therapeutic component of the present implants may include one or more additional and different therapeutic agents that may be effective in treating an ocular condition.

The implants may be placed in an ocular region to treat a variety of ocular conditions, including conditions that affect an anterior region or posterior region of an eye. For example, the implants may be used to treat many conditions of the eye, including, without limitation, maculopathies and retinal degeneration, uveitis, retinitis, choroiditis, vascular diseases, and exudative diseases, proliferative disorders, infectious disorders, genetic disorders, tumors, trauma, and surgery, retinal tears or holes, and the like. In particular, treatment of retinal conditions are particularly advantageous by means if insertion, injection or other intravitreal delivery, or subconjunctival delivery of such implants.

Our invention also includes a method for treating an ocular condition by intravitreal placement of a biodegradable implant which comprises a therapeutic component, followed by pulsatile release of the therapeutic component from the implant into the vitreous, thereby treating the ocular condition. The pulsatile release can treat the ocular condition by inhibiting an inflammatory cell function or by inhibiting genesis or proliferation of an inflammatory cell.

Kits in accordance with the present invention may comprise one or more of the present implants, and instructions for using the implants. For example, the instructions may explain how to administer the implants to a patient, and types of conditions that may be treated with the implants.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings and examples.

DRAWINGS

The patent or application file contains at least one drawing executed in color. Copies of this patent or patent application publication with color drawing(s) will be provided by the Office upon request and payment of the necessary fee.

Figure 32:
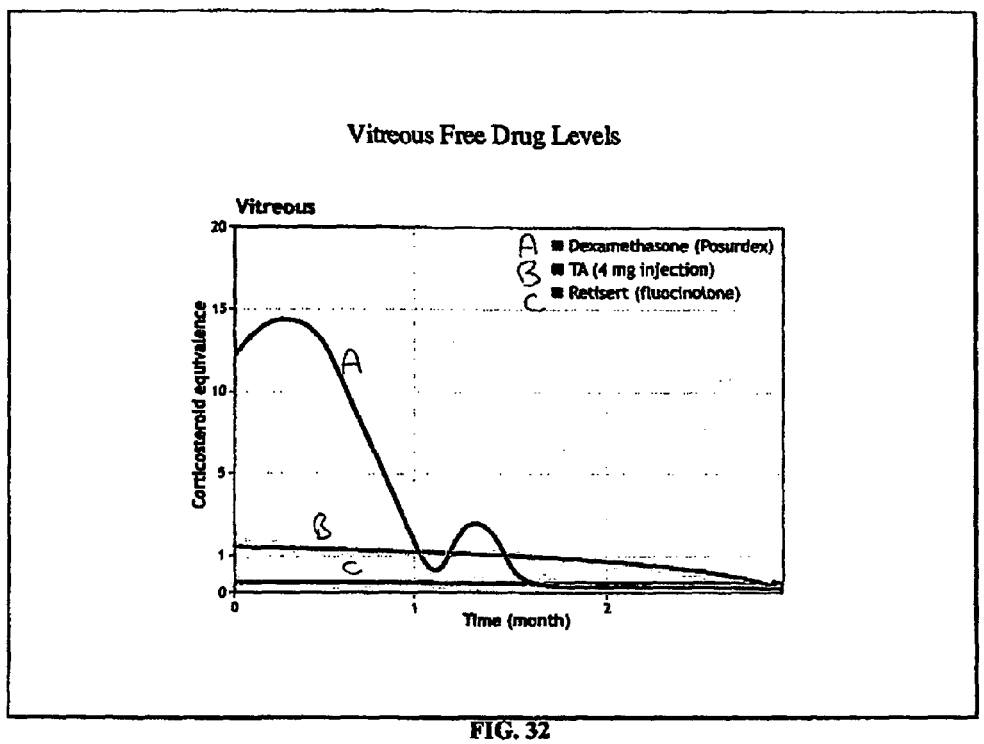

FIG. 32 is a graph showing the intermittent "pulsed" delivery of dexamethasone (the uppermost line on the graph) over a three month period in rabbit vitreous humor following intravitreal administration of a polylactide-polyglycolide (PLGA) filamentous biodegradable intraocular implant containing 700 ug of dexamethasonedexamethasone and comparison with published intravitreal levels of two other intravitreally delivered steroids: a) intraocular injection of 100 μl of a 40 mg/ml triamcinolone acetonide (TA) (the middle line on the graph) aqueous suspension (also containing sodium chloride as a tonicity agent, 10 mg/ml (0.99%) benzyl alcohol as a preservative, 7.5 mg/ml (0.75%) of carboxymethylcellulose sodium and 0.4 mg/ml (0.04%) of polysorbate 80 as a resuspension aid), and b) intravitreal placement of 0.59 mg fluocinolone acetonide (the lowermost line on the graph) (with microcystaline cellulose, polyvinyl alcohol and magnesium stearate) in the Retiserte non-biodegradable intravitreal reservoir (Bausch & Lomb, Inc.). Results are standardized to corticosteroid equivalence units, as described in the text.

Figure 33:
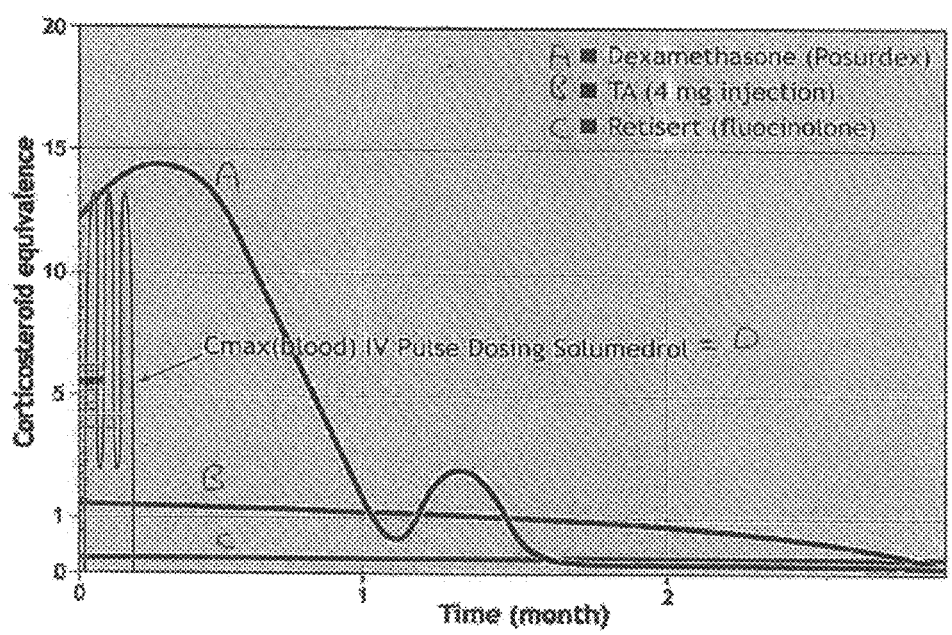

FIG. 33 is FIG. 32 with the addition of a fourth graph line ("D") showing the plasma Cmax upon intravenous administration of solumedrol (methylprednisolone, a corticosteroid). Cmax is the measured maximum plasma concentration.

Figure 34:
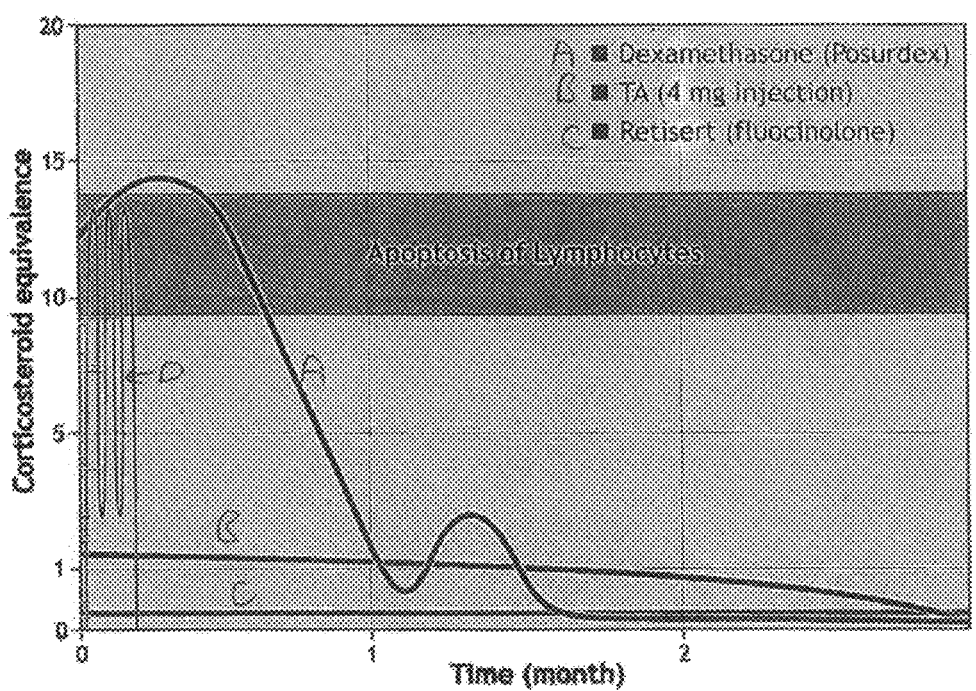

FIG. 34 is FIG. 33 with the addition of a shared bar area which shows the range of corticosteroid concentration at which apoptosis of lymphocytes can occur. "D" in FIG. 34 is the same graph as is "D" in FIG. 33.

Figure 35:
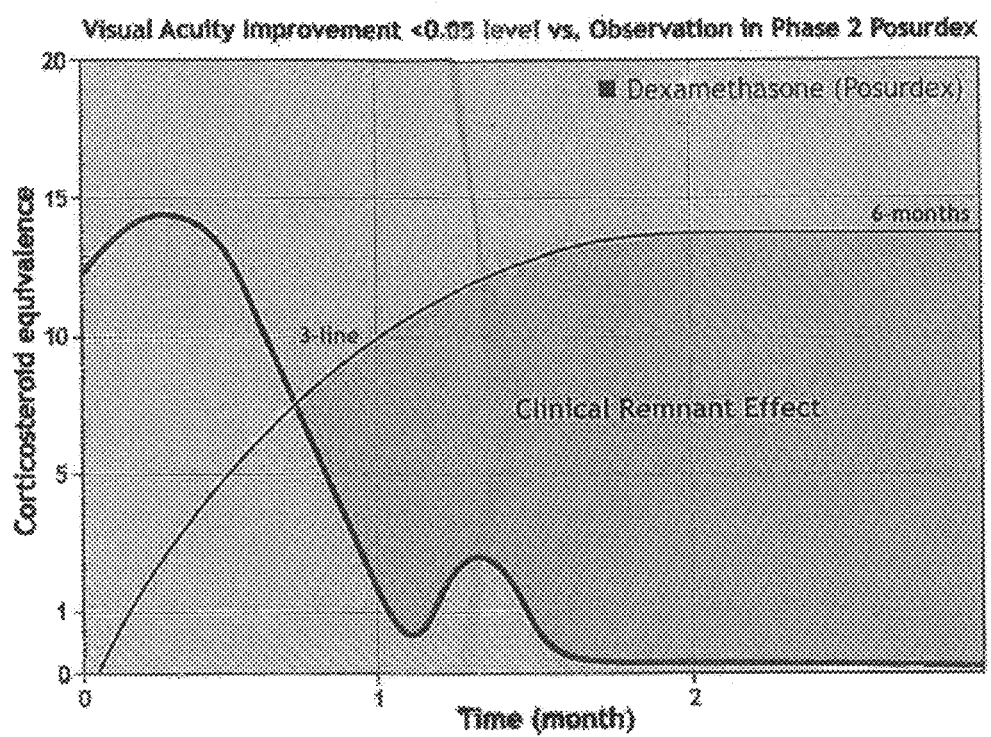

FIG. 35 is FIG. 32 with only the dexamethasone graph shown and with the addition of a graph which illustrates when the clinical remnant effect (maintenance of improved visual acuity after intravitreal placement of a biodegradable implant which released dexamethasone into the vitreous, during a time period when a therapeutic amount of the dexamethasone is not present in the vitreous) can occur.

DESCRIPTION

As described herein, controlled and sustained administration of a therapeutic agent through the use of one or more intraocular implants can be used to treatment an ocular condition. The implants comprise a pharmaceutically acceptable polymeric composition and are formulated to release one or more pharmaceutically active agents including at least one steroid and optionally at least one auxiliary agent, over an extended period of time. In certain embodiments involving the delivery of more than one agent, the dosage regiment may be formulated to provide two or more drugs to the posterior segment of the eye under different dosage regimens. For example, the dosage of the steroid in an implant may be made to be discontinuous over the treatment period while a non-discontinuous dosage of an auxiliary agent is administered in an implant over the same overall time period. The implant containing the steroid and the implant containing the auxiliary agent may be different implants or the same implant comprising means of differentially administering the steroid and auxiliary agent, such means including different coatings or shells which may contain, neither, one or both drugs (as discussed elsewhere herein), or covalent linkage of one or both drugs to a biodegradable polymer of the implant by way of a biodegradable linkage, thus permitting regulation of the delivery of one or more drug over the time of the treatment. The implants are effective to provide a therapeutically effective dosage of the agent or agents directly to a region of the eye to treat one or more undesirable ocular conditions. Thus, with a single administration, therapeutic agents will be made available at the site where they are needed and may be maintained for an extended period of time, rather than subjecting the patient to repeated injections or, in the case of self-administered drops, ineffective treatment with only limited bursts of exposure to the active agent or agents.

A preferred intraocular implant in accordance with the disclosure herein comprises a therapeutic component and a drug release-sustaining component associated with the therapeutic component. In accordance with the present invention, the therapeutic component comprises, consists essentially of, or consists of, a steroid. The drug release sustaining component is associated with the therapeutic component to sustain release of a therapeutically effective amount of the steroid into an eye in which the implant is placed. The therapeutic amount of the steroid is released into the eye for a period of time greater than about two months after the implant is placed in the eye. Preferably the implant also comprises an agent able to reduce at least one side effect of a steroid (AARSS).

DEFINITIONS

The following terms used herein have the meanings set forth below.

"Associated with" means mixed with, dispersed within, coupled to, covering, or surrounding. With respect to intraocular implants which comprise a therapeutic component associated with a biodegradable polymer matrix, "associated with" specifically excludes biodegradable polymeric coatings that may be provided on or around the matrix.

"Biodegradable polymer" means a polymer or polymers which degrade in vivo, and wherein erosion of the polymer or polymers over time occurs concurrently with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

"Drug release sustaining component" means a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

"Inflammatory cell" means a cell which participates is the tissue changes referred to as inflammation. An inflammatory cell can be, for example, a T-cell, a macrophage, a neutrophil, a histiocyte, a granulocyte, a monocyte, a microglia, a lymphocyte, an eosinophil, a mast cell or a B-cell.

"Intraocular implant" means a device or element that is structured, sized, or otherwise configured to be placed "in an eye", including the subconjunctival space. Intraocular implants are generally biocompatible with physiological conditions of an eye and do not cause adverse side effects. Intraocular implants may be placed in an eye without disrupting vision of the eye.

"Therapeutic component" means to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

"Ocular region" or "ocular site" means any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

"Ocular condition" means a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The terms "treat", "treating", or "treatment" mean a reduction or resolution or prevention of an ocular condition, ocular injury or damage, or to promote healing of injured or damaged ocular tissue.

"Therapeutically effective amount" means the level or amount of agent needed to treat an ocular condition, or reduce or prevent ocular injury or damage without causing significant negative or adverse side effects to the eye or a region of the eye.

Intraocular implants have been developed which can release drug loads over various time periods. These implants, which when inserted into an eye, such as, without limitation, the vitreous of an eye or the subconjunctival space, provide therapeutic levels of a steroid and/or auxiliary agent for extended periods of time (e.g., for about 2 months or more). The implants disclosed are effective in treating ocular conditions, such as posterior ocular conditions.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant may comprises a steroid and or auxiliary agent associated with the biodegradable polymer matrix. Such association may be "passive", such as through co-extrusion of the active agent(s) with the biodegradable polymer, or "active", by being joined, or coupled to the polymer through covalent chemical bonds, chelation, strong hydrogen bonding, ionic interaction, and the like. The matrix degrades at a rate effective to sustain release of a therapeutically effective amount of the steroid for a time greater than about two months from the time in which the implant is placed in ocular region or ocular site, such as the vitreous of an eye.

The steroid of the implant may be a corticosteroid. In certain embodiments, the steroid may be a fluocinolone, a triamcinolone, or a mixture of fluocinolone and triamcinolone. In some embodiments, the fluocinolone is provided in the implant as fluocinolone acetonide, and the triamcinolone is provided in the implant as triamcinolone acetonide. Triamcinolone acetonide is publicly available under the tradename, KENALOG®. Another steroid useful in the present implants is beclomethasone or beclomethasone diproprionate. Thus, the present implants may comprise one or more of the following: fluocinolone, fluocinolone acetonide, triamcinolone, triamcinolone acetonide, beclomethasone, or beclamethasone diproprionate.

The steroid may be in a particulate or powder form and entrapped by the biodegradable polymer matrix. Usually, steroid particles will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The steroid of the implant is preferably from about 10 to 90% by weight of the implant. More preferably, the steroid is from about 50 to about 80% by weight of the implant. In a preferred embodiment, the steroid comprises about 50% by weight of the implant. In another embodiment, the steroid comprises about 70% by weight of the implant.

Suitable polymeric materials or compositions for use in the implant include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 60 kD, usually from about 10 to about 54 kD, more usually from about 12 to about 45 kD, and most usually less than about 40 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups. In certain implants, the matrix comprises a first biodegradable polymer having terminal acid groups, and a different second biodegradable polymer having terminal acid groups. The first biodegradable polymer may be a poly (D,L-lactide-co-glycolide). The second biodegradable polymer may be a poly (D,L-lactide).

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. As discussed herein, the matrix of the intraocular implant may release drug at a rate effective to sustain release of a therapeutically effective amount of the steroid for more than three months after implantation into an eye. In certain implants, therapeutic amounts of the steroid are released for more than four months after implantation. For example, an implant may comprise fluocinolone, and the matrix of the implant degrades at a rate effective to sustain release of a therapeutically effective amount of fluocinolone for about three months after being placed in an eye. As another example, the implant may comprise triamcinolone, and the matrix releases drug at a rate effective to sustain release of a therapeutically effective amount of triamcinolone for more than three months, such as from about three months to about six months.

The rate of release of a drug from an implant of the present invention may be related to the physical structure of the implant. In a simple but very useful embodiment, the biodegradable polymer of the present invention may comprise a substantially homogeneous matrix mixed with the active agent(s). Upon drying and formulation of the matrix into an intraocular implant, the active agent may be substantially homogeneously distributed in the matrix. In such an embodiment, the release characteristics of the drug is largely determined by the nature of the solvent and the rate of degradation of the matrix.

In another embodiment the implant may comprise layers or shells of differently formulated biodegradable polymer with which the therapeutic agent and/or auxiliary agent may be associated and released. Concentrations of polymer, therapeutic agent and/or auxiliary agent may differ between layers, or the biodegradable polymer may be formulated to deliver such agents at different rates, according to different release profiles, or over different time periods that other layers, or than a core portion of the implant. Each layer may be formulated differently than at least one other layer, due, without limitation, to differences in drug concentration within different layers, absence or presence of the therapeutic agent and/or the auxiliary agent within different layers; differences in the means by which the drug(s) is associated with the polymer matrix in different layers, or the chemistry and density of the biodegradable materials.

Thus, release of a drug from the present implants can be related to the amount of a drug present in the implant and the properties of the polymers of the implant, such as polymer molecular weight and ratio of glycolic acid to lactic acid. In one embodiment of the present implants, the drug or drugs, such as the steroid and/or auxiliary agent, is released at a first rate for a first time period that is substantially independent of the polymer properties, and the drug or drugs is released at a second rate for a second time period after the first time period that is dependent on the polymer properties of the implant. For example, an implant comprises a steroid and a polymeric component that releases the steroid from the implant for a time period of about thirty days primarily due to steroid dissolution, and releases the steroid from the implant after thirty days primarily due to polymer properties.

One example of the biodegradable intraocular implant comprises a steroid (and/or auxiliary agent) associated with a biodegradable polymer matrix, which comprises a mixture of different biodegradable polymers. At least one of the biodegradable polymers is a polylactide having a molecular weight less than 40 kD. Such a mixture is effective in sustaining release of a therapeutically effective amount at least one agent(s) for a time period greater than about two months from the time the implant is placed in an eye. In certain embodiments, the polylactide has a molecular weight less than 20 kD. In other embodiments, the polylactide has a molecular weight of about 10 kD. The polylactide may be a poly (D,L-lactide), and the polylactide may include polymers having terminal free acid groups. In one particular embodiment, the matrix of the implant comprises a mixture of poly(lactide-co-glycolide) and polylactide. Each of the poly(lactide-co-glycolide) and polylactide may have terminal free acid groups.

Another example of a biodegradable intraocular implant comprises a steroid (and/or auxiliary agent) associated with a biodegradable polymer matrix, which comprises a mixture of different biodegradable polymers, each biodegradable polymer having an inherent viscosity from about 0.16 dl/g to about 0.24 dl/g. For example, one of the biodegradable polymers may have an inherent viscosity of about 0.2 dl/g. Or, the mixture may comprise two different biodegradable polymers, and each of the biodegradable polymers has an inherent viscosity of about 0.2 dl/g. The inherent viscosities identified above may be determined in 0.1% chloroform at 25° C.

Other implants may include a biodegradable polymer matrix of biodegradable polymers, at least one of the polymers having an inherent viscosity of about 0.25 dl/g to about 0.35 dl/g. Additional implants may comprise a mixture of biodegradable polymers wherein each polymer has an inherent viscosity from about 0.50 dl/g to about 0.70 dl/g.

The release of the steroid (and/or auxiliary agent) from the intraocular implant comprising a biodegradable polymer matrix may include an initial burst of release followed by a gradual increase in the amount of the agent released, or the release may include an initial delay in release of the steroid followed by an increase in release. When the implant is substantially completely degraded, the percent of the agent that has been released is about one hundred. Compared to existing implants, in one embodiment the implants disclosed herein do not completely release, or release about 100% of at least one agent (steroid and/or auxiliary agent), until after about two months of being placed in an eye. Thus, the implants exhibit a cumulative release profile that may have a shallower slope, or a lower rate of release, for longer periods of time than existing implants.

In at least one embodiment, the present implants release an active agent into the interior of the eye in an amount having a reduced toxicity relative to bolus or liquid injections of the same agent without a polymeric component. For example, it has been reported that a single or repeated 20 mg dose of Kenalog 40 results in substantial retinal changes, including changes in the retinal pigment epithelium. Such doses may be necessary in liquid formulations to provide prolonged therapeutic effects.

In comparison, the present implants can provide therapeutically effective amounts of the steroid for prolonged periods of time, or for a series of such time periods, without requiring such large doses. Thus, present implants may contain 1 mg, 2 mg, 3 mg, 4 mg, or 5 mg of a steroid, such as triamcinolone acetonide or fluocinolone acetonide, the steroid is gradually released over time without causing substantial ocular toxicity or other adverse side effects that are associated with injection of 20 mg of the steroid in a liquid formulation. The steroid may, in one embodiment, be alternated within different shells of the implant such that it is delivered only over particular time periods, with time periods of substantially less (or no) steroid being delivered intervening. In this way continued exposure of the eye to the steroid, and the side effects that may accompany such constant delivery, may be avoided or reduced. In another embodiment, an intravitreal implant comprises triamcinolone acetonide and a biodegradable polymer associated with the triamcinolone acteonide in the form of an intravitreal implant that releases the triamcinolone acetonide in amounts associated with a reduced toxicity relative to the toxicity associated with administering triamcinolone acetonide in a liquid composition.

It may be in certain cases desirable to provide a relatively constant rate of release of the steroid from the implant over the life of the implant. For example, it may be desirable for the steroid to be released in amounts from about 0.01 µg to about 2 µg per day for the live of the implant. However, the release rate may change to either increase or decrease depending on the formulation of the biodegradable polymer matrix. In addition, the release profile of the steroid may include one or more linear portions and/or one or more non-linear portions. Preferably, the release rate is greater than zero once the implant has begun to degrade or erode.

It may be desirable to include delivery of an auxiliary agent in conjunction with the intravitreal or subconjunctival delivery of a steroid in order to reduce or eliminate at least one side effect compared to the delivery of the steroid in an otherwise identical manner without the auxiliary agent. The auxiliary agent and steroid may be included in the same implant or coadministered in different implants during the same treatment period.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated or reservoir-type implant may be of benefit in some circumstances, where the therapeutic level of the drug falls within a narrow window. In addition, the therapeutic component, including the steroid, may be distributed in a non-homogenous pattern in the matrix. For example, the implant may include a portion that has a greater concentration of the steroid and/or auxiliary agent relative to a second portion of the implant.

In another embodiment of the present invention, an intraocular implant comprises a therapeutic component, including a steroid, and a drug release sustaining component including one or more coating covering a core region of the implant. The therapeutic component and/or auxiliary agent is provided in the core region. The polymeric outer layer may be relatively impermeable to the therapeutic component and ocular fluids. Or, the polymeric outer layer may be initially impermeable to the therapeutic component and ocular fluids, but then may become permeable to the therapeutic component or ocular fluids as the outer layer degrades. Thus, the polymeric outer layer may comprise a polymer such as polytetrafluoroethylene, polyfluorinated ethylenepropylene, polylactic acid, polyglycolic acid, silicone, or mixtures thereof.

The foregoing implant may be understood to include a reservoir of one or more therapeutic agents, such as a steroid and/or auxiliary agent. In certain implants, the steroid may be a corticosteroid, such as fluocinolone or triamcinolone, as discussed above. One example of an implant including a reservoir of a therapeutic agent is described in U.S. Pat. No. 6,331,313.

In some implants, the drug release sustaining component comprises a polymeric outer layer covering the therapeutic component and or the auxiliary agent, the outer layer comprises a plurality of openings or holes through which the therapeutic component may pass from the drug delivery system to an external environment of the implant, such as an ocular region of an eye. The holes enable a liquid to enter into the interior of the implant and dissolve the agent contained therein. The release of the therapeutic agent and/or auxiliary agent from the implant may be influenced by the drug solubility in the liquid, the size of the hole(s), and the number of holes. In certain implants, the hole size and number of holes are effective in providing substantially all of the desired release characteristics of the implant. Thus, additional excipients may not be necessary to achieve the desired results. However, in other implants, excipients may be provided to further augment the release characteristics of the implant.

Various biocompatible substantially impermeable polymeric compositions may be employed in preparing the outer layer of the implant. Some relevant factors to be considered in choosing a polymeric composition include: compatibility of the polymer with the biological environment of the implant, compatibility of the drug with the polymer, ease of manufacture, a half-life in the physiological environment of at least several days, no significant enhancement of the viscosity of the vitreous, and the desired rate of release of the drug. Depending on the relative importance of these characteristics, the compositions can be varied. Several such polymers and their methods of preparation are well-known in the art. See, for example, U.S. Pat. Nos. 4,304,765; 4,668,506 4,959,217; 4,144,317, and 5,824,074, Encyclopedia of Polymer Science and Technology, Vol. 3, published by Interscience Publishers, Inc., New York, latest edition, and Handbook of Common Polymers by Scott, J. R. and Roff, W. J., published by CRC Press, Cleveland, Ohio, latest edition.

The polymers of interest may be homopolymers, copolymers, straight, branched-chain, or cross-linked derivatives. Some exemplary polymers include: polycarbamates or polyureas, cross-linked poly(vinyl acetate) and the like, ethylene-vinyl ester copolymers having an ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer, or mixtures thereof.

Additional examples include polymers such as: poly(methylmethacrylate), poly(butylnethacrylate), plasticized poly (vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), chlorinated poly(ethylene), poly(trifluorochloroethylene), poly(ethylene chlorotrifluoroethylene), poly(tetrafluoroethylene), poly(ethylene tetrafluoroethylene), poly(4,4'-isopropylidene diphenylene carbonate), polyurethane, poly(perfluoroalkoxy), poly(vinylidenefluoride), vinylidene chloride-acrylonitrile copolymer, vinyl chloride-diethyl fumarate copolymer, silicone, silicone rubbers (of medical grade such as Silastic® Medical Grade ETR Elastomer Q7-4750 or Dow Corning® MDX 4-4210 Medical Grade Elastomer); and cross-linked copolymers of polydimethylsilane silicone polymers.

Some further examples of polymers include: poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinyl-olefins), poly(styrene), poly(halo-olefins), poly(vinyls) such as polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, polyvinyl acetate, ethylene vinylchloride copolymer, polyvinyl esters, polyvinylbutyrate, polyvinylformal, poly(acrylate), poly(methacrylate), poly(oxides), poly(esters), poly(amides), and poly(carbonates), or mixtures thereof.

In some aspects, the implants with an outer layer coating with holes may be biodegradable wherein the outer layer degrades after the drug has been released for the desired duration. The biodegradable polymeric compositions may comprise any of the above-identified biodegradable polymers or combinations thereof. In some implants, the polymer is polytetrafluoroethylene, (commercially known as Teflon®), ethyl vinyl alcohol or ethylene vinyl acetate.

The steroid containing implants typically exhibited desirable release times with orifices configured to have a total area of less than 1% of the total surface area of the implant. A substantially cylindrically shaped implant has a first end, a second end, and a body portion between the first end and the second end. Typically, the implants disclosed herein are sealed at the first and second ends. One or more holes are formed in the body portion of the implant. The holes typically have a diameter of at least about 250 μm and less than about 500 μm. For example, holes may have a diameter of about 250 μm, 325 μm, 375 μm, or 500 μm. Smaller holes may be provided in other implants. Typically, two or three holes are provided in the implant outer layer. The holes may be spaced apart by a distance from about 1 mm to about 2 mm for implants having a length of about 7 mm to about 10 mm.

In one steroid-containing implant, the total area of the holes was about 0.311% of the total surface area of the implant. In another steroid-containing implant, the total area of the holes was about 0.9% of the total surface area of the implant. The area of an orifice or hole is determined by the following formula:

$$Area = 3.1416 \times r^2$$

where r is the radius of the orifice. The area for each orifice may be determined and added together to determine the total orifice area. The tubular implant surface area may be determined by the following formula:

$$\text{Surface area} = 3.1416 \times OD \times \text{length} + 2 \times 3.1416 r_{od}^2$$

where OD is the outer diameter of a cross-section of the tubular implant, length is the length of the tubular implant, and $r_{od}$ is the radius of the cross-section of the tubular implant.

In the configurations described above, the implant is capable of releasing the steroid at concentrations less than 2 μg/day. Some implants were capable of releasing the steroid at a concentration of about 0.5 μg/day. These implants are capable of providing therapeutically effective amounts of the steroid to an ocular region of an eye for more than one year, such as for more than five years, and even for about 13 years.

Examples of materials used and methods of making such implants are disclosed in U.S. Pat. No. 6,331,313. Briefly, a coating is formed around a core containing a therapeutic agent. The core may include a therapeutic agent (or a therapeutic component and an auxiliary agent) associated with a biodegradable polymer matrix, or the core may be formed by filling a preformed coating, such as a tube.

The therapeutic agent and auxiliary agent can each be deposited in a preformed coating as a dry powder, particles, granules, or as a compressed solid. The agent or agents may also be present in a solution. In addition, the core can comprise a mixture of a biodegradable polymer matrix and the agent or agents, such as the matrix containing implants described above. The polymers used in the matrix with the therapeutic agent and/or auxiliary agent are bio-compatible, with body tissues and body fluids and can be biodegradable or substantially insoluble in the body fluids. Any of the above-described biocompatible polymer compositions can be used to prepare the matrix. The amount of polymer in the core may be from about 0% to 80 wt % by weight. These polymers are commercially available and methods for preparing polymer matrices are well-known in the art. See, for example, U.S. Pat. No. 5,882,682.

The biocompatible, substantially impermeable outer layer can be obtained by coating the core with a polymeric composition described above. The coat can be applied using organic solvents, and the solvents may then be vacuum stripped from the coat to leave a dry coat. The polymer, at a concentration of from about 10 to about 80 weight percent is dissolved or suspended in an organic solvent at the appropriate temperature, for example for polylactic polymer, between 60 degrees to 90 degrees C. The resulting mixture can be cut, molded, injection molded, extruded, or poured or sprayed onto a pre-formed core into any shape or size for implantation. The spraying can be accomplished in a rotating pan coater or in a fluidized bed coater until the desired coating thickness is achieved.

Alternatively, the core may be dip coated or melt coated. This type of coating is especially useful with waxes and oils. In another embodiment, the core may be compression coated, wherein a suitable polymeric composition may be pressed onto a preformed core. In another aspect, an adhesive coat such as shellac or polyvinyl acetate phthalate (PVAP) is applied to the core prior to applying the impermeable coating in order to improve adhesion of the impermeable coating to the core. These techniques are well-known in the art. See, for example, Handbook of Common Polymers, by J. R. Scott and W. J. Roff, Section 64, (1971) published by CRC Press, Cleveland, Ohio.

When the outer layer is injection molded or extruded into the desired shape, the cavity formed by the outer layer can be then filled with the therapeutic agent and/or auxiliary agent composition. Then, the ends are sealed with an end cap. At least one orifice is drilled in the device. Optionally, an orifice is drilled, or preformed in the wall, or an orifice is sealed with a break-off tab that is broken open, or cut open, or the like, at the time of use.

Alternatively, the core-free device may be loaded with therapeutic agent by, for example, immersing the device in a solution comprising the therapeutic agent for a time sufficient for absorption of the therapeutic agent. The device may be equipped with a hollow fiber and the therapeutic agent and/or auxiliary agent may be directly loaded into the fiber and the device subsequently sealed. Where the activity of the therapeutic agent and/or auxiliary agent will not be compromised, the therapeutic agent-filled device may then be dried or partially dried for storage until use. This method may find particular application where the activity of the therapeutic agent of choice is sensitive to exposure to solvents, heat or other aspects of the conventional solvent-evaporation, molding, extrusion or other methods described above.

The orifice may be formed using any technique known in the art. For instance, the orifice may be made using a needle or other form of boring instrument such as a mechanical drill or a laser to remove a section of the impermeable portion of the device. Alternatively, a specially designed punch tip may be incorporated into the compressing equipment, in order to pierce through the impermeable portion at the point of compaction.

The holes may be made by drilling the appropriate size hole through a wall of the device using a mechanical or laser-based process. In some implants, a digital laser marking system is used to drill the holes. This system allows for an array of apertures to be drilled on both faces of a dosage form simultaneously and at rates suitable for production of dosage forms. The process utilizes a digital laser marking system (for example the DigiMark™ variable marking system, available from Directed Energy, Inc.) to produce an unlimited number of holes through the surface or coating of the dosage form, at rates practically suitable for production of dosage forms.

The steps involved in this laser drilling process are as follows: a digital laser marking system is focused at a laser stage; the dosage form is moved onto the laser stage of the digital laser marking system is pulsed to energize those laser tubes needed to drill the desired apertures along a linear array on the dosage form, the dosage form is moved forward on the laser stage and the digital laser marking system is again pulsed as needed to produce an additional linear array of apertures; the dosage form is then removed from the laser stage.

Orifices and equipment for forming orifices are disclosed in U.S. Pat. Nos. 3,845,770; 3,916,899; 4,063,064 and 4,008,864. Orifices formed by leaching are disclosed in U.S. Pat. Nos. 4,200,098 and 4,285,987. Laser drilling machines equipped with photo wave length detecting systems for orienting a device are described in U.S. Pat. No. 4,063,064 and in U.S. Pat. No. 4,088,864.

The intraocular implants disclosed herein may have a size of between about 5 μm and about 10 mm, or between about 10 μm and about 1 mm for administration with a needle, greater than 1 mm, or greater than 2 mm, such as 3 mm or up to 10 mm, for administration by surgical implantation. For needle-injected implants, the implants may have any appropriate length so long as the diameter of the implant permits the implant to move through a needle. For example, implants having a length of about 6 mm to about 7 mm have been injected into an eye. The implants administered by way of a needle should have a diameter that is less than the inner diameter of the needle. In certain implants, the diameter is less than about 500 µm. The vitreous chamber in humans is able to accommodate relatively large implants of varying geometries, having lengths of, for example, 1 to 10 mm. The implant may be a cylindrical pellet (e. g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 µg, more preferably about 500-1000 µg. For example, an implant may be about 500 µg, or about 1000 µg. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants, particularly the implants with the steroid and/or auxiliary agent associated with a biodegradable polymer matrix, may be of any geometry including fibers, sheets, films, microspheres and microparticles, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 µm to 4 mm in diameter, with comparable volumes for other shaped particles.

In certain embodiments of the present invention the use if microsphere implants may be particularly advantageous. A method of making such microspheres involves combining, associating or mixing the therapeutic and/or auxiliary agent with a biodegradable polymer or polymers. The mixture may then be extruded or compressed to form a single composition. The single composition may then be processed to form microspheres suitable for placement intravitreally or subconjunctivally.

Alternatively, a method of making the present microspheres may also include using an oil-in-oil emulsion process to form the microspheres. Such methods may be particularly useful in forming microparticles, nanoparticles and the like. Thus, an embodiment of the present invention relates to the inserts comprising microparticles made using an oil-in-oil emulsion process.

The microspheres, which may include a population of microparticles or nanoparticles, may be placed in an ocular region such as, without limitation, intravitreally or subconjunctivally, to treat a variety of ocular conditions. For example, the microspheres may be administered intravitreally in a manner effective to delivering a therapeutic component and/or auxiliary agent to tissues of the posterior segment, thereby reducing damage to the tissues of the posterior segment while reducing at least one side effect as compared to the administration of the steroid alone in an otherwise identical manner. Alternatively, subconjunctival administration of the microspheres of the present invention are very effective at delivering the therapeutic component to the retina and other tissues of the posterior segment for the treatment of neurodegenerative conditions such as age related macular degeneration (ARMD), such as "wet" or "dry" ARMD, macular edema, etc.

The use of microspheres, microparticles and the like provides an excellent means of punctuated delivery of the steroid in the implants of the present invention. For example, in one embodiment different lots (comprising the same or different sizes of microparticles) are made, each having a different property, such as different rates of erosion; different drug content (for example some may contain a steroid and an auxiliary agent, while others may just contain the auxiliary agent; some may be made of one bioerodable polymer having a fast dissolution rate, while others may be made of a different biopolymer having a slower dissolution rate. By engineering the microparticles so that during the treatment period the dosage of steroid is "pulsed", for example, from an initial substantially optimal therapeutically effective dosage to a subsequent period lacking a substantially optimal therapeutically effective dosage of the steroid and optionally to another treatment time period in which a substantially optimal therapeutically effective dosage of the steroid is again administered, at least one of the deleterious side effects of long term steroid use can be lessened. Some microspheres may, for example, be loaded with the auxiliary agent, either alone or in combination with the steroid, to provide a substantially constant (or at least slowly decaying) dosage of the auxiliary agent to ocular tissues during the treatment period, while the dosage of steroid may vary.

Thus, the combination of different microspheres in a discretely administered intravitreal or subconjunctival injection or insertion provides a powerful way to separately tailor the administration of steroid and auxiliary agent. Methods of making microspheres are provided in U.S. application Ser. No. 11/303,462, and U.S. application Ser. No. 10/837,260, under common ownership with the present application, the entire contents of both of which prior applications are hereby incorporated by reference.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

The proportions of steroid and/or auxiliary agent, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the steroid or steroids included in the intraocular implants disclosed herein, the intraocular implants may also include one or more additional ophthalmically acceptable therapeutic agents. For example, the implant may include one or more antihistamines, one or more antibiotics, one or more beta blockers, one or more different corticosteroids, one or more neuroprotectant agent, one or more anti-glaucoma agent, one or more antibiotic, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. No. 4,474,451, columns 4-6 and U.S. Pat. No. 4,327,725, columns 7-8.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, ofloxacin, ciprofloxacin, norfloxacin, and derivatives thereof.

Examples of beta blockers include acebutolol, atenolol, labetalol, metoprolol, propranolol, timolol, and derivatives thereof.

Examples of other corticosteroids include cortisone, prednisolone, flurometholone, dexamethasone, medrysone, loteprednol, fluazacort, hydrocortisone, prednisone, betamethasone, prednisone, methylprednisolone, riamcinolone hexacatonide, paramethasone acetate, diflorasone, fluocinonide, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valciclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, Ginkgo Biloba extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, neuroprotectants such as NMDA receptor antagonists and alpha 2 adrenergic agonists, prostaglandins, antiparasitics, antifungals, and derivatives thereof.

The amount of active agent or agents employed in the implant, individually or in combination, will vary widely depending on the effective dosage required and the desired rate of release from the implant. Usually the agent will be at least about 1, more usually at least about 10 weight percent of the implant, and usually not more than about 80, more usually not more than about 40 weight percent of the implant.

In addition to the therapeutic component and/or auxiliary agent, the intraocular implants disclosed herein may include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

In some situations mixtures of implants may be utilized employing the same or different pharmacological agents. In this way, a cocktail of release profiles, giving a multiphasic release with a single administration is achieved, where the pattern of release may be greatly varied.

Additionally, release modulators such as those described in U.S. Pat. No. 5,869,079 may be included in the implants. The amount of release modulator employed will be dependent on the desired release profile, the activity of the modulator, and on the release profile of the glucocorticoid in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

Various techniques may be employed to produce the implants described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degree C. to about 150 degree C., more preferably about 65 degree C. to about 130 degree C. An implant may be produced by bringing the temperature to about 60 degree C. to about 150 degree C. for drug/polymer mixing, such as about 130 degree C., for a time period of about 0 to 1 hour, 0 to 30 minutes, or 5-15 minutes. For example, a time period may be about 10 minutes, preferably about 0 to 5 min. The implants are then extruded at a temperature of about 60 degree C. to about 130 degree C., such as about 75 degree C.

In addition, the implant may be coextruded so that a coating is formed over a core region during the manufacture of the implant.

Compression methods may be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degree C., more preferably about 25 degree C.

The implants of the present invention may be inserted into the eye, for example the vitreous chamber of the eye, by a variety of methods, including placement by forceps or by trocar following making a 2-3 mm incision in the sclera. The method of placement may influence the therapeutic component or drug release kinetics. For example, delivering the implant with a trocar may result in placement of the implant deeper within the vitreous than placement by forceps, which may result in the implant being closer to the edge of the vitreous. The location of the implant may influence the concentration gradients of therapeutic component or drug surrounding the element, and thus influence the release rates (e.g., an element placed closer to the edge of the vitreous may result in a slower release rate).

The implants of the present invention may also, or alternatively, be inserted into the subconjunctival space such as by injection or surgical insertion. Applicants are aware that effective retinal delivery is effectively provided by such subconjunctival administration.

Among the diseases/conditions which can be treated or addressed in accordance with the present invention include, without limitation, the following:

Maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal teiangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Biefti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In one embodiment, an implant, such as the implants disclosed herein, is administered to a posterior segment of an eye of a human or animal patient, and preferably, a living human or animal. In at least one embodiment, an implant is administered without accessing the subretinal space of the eye. For example, a method of treating a patient may include placing the implant directly into the posterior chamber of the eye. In other embodiments, a method of treating a patient may comprise administering an implant to the patient by at least one of intravitreal injection, subconjuctval injection, sub-tenon injections, retrobulbar injection, and suprachoroidal injection.

In at least one embodiment, a method of treating a posterior ocular condition comprises administering one or more implants containing one or more steroids, as disclosed herein to a patient by at least one of intravitreal injection, subconjuctival injection, sub-tenon injection, retrobulbar injection, and suprachoroidal injection. A syringe apparatus including an appropriately sized needle, for example, a 22 gauge needle, a 27 gauge needle or a 30 gauge needle, can be effectively used to inject the composition with the posterior segment of an eye of a human or animal. Repeat injections are often not necessary due to the extended release of the steroid from the implants.

The present implants provide prolonged therapy to patients in need of ocular therapy. As discussed herein, the present implants can release a steroid for at least about 2 months after placement in the vitreous of an eye of a patient. In certain implants, the steroid, and/or other therapeutic agents, can be released for at least about one year, for example for about three years. In additional implants, the steroid and/or auxiliary agent can be released at therapeutically effective amounts for more than three years, such as for about five years.

In another aspect of the invention, kits for treating an ocular condition of the eye are provided, comprising: a) a container comprising an extended release implant comprising a therapeutic component including a steroid, such as fluocinolone or triamcinolone, an auxiliary agent, and optionally a drug release sustaining component; and b) instructions for use. Instructions may include steps of how to handle the implants, how to insert the implants into an ocular region, and what to expect from using the implants.

In view of the disclosure herein, one embodiment of a biodegradable intraocular implant comprises a steroid, such as triamcinolone acetonide, fluocinolone acetonide, dexamethasone, and the like, optionally an auxiliary agent, and a biodegradable polymeric component, and substantially no polyvinyl alcohol. Such an implant may be useful in treating uveitis, including non-infectious uveitis, and other ocular disorders, including macular edema, age-related macular degeneration, and the disorders described herein. Advantageously, these implants can be placed in the vitreous of an eye of a patient, and can provide one or more therapeutic benefits with relatively few or no side effects. For example, the steroid, such as fluocinolone acetonide, can be released from the implant without the patient developing cataracts, vitreous hemorrhage, retinal neovascularization, and/or ocular hypertension.

In another embodiment, the implant can comprise a steroid, such as fluocinolone acetonide, optionally an auxiliary agent, and the implant can have a form other than a tablet. For example, the implant can be in the form of a rod, sphere, particle and the like. In certain implants, the implant is an extruded element as compared to a compressed tablet. The implant may include an adhesive component effective in retaining the implant in a fixed position in the eye. For example, certain implants, such as non-tablet implants, may include a polyvinyl alcohol suture. Other implants, including compressed tablets, may include an adhesive component that is free of polyvinyl alcohol. For example, a hydrogel material may be used to affix the implant in the eye of a patient.

In another embodiment, a steroid-containing intraocular tablet may comprise a polyvinyl alcohol coating over the tablet body, and be substantially free of a silicone component. Some examples of useful coatings include those described above.

In a further embodiment, an implant can comprise a steroid, such as fluocinolone acetonide or triamcinolone acetonide, and an intraocular pressure reducing agent or antiglaucoma drug. These implants may be particularly useful in preventing an increase in intraocular pressure associated with release of the steroid from the implant into the eye. The term antiglaucoma drug, as used herein, is meant to include both the terms intraocular pressure reducing agent and antiglaucoma drug.

It will be understood that antiglaucoma drugs need not necessarily be ocular hypotensive drugs. Although elevated intraocular pressure accompanies most cases of glaucoma, is not always present. Thus, for example, "low-tension" or "normal-tension" glaucoma is a condition that causes optic nerve damage and narrowed side vision in people with normal eye pressure. While lowering eye pressure helps at least 30 percent of these patients slow the progression of the disease, glaucoma may worsen in others despite low intraocular pressure.

Therefore, certain antiglaucoma drugs may have neuroprotective activity in addition to, or instead of ocular hypotensive activity.

A wide range of antiglaucoma drugs may be utilized in the ocular implants according to embodiments of the present invention. For example, six types of antiglaucoma drugs are listed on the website of the New York Glaucoma Research Institute (NYGRI), www.glaucoma.net/nygri/glaucoma/topics/drugs.html. It will be understood that this classification of antiglaucoma drugs contains some overlap, does not necessarily contain all classes of therapeutic agents useful for the treatment of glaucoma, and is not necessarily the sole classes of antiglaucoma agents. These types are: 1. Parasympathomimetics; 2. Sympathomimetics; 3. Alpha agonists; 4. Beta Blockers; 5. Carbonic anhydrase inhibitors; and 6. Prostaglandin analogs.

Implants according to embodiments of the present invention may comprise one or more types of antiglaucoma drugs. In addition to the 6 types of antiglaucoma drugs listed on the NYGRI website, other types of antiglaucoma drugs may be utilized in the implants in alternative embodiments.

Antiglaucoma drugs have been reviewed, for example, by Ivan Goldberg in *Aust. Preser.* 25, 142 (2002), and by S. D. Mathebula in *The South African Optometrist*, September, 2005, pages 89-95. The antiglaucoma drugs that are described in these reviews may be employed as antiglaucoma drugs in the implants according to embodiments of the present invention.

Intraocular pressure reducing agents or antiglaucoma drugs may reduce the intraocular pressure through various mechanisms. Although the following discussion generally follows the classification scheme of the six types of antiglaucoma drugs on the NYGRI website for convenience, the discussion is illustrative only and is not meant to be limiting.

1. Parasympathomimetics

Parasympathomimetics, also known as miotics, cholinomimetrics, or cholinergic agents, may function by opening the trabecular meshwork and increase the rate of fluid outflow from the anterior chamber of the eye. Some nonlimiting examples of parasympathomimetics include pilocarpone, carbachol, and echothiophate and their derivatives.

2. Sympathomimetics

Sympathomimetics, also known as adrenergic agonists, may lower the intraocular pressure by increasing the rate of fluid outflow from the anterior chamber of the eye and may also decrease the rate of aqueous humor production.

Epinephrine (adrenaline) may be the most commonly used sympathomimetic antiglaucoma drug; it is a natural agonist at alpha 2 adrenergic receptors. Dipivefrin is a precursor of epinephrine and may be converted to epinephrine inside the eye. Dipivefrin may therefore also be considered to be a sympathomimetic.

Other sympathomimetrics may also be suitable.

3. Alpha Agonists

Alpha-agonists, particularly those possessing alpha 2 adrenergic receptor activity, may reduce aqueous humor production and increase aqueous humor outflow. Apraclonidine, clonidine, p-aminoclonidine, oxymetazoline, epinephrine, norepinephrine, and cirazoline, dexmedatomidine, mivazerol, xylazine, medatomidine, and brimonidine are nonlimiting examples of such alpha 2 agonists. Compounds possessing selective alpha 2 activity, that is a minimum of alpha 1 agonist activity, are particularly helpful.

Additionally, newer classes of alpha 2 agonist compounds, such as those compounds possessing alpha 2B and/or alpha 2C selective activity, may be particularly useful in providing antiglaucoma activity without concomitant sedation or cardiovascular suppression.

Examples of such compounds, methods of their making, and methods of screening such compounds are provided, for example and without limitation, in the following publications, all of which are incorporated herein by reference in their entirety: U.S. Pat. Nos. 6,329,369; 6,545,182; 6,841,684 and U.S. Patent Publications Serial No US20020161051, entitled "(2-hydroxy)ethyl-thioureas useful as modulators of alpha2B adrenergic receptors"; US20030023098, entitled "Compounds and method of treatment having agonist-like activity selective at alpha 2B or 2B/2C adrenergic receptors"; US20030092766, entitled "Methods and compositions for modulating alpha adrenergic receptor activity"; US20040220402, entitled "4-(substituted cycloalkylmethyl) imidazole-2-thiones, 4-(substituted cycloalkenylmethyl) imidazole-2-thiones, 4-(substituted cycloalkylmethyl) imidazol-2-ones and 4-(substituted cycloalkenylmethyl) imidazol-2-ones and related compounds"; US20040266776, entitled "Methods of preventing and reducing the severity of stress-associated conditions"; US20050059664 entitled "Novel methods for identifying improved, non-sedating alpha-2 agonists"; US20050059721, entitled "Nonsedating alpha-2 agonists"; US20050059744 entitled "Methods and compositions for the treatment of pain and other alpha 2 adrenergic-mediated conditions"; and US20050075366 entitled "4-(2-Methyl-5,6,7,8-tetrahydro-quinolin-7-ylm-ethyl)-1,3-dihydro-imidazole-2-thione as specific alpha2B agonist and methods of using the same". Additional disclosure concerning non-sedating alpha 2 adrenergic agonists can be found in US20050058696, entitled Methods and Compositions for the Treatment of Pain and other Alpha 1 Adrenergic Mediated Conditions", and US20040132824, entitled "Novel Methods and Compositions of Alleviating Pain". All the patents and patent applications referenced above are incorporated by reference herein in their entirety.

These publications show that such non-sedating $\alpha 2$ receptor agonist compositions contain agents that have already been characterized in a wide variety of chemical classes, including the imidazole, thiourea, imidazoline, and imidazole thione, phenethylamine, amino thiazine, amino imidazoline, benzazepine, amino oxazoline, amino thiazoline, quinazoline, guanidine, piperazine, yohimbine alkaloid, and phenoxypropanolamine chemical classes. It is to be expected that future non-sedating $\alpha 2$ agents (or combinations of agents) will be found in additional chemical classes.

In particular, it has been found that non-sedating $\alpha 2$ adrenergic agonist compositions have certain biochemical properties in common, regardless of the chemical structure of the agents contained in the compositions. For example, in one embodiment such compounds, in addition to having $\alpha 2$ adrenergic agonist activity, particularly but not necessarily exclusively, $\alpha 2B$ and/or $\alpha 2C$ adrenoreceptor activity, also lack significant $\alpha 1$ adrenoreceptor activity. However, in another embodiment, a therapeutic composition comprising a non-sedating $\alpha 2$ adrenergic agonist may comprise a combination of an $\alpha 2$ adrenergic agonist with an $\alpha 1$ adrenergic antagonist. In each case, the reduced or absent $\alpha 1$ adrenergic activity results in a significant increase in the efficacy of the $\alpha 2$ adrenergic agonist activity (reduced EC50 or concentration at which half the maximum therapeutic effect for that compound is seen) with no significant increase in the potency of the sedative activity. Thus, at therapeutically effective concentrations, the $\alpha 2$ adrenergic agonist has little or no sedative effect, particularly as compared to a composition comprising an $\alpha 2$ adrenergic agonist at a dosage conferring the same therapeutic effect, but lacking significant $\alpha 1A$ inhibitory activity.

Other classes of non-sedating alpha 2 receptor agonists may include those having alpha 2B and/or alpha 2C agonist activity, but lacking alpha 2A receptor activity. These compounds have greatly reduced or absent sedative activity, but retain the neuroprotective and ocular hypotensive activities characteristic of alpha 2 agonists.

4. Beta-Blockers

Beta-blockers, also known as sympatholytics or adrenergic antagonists, can decrease the rate at which fluid flows into the anterior chamber of the eye. According to the Mathebula review, beta blockers can inhibit aqueous humor formation while leaving the rate of aqueous humor outflow unchanged.

Nonlimiting examples of commonly used beta-blockers include timolol, levobunolol, metipranolol, carteolol, and betaxolol.

5. Carbonic Anhydrase Inhibitors

Carbonic anhydrase inhibitors (CAIs) inhibit the enzyme carbonic anhydrase. Carbonic anhydrase is an important enzyme in the body's formation of aqueous humor. Inhibiting the formation of aqueous humor may reduce the intraocular pressure by better modulating the rates of aqueous humor inflow and outflow. According to the Mathebula review, when the intraocular pressure needs to be lowered quickly, carbonic anhydrase inhibitors may be the drugs of choice to achieve this purpose.

Some nonlimiting examples of carbonic anhydrase inhibitors include dorzolamide, brinzolamide, and dichlorphenamide.

6. Prostaglandin Analogs and Derivatives

Prostaglandin analogs and derivatives may increase uveoscleral outflow of the aqueous humor. Prostaglandins were regarded as potent ocular hypertensives for many years; however, evidence accumulated in the last two decades shows that some prostaglandins are highly effective ocular hypotensive agents and are ideally suited for the long-term medical management of glaucoma. (See, for example, Starr, M. S. Exp. Eye Res. 1971, 11, pp. 170-177; Bito, L. Z. Biological Protection with Prostaglandins Cohen, M. M., ed., Boca Raton, Fla., CRC Press Inc., 1985, pp. 231-252; and Bito, L. Z., Applied Pharmacology in the Medical Treatment of Glaucomas, Drance, S. M. and Neufeld, A. H. eds., New York, Grune & Stratton, 1984, pp. 477-505). These references are hereby incorporated by reference in their entirety. Such prostaglandins include PGF2α, PGF1α, PGE2, and certain lipid-soluble esters, such as $C_1$ to $C_5$ alkyl esters, e.g. 1-isopropyl ester, of such compounds.

In U.S. Pat. No. 4,599,353 certain prostaglandins, in particular PGE2 and PGF2$_\alpha$ and the $C_1$ to $C_5$ alkyl esters of the latter compound, were reported to possess ocular hypotensive activity and were recommended for use in glaucoma management.

The precise mechanism by which prostaglandins exert their effects is not yet known. However, while not wishing to be limited by theory, recent experimental results indicate that the prostaglandin-induced reduction in intraocular pressure results from increased uveoscieral outflow [Nilsson et al., INVEST. OPHTHALMOL. VIS. SCI. 28(suppl), 284 (1987)].

The isopropyl ester of PGF2α has been shown to have significantly greater hypotensive potency than the parent compound, which was attributed to its more effective penetration through the cornea. In 1987, this compound was described as "the most potent ocular hypotensive agent ever reported." [See, for example, Bito, L. Z., Arch. Ophthalmol. 105, 1036 (1987), and Siebold et al., Prodrug 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular PGF2α and its prodrugs, e.g. its 1-isopropyl ester, in humans. The clinical potential of prostaglandins in the management of conditions associated with increased ocular pressure, e.g. glaucoma, has been limited by these side effects.

Certain prostaglandins and their analogs and derivatives, such as the PGF$_{2\alpha}$ derivative latanoprost, sold under the trademark Xalatan®, have been established as compounds useful in treating ocular hypertension and glaucoma. However, latanoprost, the first prostaglandin approved by the United States Food And Drug Administration for this indication, is a prostaglandin derivative possessing the undesirable side effect of producing an increase in brown pigment in the iris of 5-15% of human eyes. The change in color results from an increased number of melanosomes (pigment granules) within iridial melanocytes. See e.g., Watson et al., OPHTHALMOLOGY 103:126 (1996). While it is still unclear whether this effect has additional and deleterious clinical ramifications, from a cosmetic standpoint alone such side effects are usually undesirable.

Certain phenyl and phenoxy mono, tri and tetra prostaglandins and their 1-esters are disclosed in European Patent Application 0,364,417 as useful in the treatment of glaucoma or ocular hypertension.

In a series of United States patent applications assigned to Allergan, Inc. prostaglandin esters with increased ocular hypotensive activity accompanied with no or substantially reduced side-effects are disclosed. U.S. patent application Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl PGF2α. Intraocular pressure reducing 15-acyl prostaglandins are disclosed in U.S. Ser. No. 357,394 (filed May 25, 1989). Similarly, 11,15-9,15- and 9,11-diesters of prostaglandins, for example 11,15-dipivaloyl PGF2α are known to have ocular hypotensive activity. See U.S. Pat. No. 4,494,274; U.S. patent Ser. No. 584,370, and U.S. Pat. No. 5,034,413; the parent applications were filed on Jul. 27, 1989.

Woodward et al U.S. Pat. Nos. 5,688,819 and 6,403,649 disclose certain cyclopentane heptanoic acid, 2-cycloalkyl or arylalkyl compounds as ocular hypotensives. These compounds, which can properly be characterized as hypotensive lipids, are effective in treating ocular hypertension.

As one example, the prostamide, bimatoprost, has been discovered to be effective in reducing intraocular pressure possibly by increasing the aqueous humour outflow of an eye (Woodward et al., AGN 2024 (Lumigan®): A Synthetic Prostamide Analog that Lowers Primate Intraocular Pressure by Virtue of Its Inherent Pharmacological Activity, ARVO 2002; (CD-ROM):POS; Chen et al., Lumigan®: A Novel Drug for Glaucoma Therapy, OPTOM IN PRACT, 3:95-102 (2002); Coleman et al., A 3-Month Randomized Controlled Trial of Bimatoprost (LUMIGAN) versus Combined Timolol and Dorzolamide (Cosopt) in Patients with Glaucoma or Ocular Hypertension, OPHTHALMOLOGY 110(12): 2362-8 (2003); Brubaker, Mechanism of Action of Bimatoprost (Lumigan™), SURV OPHTHALMOL 45 (Suppl 4):S347-S351 (2001); and Woodward et al., The Pharmacology of Bimatoprost (Lumigan™), SURV OPHTHALMOL 45 (Suppl 4) S337-S345 (2001).

Bimatoprost is a structural derivative of a naturally occurring prostamide. Bimatoprost's chemical name is (Z)-7-[(1R, 2R,3R,5S)-3,5-Dihydroxy-2-[1E,3S)-3-hydroxy-5-phenyl-1-pentenyl]cyclopentyl]-5-N-ethylheptenamide, and it has a molecular weight of 415.58. Its molecular formula is $C_{25}H_{37}NO_4$. Bimatoprost is available in a topical ophthalmic solution under the tradename Lumigan® (Allergan, Inc.). Each mL of the solution contains 0.3 mg of bimatoprost as the active agent, 0.05 mg of benzalkonium chloride (BAK) as a preservative, and sodium chloride, sodium phosphate, dibasic; citric acid; and purified water as inactive agents.

In addition to latanoprost and bimatoprost, unoprostone is another example of a currently marketed prostaglandin inhibitors. Other prostaglandin inhibitors may be utilized in alternative embodiments.

Combinations of antiglaucoma drugs or intraocular pressure reducing agents may also be used in embodiments of the present invention.

It is commonly thought that drug combinations that act on different receptor sites or enzymes and that have different modes of action are preferred. Table 3 of the Mathebula reference provides a matrix of classes of antiglaucoma drugs showing some classes of antiglaucoma drugs that can have an additive or synergistic effect on one another compared to the use of a single class of antiglaucoma drugs.

As an example, beta blockers, which lower aqueous humor production, can be combined with miotics, which enhance aqueous trabecular outflow.

As another example, the beta blocker betaxolol can be combined with the sympathomimetics epinephrine or dipivefrin. The combination results in a significant reduction in intraocular pressure due to increased oufflow of fluid from the eye.

Timolol may be used in combination with dorzolamide, brimonidine or latanoprost. Other combinations of antiglaucoma drugs may be utilized in other embodiments.

In an embodiment of the present invention, an ocular implant can comprise a steroid and an auxiliary agent, wherein said auxiliary agent comprises an antiglaucoma drug.

In another embodiment, a first ocular implant can comprise a steroid, and a second ocular implant can comprise an auxiliary agent comprising an antiglaucoma drug.

In yet another embodiment, mixtures of implants may be utilized, where the mixture of implants may be selected from the group consisting of an implant that comprises a steroid, an implant that comprises an antiglaucoma drug, an implant that comprises a mixture of a steroid and an antiglaucoma drug, and mixtures thereof.

The steroid may, without limitation, be selected from the group consisting of dexamethasone, fluocinolone, fluocinolone acetonide, triamcinolone, triamcinolone acetonide, beclomethasone, beclamethasone diproprionate, and mixtures thereof. Other steroids may be utilized in other embodiments.

It will be understood that the antiglaucoma drugs discussed herein comprise a specific example of an auxiliary agent.

In this embodiment of the invention the antiglaucoma drug (auxiliary agent) may, without limitation, be selected from the group consisting of a parasympathomimetic, a sympathomimetic, an alpha agonist, a beta blocker, a carbonic anhydrase inhibitor, a prostaglandin analog, an ocular neuroprotectant, and mixtures thereof. Other types of antiglaucoma drugs may be utilized in other embodiments.

The antiglaucoma drug may, without limitation, also be selected from the group consisting of pilocarpone, carbachol, echothiophate, epinephrine, dipivefrin, apracionidine, timolol, levobunolol, metipranilol, carteolol, betaxolol, dorzolamine, brinzolamide, dichlorphenamide, latanoprost, bimatoprost, unoprostone, apraclonidine, clonidine, p-aminoclonidine, oxymetazoline, norepinephrine, cirazoline, dexmedatomidine, mivazerol, xylazine, medatomidine, and brimonidine and mixtures thereof. Other antiglaucoma drugs may also be suitable.

The ocular implants according to these embodiments of the present invention may comprise any of the polymeric matrices, geometric configurations, or other embodiments of implants that were previously described for ocular implants that comprise steroids.

In some embodiments, an implant that comprises a steroid and an antiglaucoma drug may comprise a first polymeric matrix that may be associated with the steroid and a second polymeric matrix that may be associated with the antiglaucoma drug. The first polymeric matrix may be the same as the second polymeric matrix, or the first polymeric matrix may be different than the second polymeric matrix.

Similarly, in an embodiment where a first implant comprises a steroid, and a second implant comprises an antiglaucoma drug, the first implant and the second implant may comprise the same polymeric matrix, or the first implant and the second implant may comprise different polymeric matrices.

The rate of release and the timing of release of the steroid and the antiglaucoma drug from the implant or implants may be optimized, for example, by adjusting the amounts and types of the polymeric formulations that form the polymeric matrices of the implant or implants.

In some embodiments, the implant comprising the steroid, the antiglaucoma drug, or both the steroid and the antiglaucoma drug may comprise at least one layer or coating covering a core region of the implant. In some embodiments, the covering may comprise a plurality of openings or holes through which the steroid, the antiglaucoma drug, or both the steroid and the antiglaucoma drug may pass to an external environment, for example to the ocular region of the eye.

The properties of the coating and the size or number of openings or holes in the coating may be adjusted to provide optimum delivery of the steroid and antiglaucoma drug.

The timing and the duration of release of the steroid and antiglaucoma drug may therefore be adjusted, for example, by changing the formulation of the polymeric matrix and/or the configuration of the implant or implants.

In some embodiments, the steroid may be released from the implant or implants simultaneously with the release of the antiglaucoma drug from the implant.

In other embodiments, the antiglaucoma drug may be released from the implant or implants at a different time than a time when the steroid is released.

For example, in some embodiments, the antiglaucoma drug may be released from the implant or implants before the steroid is released. In other embodiments, the antiglaucoma drug may be released from the implant or implants after the steroid is released.

In still other embodiment, the release of the steroid may be pulsed or otherwise varied while the antiglaucoma drug is delivered at a substantially constant rate by comparison over the same time period.

The relative effectiveness of releasing the steroid and antiglaucoma drug simultaneously or at different times may depend on the steroid, the antiglaucoma drug, the patient, the formulation of the polymeric matrix of the implant, the configuration of the implant, or many other factors.

In an embodiment in which the antiglaucoma drug is released from the implant before the steroid is released from the implant, the antiglaucoma drug that is already present when the steroid is released may sometimes be more effective in counteracting any increase in intraocular pressure that may be induced by the release of the steroid than if the antiglaucoma drug were released after the steroid is released.

In an alternative embodiment in which the antiglaucoma drug is released from the implant at a later time than the steroid, some antiglaucoma drugs may be effective at rapidly reducing the increase in intraocular pressure that may be caused by the prior release of the steroid from the implant. For example, as previously discussed, carbonic anhydrase inhibitors can rapidly reduce the intraocular pressure. Releasing a carbonic anhydrase inhibitor antiglaucoma drug after releasing the steroid may sometimes be an effective treatment for ocular diseases.

The steroid and the antiglaucoma drug may also be released from the implant or implants continuously or intermittently. Continuous or intermittent release of the steroid and the antiglaucoma drug may both be effective.

For example, if the steroid and the antiglaucoma drug are released continuously, the continuous release of the antiglaucoma drug may mitigate any increase in the intraocular pressure that may be caused by the continuous release of the steroid.

In an embodiment in which the steroid and the antiglaucoma drug may be released intermittently, halting the release of the steroid may allow the intraocular pressure in the eye to decline to a lower pressure. Releasing the antiglaucoma drug from the implant after the ocular pressure has declined somewhat after the release of the steroid has been halted may sometimes enhance the effectiveness of the antiglaucoma drug in lowering the ocular pressure in the eye.

In another embodiment, the steroid may be released from the implant continuously, and the antiglaucoma drug may be released intermittently. An intermittent release of the antiglaucoma drug may optimize the reduction of the intraocular pressure that may have been increased by the release of the steroid.

In some embodiments, the steroid and the antiglaucoma drug may be released alternately. For example, a pulse of steroid may be followed by a pulse of antiglaucoma drug, followed in turn by another pulse of steroid.

In some instances, the concentration of steroid in the vitreous fluid may be at a higher level when an implant comprising steroid is first contacted with the vitreous fluid in the eye than at later times. The "spike" in the concentration of steroid in the vitreous fluid when the implant is first introduced into the eye could potentially lead to a corresponding spike in the ocular pressure in the eye. The spike in ocular pressure may increase the likelihood that a patient could develop glaucoma. It may therefore be advantageous to avoid high levels of steroid in the vitreous fluid of the patient when the implant is introduced into the eye of the patient.

Further, a patient may be more likely to develop glaucoma if the vitreous fluid of the patient continuously contains steroid for an extended period of time than if the vitreous fluid contains high levels of steroid for only a short period of time. The time that the steroid may be present in the vitreous fluid in the eye of the patient continuously without having the patient having an increased risk of developing glaucoma may vary from patient to patient. Generally, exposing the vitreous fluid in an eye of a patient to steroid continuously for approximately six months or more may lead to increased rates of glaucoma. It may therefore be advantageous to avoid continuously releasing steroid into the vitreous fluid for extended periods of time of, for example, six months or more.

The relative timing and the length of time of release of the steroid and the antiglaucoma drug may be varied, for example, by varying the formulation of the polymeric matrix and/or the configuration of the implant or implants. The following examples are illustrative only and are not meant to be limiting.

For example, the implant may comprise a first polymeric formulation associated with a steroid, where the first polymeric formulation may release the steroid at a relatively rapid rate. The implant may also comprise a second polymeric formulation that is associated with an antiglaucoma drug, where the second polymeric formulation may release the antiglaucoma drug at a slower rate than the rate at which the steroid is released from the first polymeric formulation. The slower rate of release of the antiglaucoma drug from the second polymeric formulation may provide a longer period of time of protection in which the intraocular pressure may be lowered by the presence of the antiglaucoma drug.

In another embodiment, the implant may comprise a steroid in an exterior portion of the polymeric formulation and an antiglaucoma drug in an interior portion of the polymeric formulation. The steroid in the exterior, portion of the polymer may be released quickly, and the antiglaucoma drug on the interior portion of the polymer may be released at a later time. Releasing the antiglaucoma drug after the steroid is released may aid in lowering any increase in intraocular pressure due to release of the steroid.

The implant may be configured to release steroid and antiglaucoma drug alternately in different ways. For example, an ocular implant may comprise alternating layers of steroid and antiglaucoma drug such that the steroid and the antiglaucoma drug may be released from the implant on an alternating basis.

The polymeric formulation or configuration of the implant comprising steroid may also be designed to avoid high initial levels of steroid in the vitreous fluid. For example, the polymer of the implant may be designed to have small pores. The small pores may slow the release of the steroid from the implant, mitigating the "spike" in the initial steroid concentration. In an alternative embodiment, the implant may comprise an impermeable coating having a plurality of holes in the coating, where the size of the plurality of holes may be relatively small. Other ways to avoid high initial levels of steroid will be apparent to those skilled in the art.

The manner and timing of the release of the steroid and the antiglaucoma drug (or auxiliary agent) may therefore be optimized by changing the formulation of the polymeric matrix and/or the configuration of the implant or implants. The optimal configurations and formulations for the implant or implants may depend on the quantities and types of the steroid and the antiglaucoma drug.

A method for treating ocular diseases in a patient comprises contacting an implant comprising a steroid and an implant comprising an antiglaucoma drug with the vitreous fluid in the eye of the patient. The implant comprising the antiglaucoma drug may be the same or different than the implant comprising the steroid. Contacting the implant comprising the steroid with the vitreous fluid may release a therapeutic amount of steroid into the vitreous fluid. Contacting the implant comprising the antiglaucoma drug with the vitreous fluid may release a therapeutic amount of antiglaucoma drug into the vitreous fluid.

Releasing the steroid into the vitreous fluid may sometimes increase the intraocular pressure in the eye of the patient. An increase in the intraocular pressure could increase the likelihood of the patient developing complications such as glaucoma.

Releasing antiglaucoma drug into the vitreous fluid from the implant comprising the antiglaucoma drug may lessen any increase in intraocular pressure that may be caused by releasing the steroid into the vitreous fluid.

The method may further comprise providing implants or mixtures of implants having configurations and formulations as previously described.

EXAMPLES

The following non-limiting examples provide those of ordinary skill in the art with specific preferred drug delivery systems, methods of making such systems, and methods to treat conditions within the scope of the present invention. The following examples are not intended to limit the scope of the invention.

Example 1

Manufacture and Testing of Implants Containing Flucinolone and a Biodegradable Polymer Matrix Fluocinolone acetonide was combined with a polymer in a stainless steel mortar and mixed using the Turbula shaker set at 96 RPM for 15 minutes. The powder of the fluocinolone and polymer was scraped off the walls of the steel mortar and then mixed again for an additional 15 minutes. The powder blend was heated at temperatures ranging from 110° C. to 160° C., depending on the polymer used, for a total of 30 minutes, forming a polymer/drug melt. The melt was pelletized, then loaded into the barrel and extruded into filaments, and finally the filaments were cut into about 0.5 mg or about 1 mg size implants. The implants had a weight range from about 450 µg to about 550 µg, or from about 900 µg to about 1100 µg. The 1 mg size implants had a length of about 2 mm and a diameter of about 0.72 mm.

Each implant was placed in a 20 ml screw cap vial with 10 ml of 0.9% saline. The vials were placed in a shaking water bath at 37° C. 9 ml aliquots were removed and replaced with equal volume of fresh media on day 1, 4, 7 and every week thereafter. The in-vitro release testing was performed on each lot of implants in six replicates.

The drug assays were performed by HPLC, consisting of a Waters 2690 Separation Module (or 2696) and Waters 2996 Photodiode Array Detector. A Varian Microsorb-MV™ 100 Å C18 column was used for separation and the detector was set at 254 nm. The mobile phase was (50:50) acetonitrile/0.005M sodium acetate (pH=4.0). The flow rate was 1.00 ml/min and the total run time for was 6 minutes. The release rate was determined by calculating the amount of drug released in a given volume of medium over time in µg/day.

A total of 20 fluocinolone acetonide formulations were prepared, as shown in Table 1. The polymers used were Boehringer Ingelheim Resomers RG755, RG503, R202H, RG502H, and RG502. The inherent viscosities were about 0.6, 0.4, 0.2, 0.2, and 0.2 dl/g, respectively. The average molecular weights were 40000, 28300, 6500, 8400, and 11400 daltons, respectively.

TABLE 1

| Formulation | Lot | FA (w/w) | Polymer | I.V. (dl/g) | Melt T | Extru T (core) | Nozzle | DDS Size |
|---|---|---|---|---|---|---|---|---|
| 1 | 453-98A | 40% | RG755 | 0.6 | 160° C. | 122° C. | 380 μm | 0.5 mg |
| 2 | 453-98B | 40% | RG755 | 0.6 | 160° C. | 122° C. | 720 μm | 0.5 mg |
| 3 | 453-99 | 20% | RG755 | 0.6 | 160° C. | 116° C. | 720 μm | 1 mg |
| 4 | 453-100 | 40% | RG503 | 0.4 | 150° C. | 116° C. | 720 μm | 0.5 mg |
| 5 | 453-101 | 20% | RG503 | 0.4 | 150° C. | 106° C. | 720 μm | 1 mg |
| 6 | 453-116 | 40% | R202H | 0.2 | 110° C. | 90° C. | 720 μm | 0.5 mg |
| 7 | 453-117 | 40% | RG752 | 0.2 | 110° C. | 90° C. | 720 μm | 0.5 mg |
| 8 | 453-118 | 40% | RG502H | 0.2 | 110° C. | 84° C. | 720 μm | 0.5 mg |
| 9 | 453-119 | 40% | RG502 | 0.2 | 110° C. | 92° C. | 720 μm | 0.5 mg |
| 10 | 453-120 | 40% | (1:1) RG502H/R202H | 0.2 | 110° C. | 85° C. | 720 μm | 0.5 mg |
| 11 | 453-121 | 40% | (1:1) RG502H/RG752 | 0.2 | 110° C. | 83° C. | 720 μm | 0.5 mg |
| 12 | 453-128 | 60% | (3:1) RG502H/R202H | 0.2 | 110° C. | 95° C. | 720 μm | 0.5 mg |
| 13 | 453-129 | 60% | (3:1) RG502H/RG752 | 0.2 | 110° C. | 101° C. | 720 μm | 0.5 mg |
| 14 | 453-130 | 60% | (3:1) RG502H/RG502 | 0.2 | 110° C. | 101° C. | 720 μm | 0.5 mg |
| 15 | 453-131 | 60% | (1:1) RG502H/R202H | 0.2 | 110° C. | 101° C. | 720 μm | 0.5 mg |
| 16 | 453-137 | 40% | (1:2) RG502H/R202H | 0.2 | 110° C. | 88° C. | 720 μm | 1 mg |
| 17 | 453-138 | 40% | (1:2) RG502H/RG752 | 0.2 | 110° C. | 85° C. | 720 μm | 1 mg |
| 18 | 453-139 | 40% | (1:2) RG502H/RG502 | 0.2 | 120° C. | 85° C. | 720 μm | 1 mg |
| 19 | 453-140 | 40% | (1:2) RG502H/RG503 | n.a. | 120° C. | 99° C. | 720 μm | 1 mg |
| 20 | 453-141 | 40% | (1:2) RG502H/RG755 | n.a. | 120° C. | 99° C. | 720 μm | 1 mg |

FA = Fluocinolone Acetonide
I.V. = inherent viscosity
Melt T = melting temperature
Extru T = extrusion temperature
Nozzle = nozzle diameter (μm)
DDS size = drug delivery system size (i.e., the weight of an individual implant)

Figure 1:
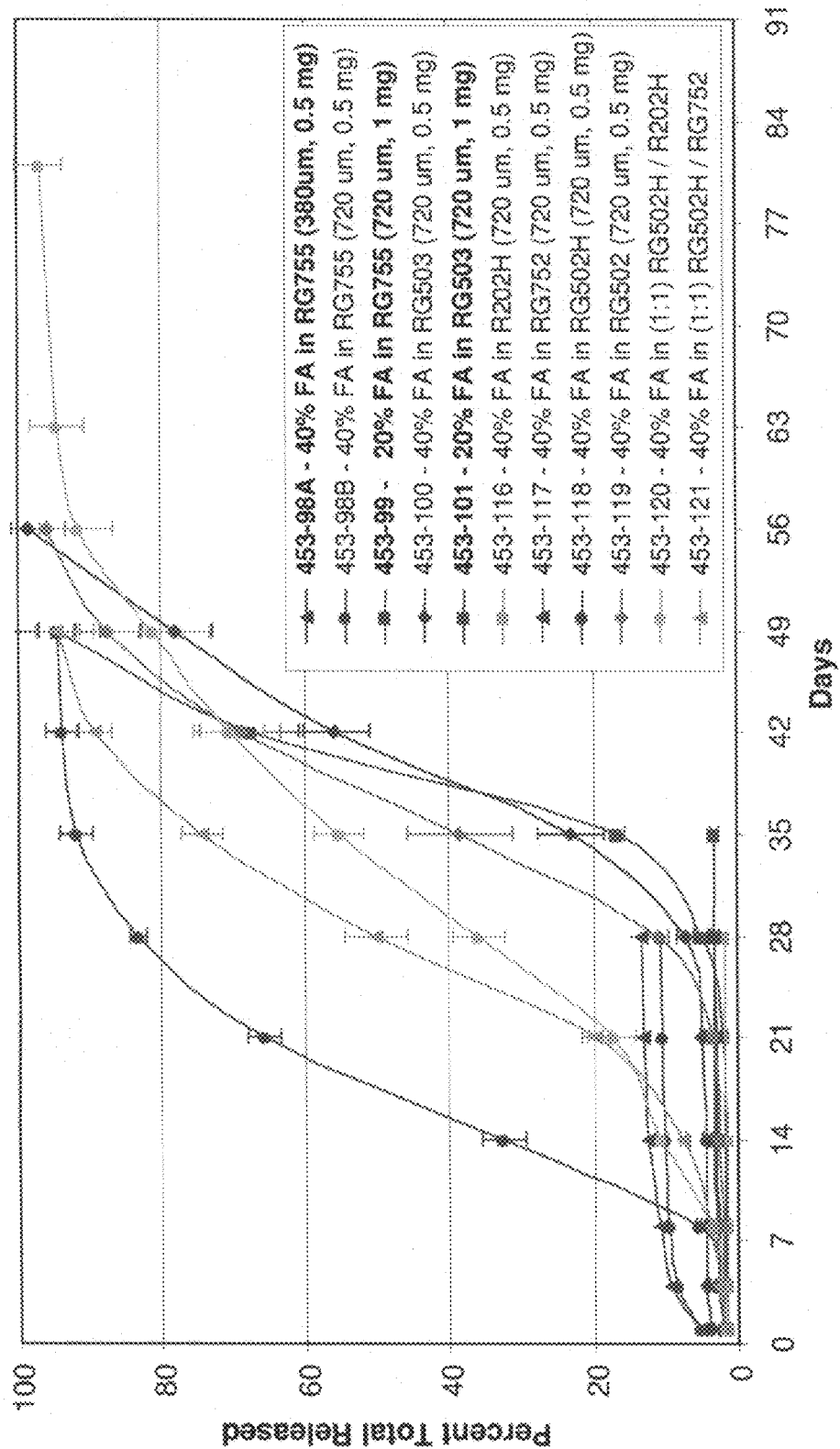
FIG. 1 is a graph showing the cumulative release profiles for biodegradable fluocinolone acetonide containing implants as determined in 0.9% saline at 37 degrees Celsius.
Figure 2:
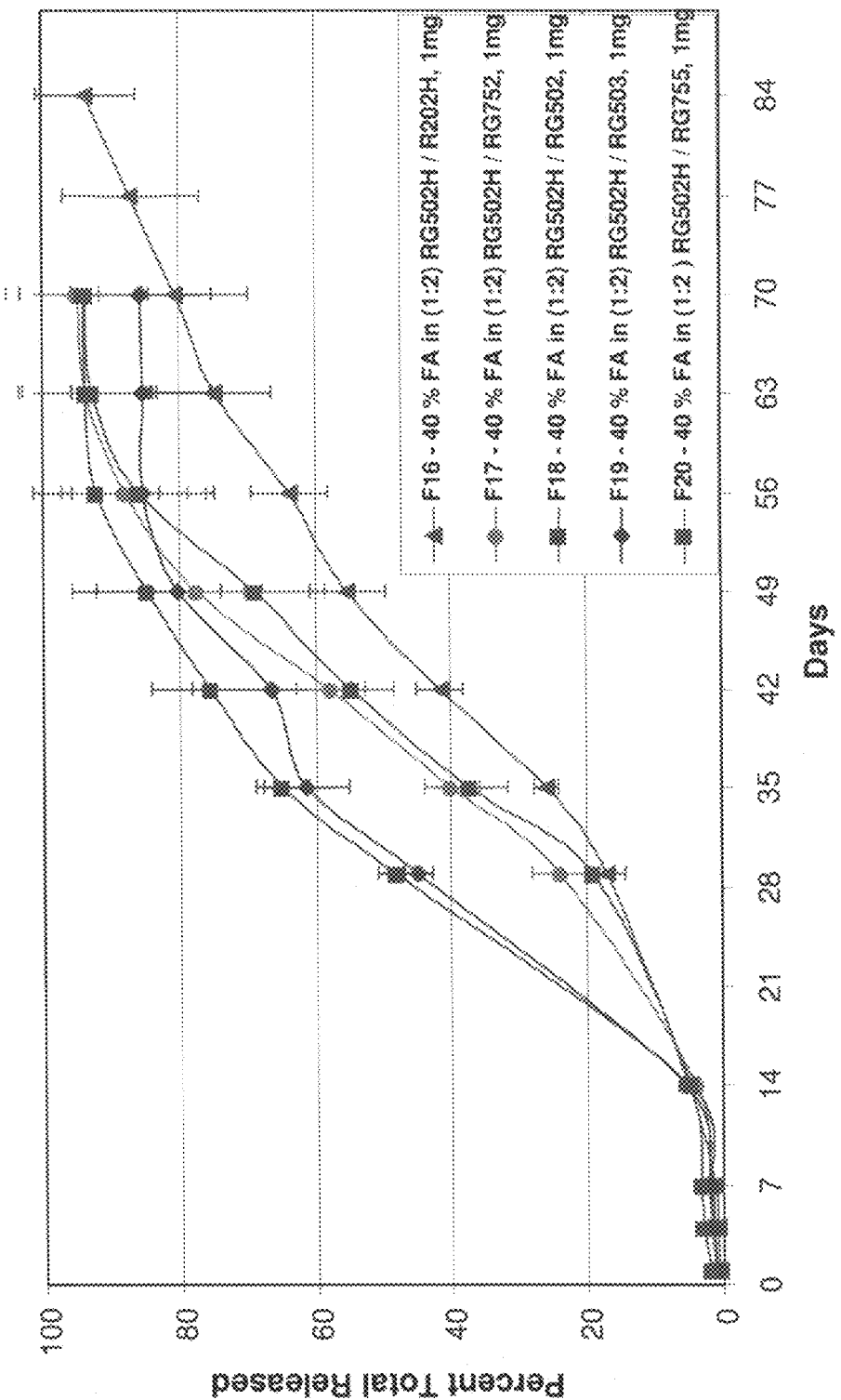
FIG. 2 is a graph similar to FIG. 1 showing the cumulative release profiles for biodegradable fluocinolone acetonide containing implants with different combinations of biodegradable polymers.

Of the 20 formulations prepared, 16 were screened for release testing (formulations #1-11 and 16-20). Initially, the release medium was 10 mL phosphate buffer-saline (PBS) with 1 mL replacement at each time point, but almost no release was observed up to three weeks. The release medium was subsequently changed to PBS with 9 mL replacement, but the release was inconsistent and with unacceptably high standard deviations. Finally, the release medium was switched to 0.9% saline with 9 mL replacement at each time point. The release profiles are shown in FIGS. 1 and 2.

Most of the fluocinolone acetonide formulations released the total drug load in approximately 2-3 months. Of the 16 formulations, 11 formulations exhibited release for about two months. Of the 11 formulations, 6 formulations exhibited release for about three months.

In particular, all formulations prepared with Resomer RG755 (453-98A, 453-98B, and 453-99) and RG752 (453-117) showed almost no release after day 4 and their release studies were stopped after 1 month.

Formulations prepared with RG503 (453-100 and 453-101) and RG502 (453-119) showed a delay of 3-4 weeks before releasing 100% between day 49 and day 56.

The formulation prepared with RG502H (453-118) appeared to be the fastest, on day 49.

The formulation prepared with a (1:1) mixture of RG502H and R202H led to the longest release, up to 84 days.

Finally, the formulation prepared with a (1:1) mixture of RG502H and RG752 appeared to be slower than the one prepared with RG502H (453-118) at first, but eventually ended up having complete release at day 49.

Based on these data, it was concluded that a mixture of RG502H and other polymers with slower release will provide a formulation with longer release and relatively closer to zero-order kinetics. One formulation with desirable release properties was a 1:2 mixture of RG502H and R202H, which led to a release of 94% of the fluocinolone after 84 days.

Example 2

Manufacture and Testing of Implants Containing Triamcinolone and a Biodegradable Polymer Matrix Triamcinolone acetonide was combined with a polymer in a stainless steel mortar and mixed using the Turbula shaker set at 96 RPM for 15 minutes. The powder of the fluocinolone and polymer was scraped off the walls of the steel mortar and then mixed again for an additional 15 minutes. The powder blend was heated at temperatures ranging from 110° C. to 160° C., depending on the polymer used, for a total of 30 minutes, forming a polymer/drug melt. The melt was pelletized, then loaded into the barrel and extruded into filaments, and finally the filaments were cut into about 0.5 mg or about 1 mg size implants. The implants had a weight range from about 450 μg to about 550 μg, or from about 900 μg to about 1100 μg. The 1 mg size implants had a length of about 2 mm and a diameter of about 0.72 mm.

The testing of the triamcinolone implants was performed as described in Example 1.

A total of 16 triamcinolone acetonide formulations were prepared, as shown in Table 2. The polymers used were. Boehringer Ingelheim Resomers RG755, RG503, R202H, RG502H, and RG502. The inherent viscosities were 0.6, 0.4, 0.2, 0.2, and 0.2 dl/g, respectively. The average molecular weights were 40000, 28300, 6500, 8400, and 11400 daltons, respectively.

TABLE 2

Triamcinolone Acetonide Formulations

| Formulation | Lot | TA (w/w) | Polymer | I.V. (dl/g) | Melt T | Extru T (core) | Nozzle | DDS Size |
|---|---|---|---|---|---|---|---|---|
| 1 | 453-96 | 50% | RG755 | 0.6 | 160° C. | 122° C. | 720 µm | 1 mg |
| 2 | 453-97 | 50% | RG503 | 0.4 | 150° C. | 116° C. | 720 µm | 1 mg |
| 3 | 453-112 | 50% | RG502 | 0.2 | 110° C. | 105° C. | 720 µm | 1 mg |
| 4 | 453-113 | 50% | RG502H | 0.2 | 110° C. | 90° C. | 720 µm | 1 mg |
| 5 | 453-114 | 50% | RG752 | 0.2 | 110° C. | 95° C. | 720 µm | 1 mg |
| 6 | 453-115 | 50% | R202H | 0.2 | 110° C. | 96° C. | 720 µm | 1 mg |
| 7 | 453-122 | 50% | (1:1) RG502H/RG752 | 0.2 | 110° C. | 83° C. | 720 µm | 1 mg |
| 8 | 453-123 | 50% | (1:1) RG502H/R202H | 0.2 | 110° C. | 85° C. | 720 µm | 1 mg |
| 9 | 453-125 | 60% | (3:1) RG502H/RG502 | 0.2 | 110° C. | 92° C. | 720 µm | 1 mg |
| 10 | 453-126 | 60% | (3:1) RG502H/R202H | 0.2 | 110° C. | 92° C. | 720 µm | 1 mg |
| 11 | 453-127 | 60% | (3:1) RG502H/RG752 | 0.2 | 110° C. | 95° C. | 720 µm | 1 mg |
| 12 | 453-132 | 60% | (1:1) RG502H/R202H | 0.2 | 110° C. | 108° C. | 720 µm | 1 mg |
| 13 | 453-133 | 50% | (1:1) RG502H/RG502 | 0.2 | 110° C. | 99° C. | 720 µm | 1 mg |
| 14 | 453-134 | 50% | (1:1) RG502H/RG755 | N/A | 110° C. | 110° C. | 720 µm | 1 mg |
| 15 | 453-135 | 50% | (1:1) RG502H/RG503 | N/A | 110° C. | 110° C. | 720 µm | 1 mg |
| 16 | 453-136 | 50% | (3:1) RG502H/RG502 | 0.2 | 110° C. | 88° C. | 720 µm | 1 mg |

TA = Triamcinolone Acetonide
I.V. = inherent viscosity
Melt T = melting temperature
Extru T = extrusion temperature
Nozzle = nozzle diameter (µm)
DDS size = drug delivery system size (i.e., the weight of an individual implant)

Figure 3:
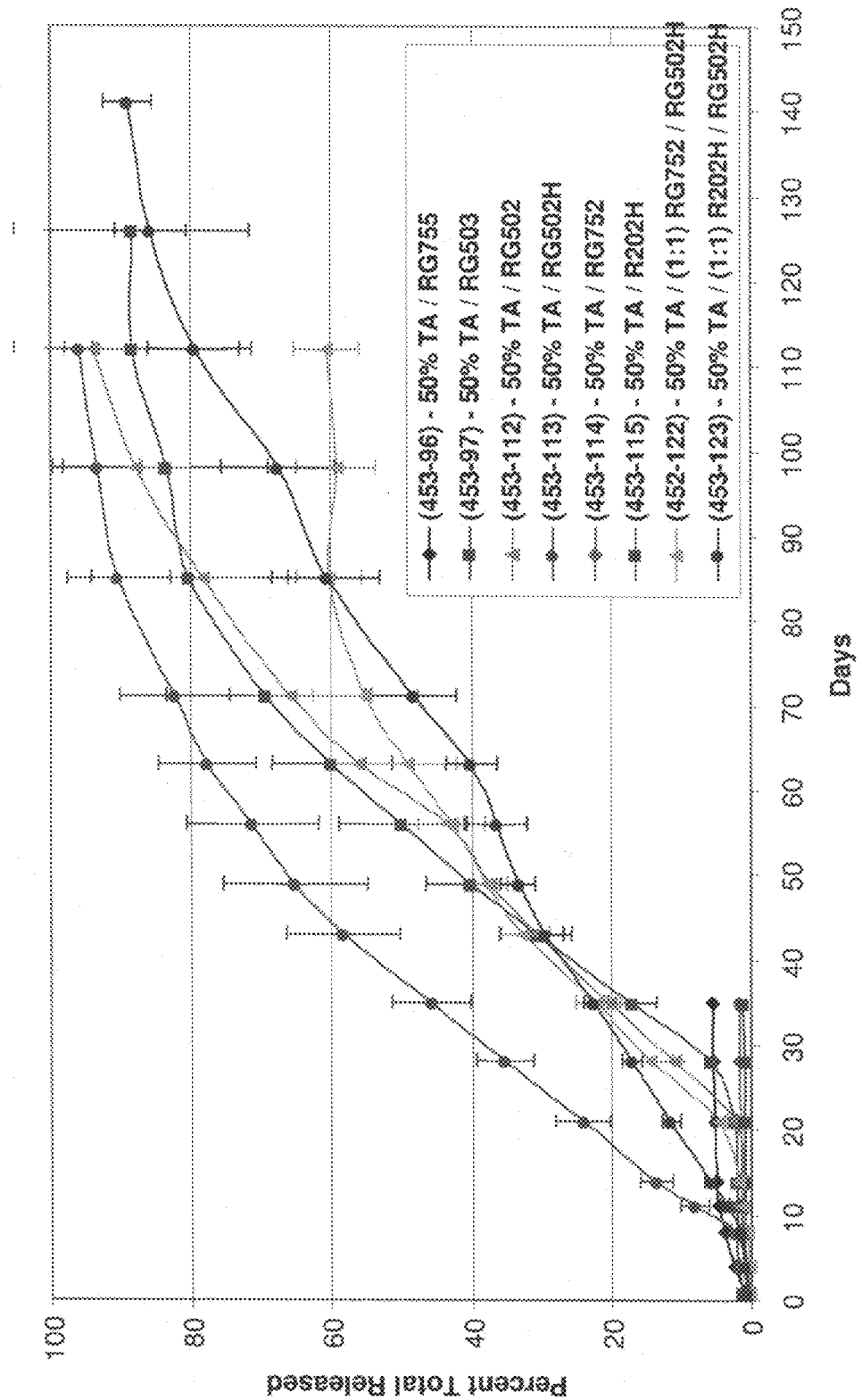
FIG. 3 is a graph similar to FIG. 1 showing the cumulative release profiles for biodegradable triamcinolone acetonide containing implants.
Figure 4:
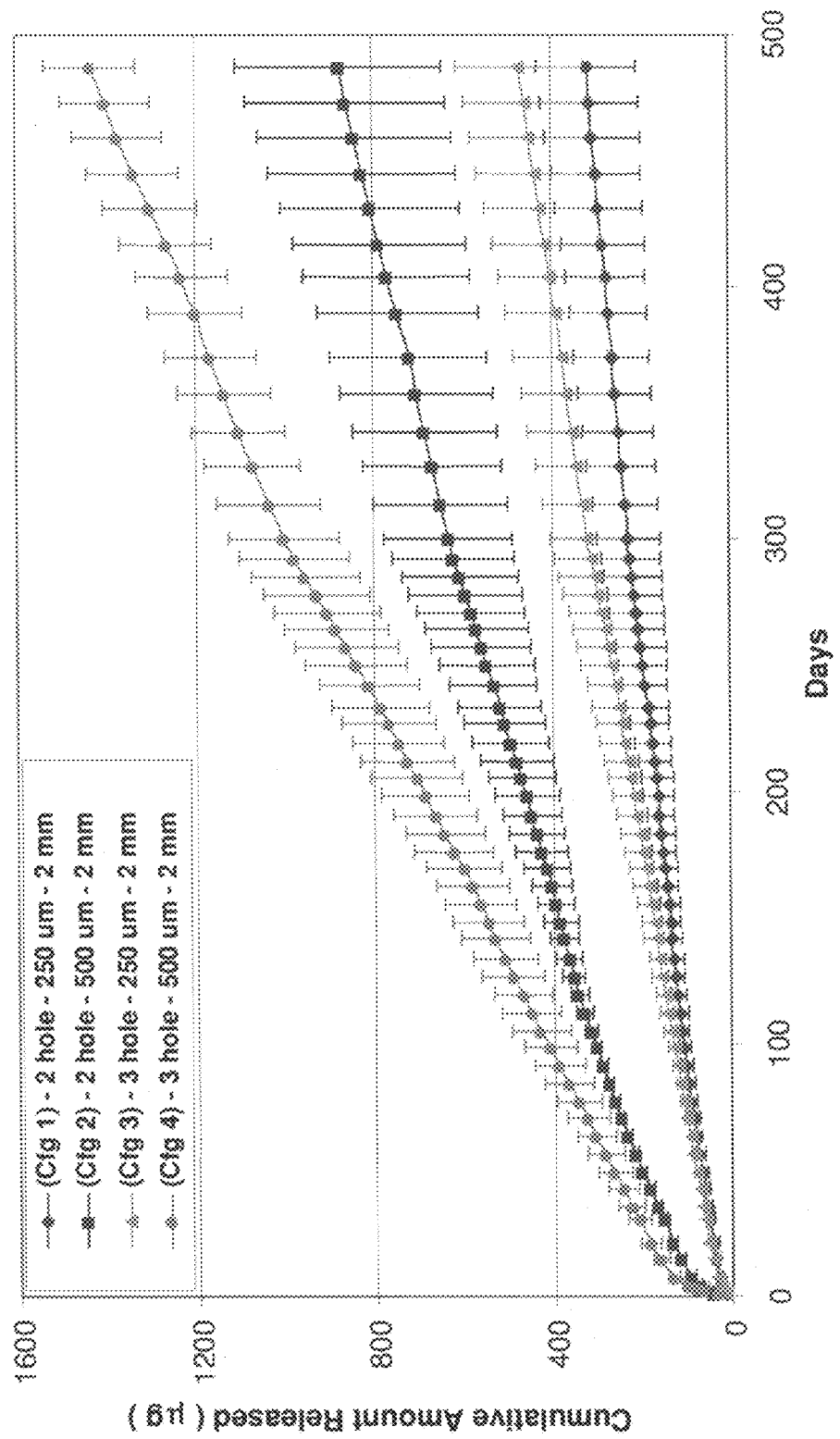
FIG. 4 is a graph showing the cumulative release profiles for non-sterile fluocinolone acetonide containing implants having different hole configurations.
Figure 5:
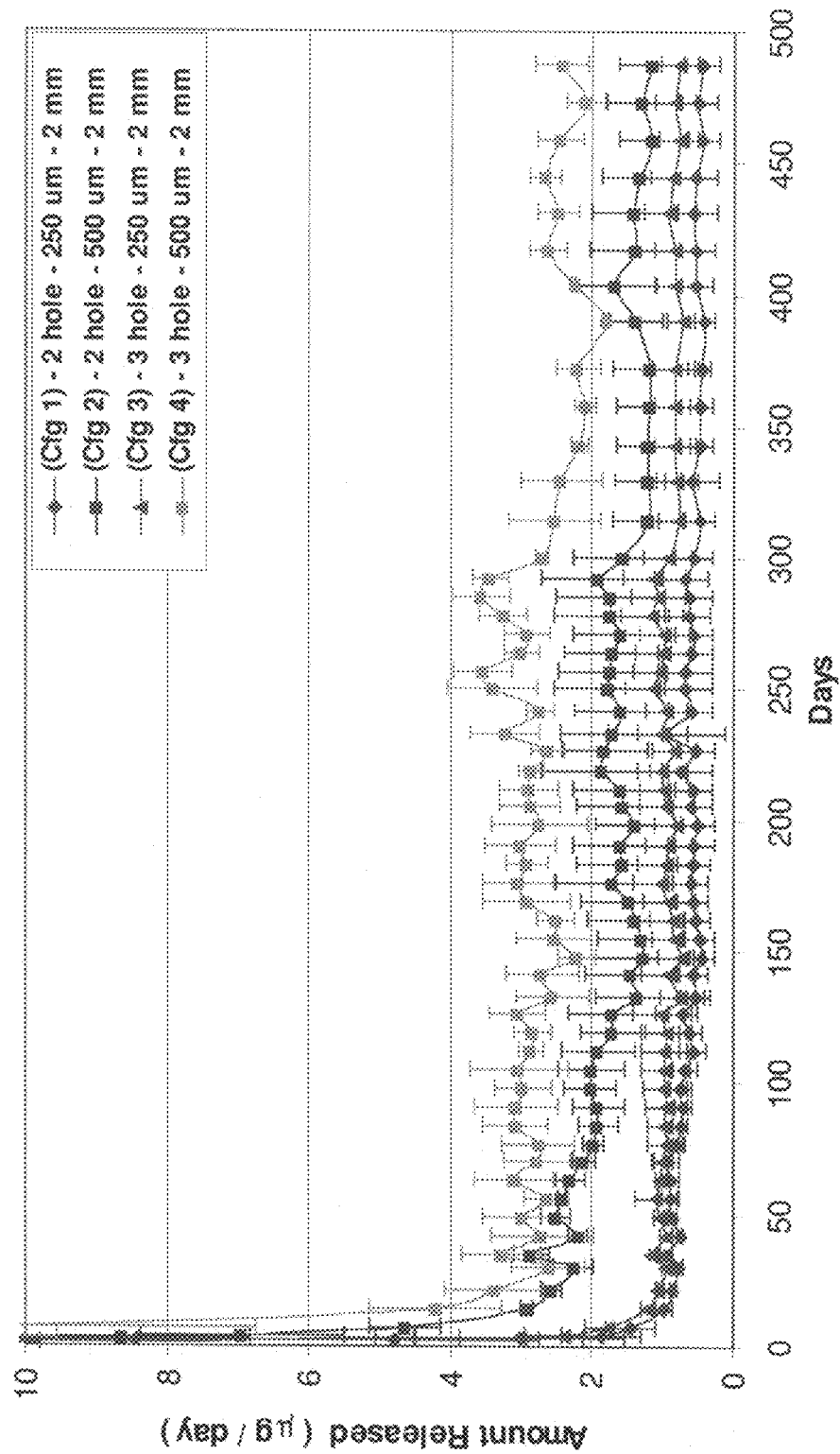
FIG. 5 is a graph showing the amount of fluocinolone released per day for the implants described in FIG. 4.
Figure 6:
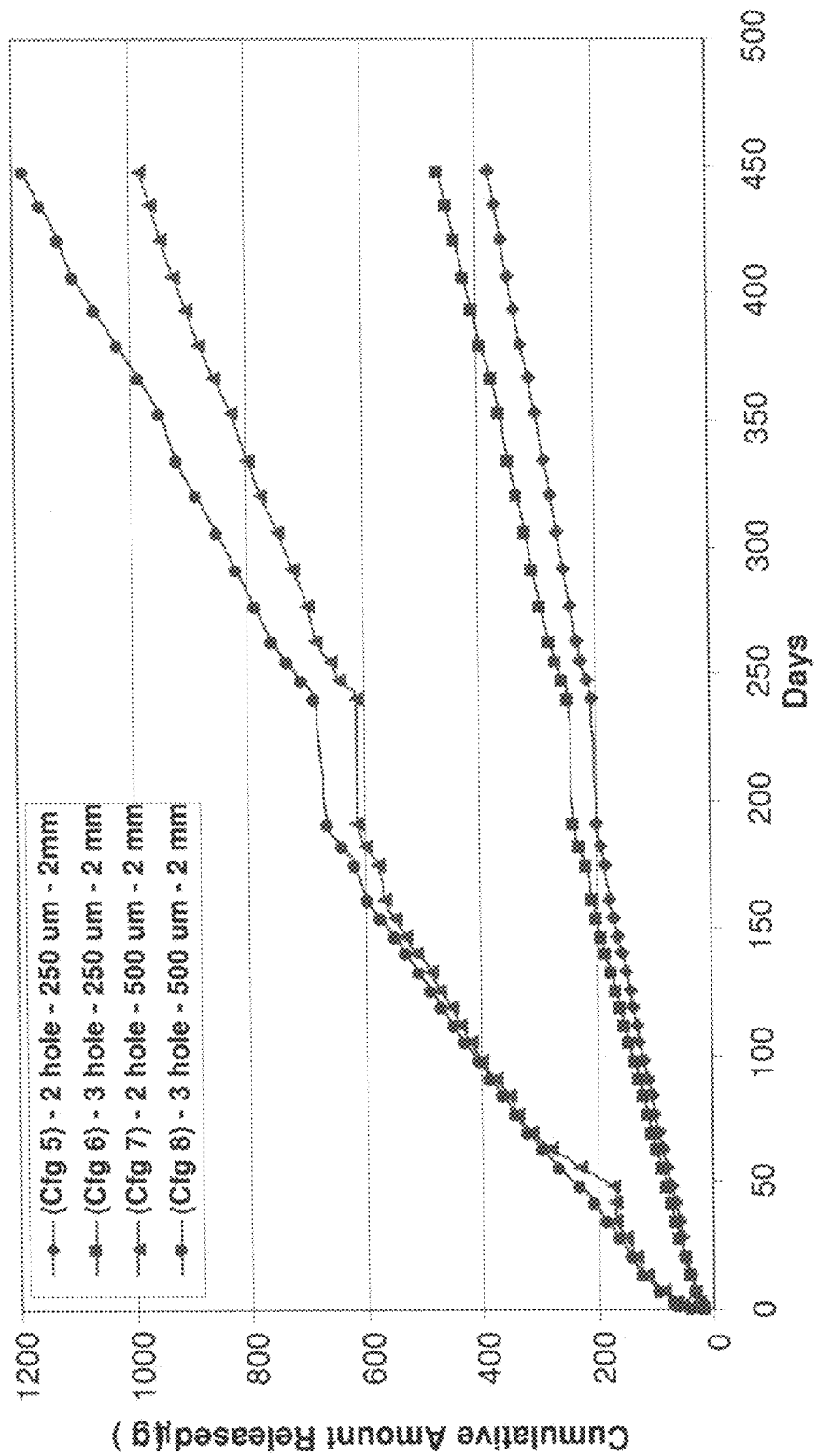
FIG. 6 is a graph showing the cumulative release profiles for sterile fluocinolone acetonide containing implants having different hole configurations.
Figure 7:
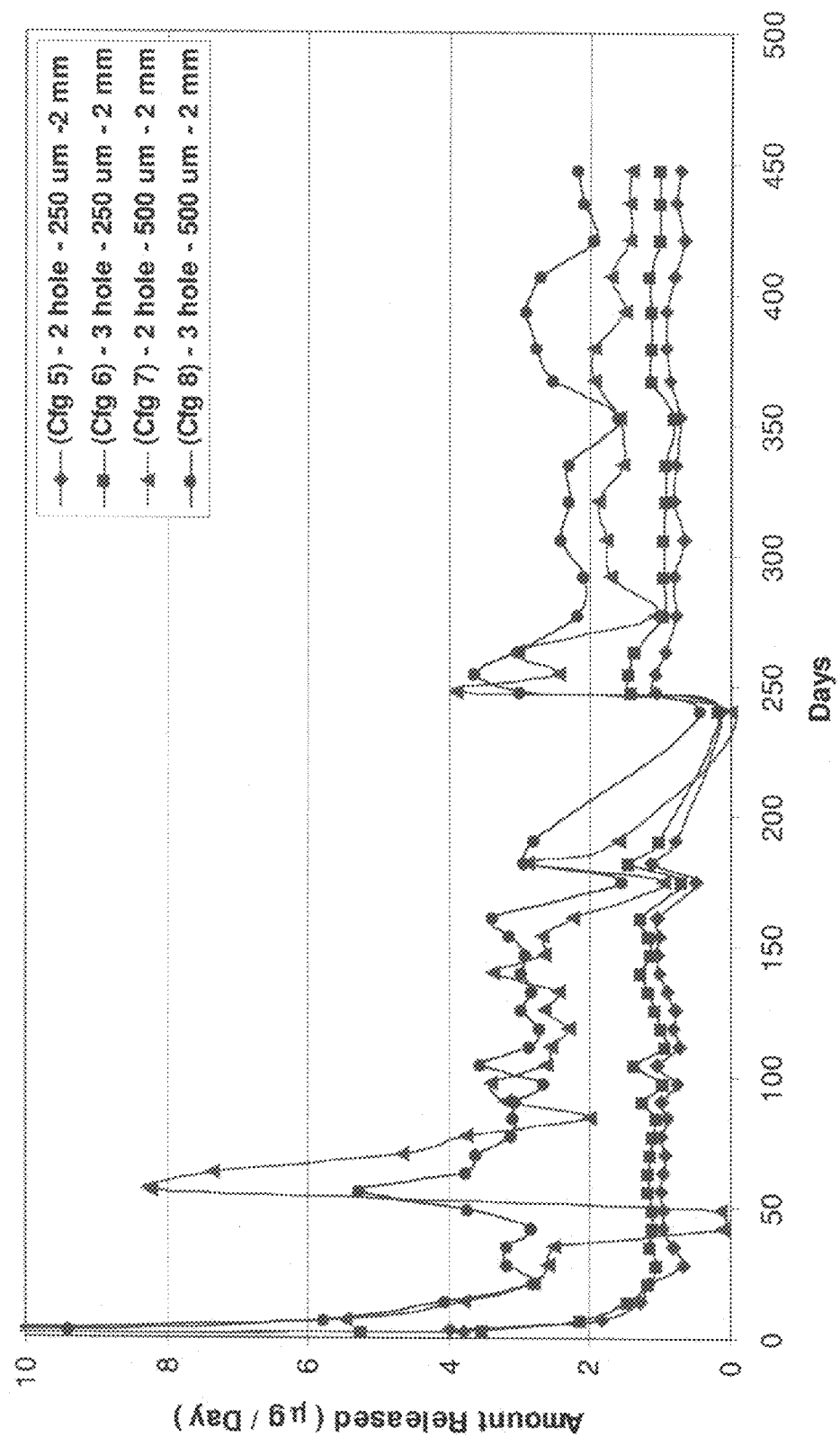
FIG. 7 is a graph showing the amount of fluocinolone released per day for the implants described in FIG. 6.
Figure 8:
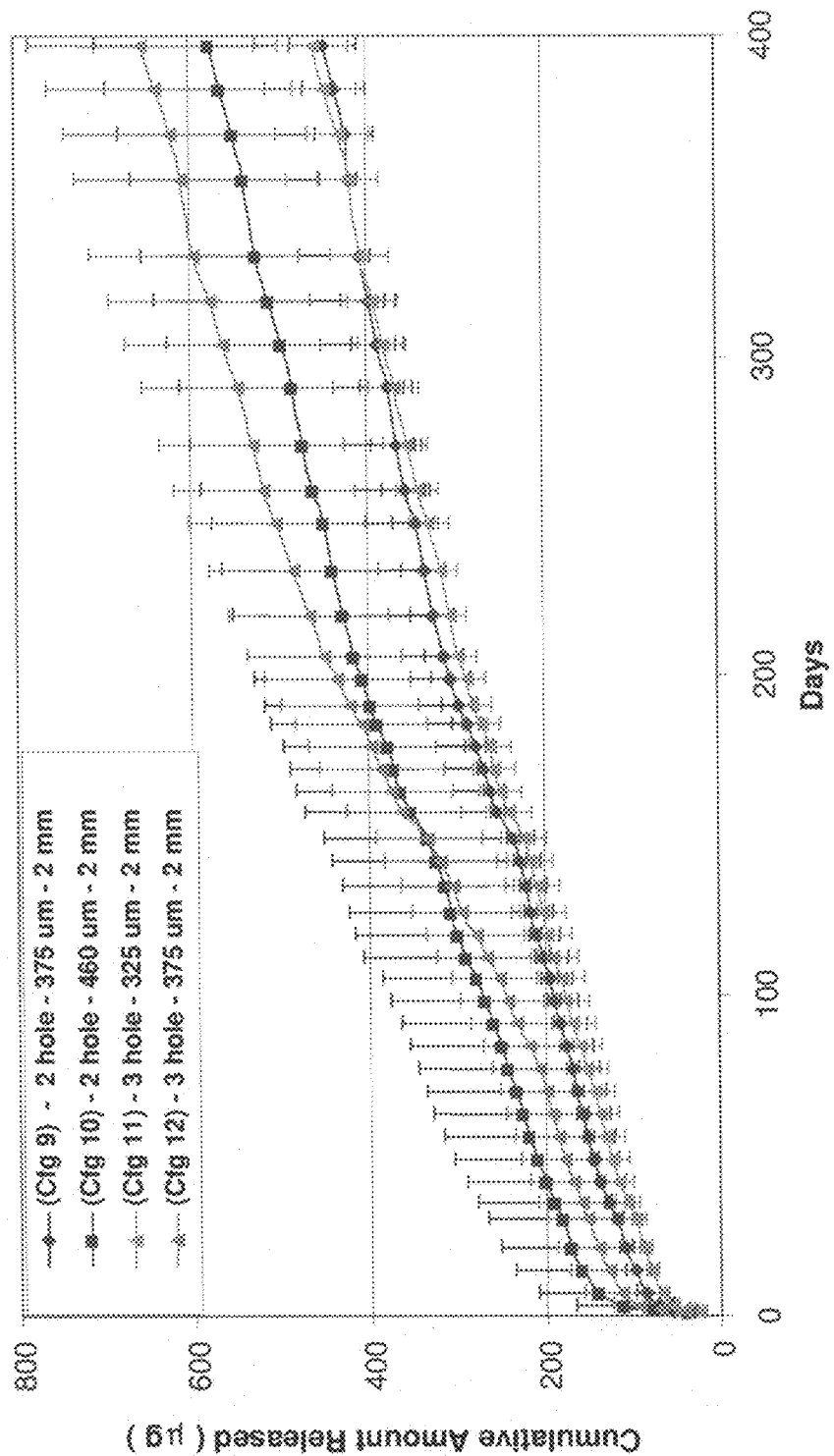
FIG. 8 is a graph showing the cumulative release profiles for non-sterile fluocinolone acetonide containing implants having different hole configurations than those described in FIG. 4.
Figure 9:
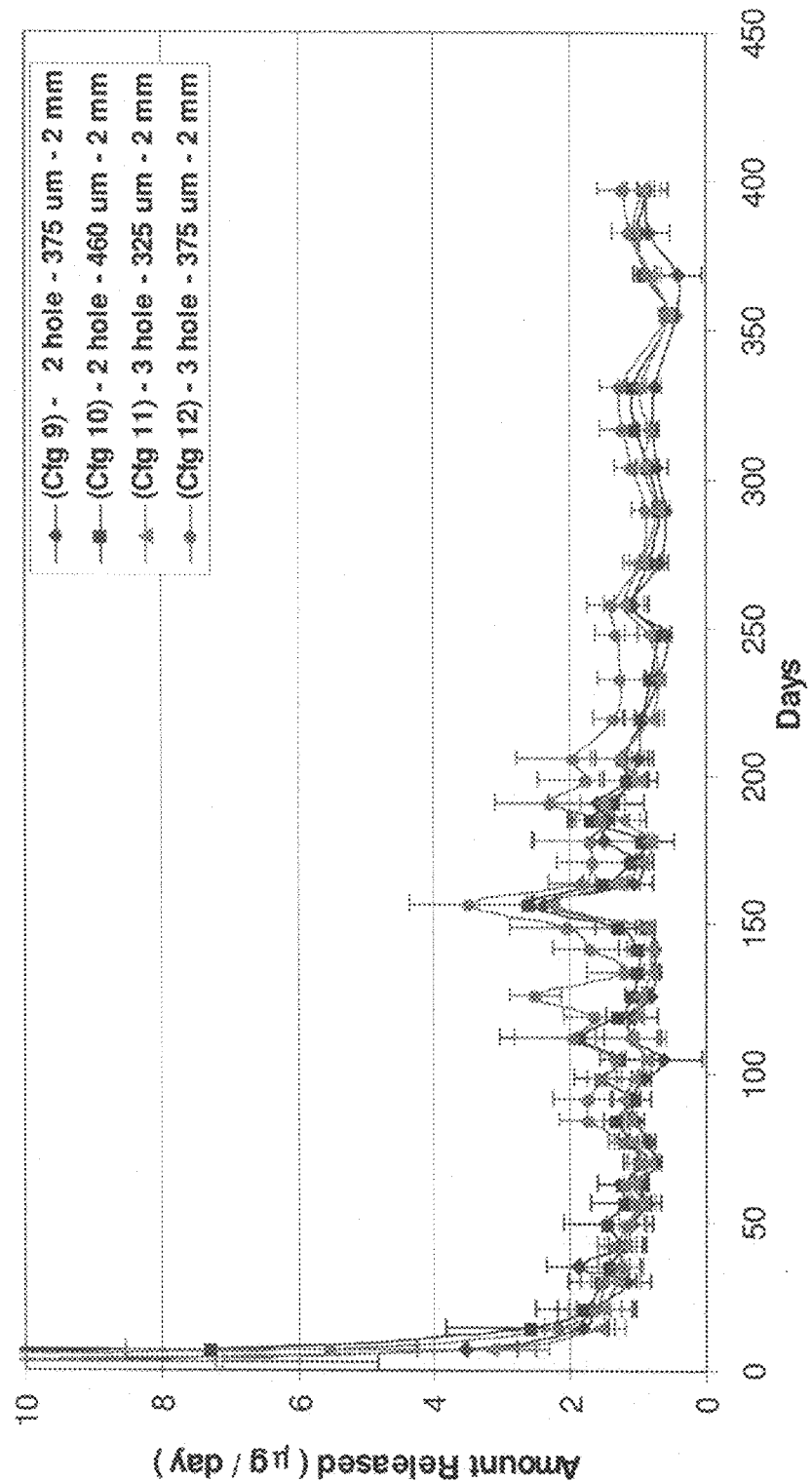
FIG. 9 is a graph showing the amount of fluocinolone released per day for the implants described in FIG. 8.
Figure 10:
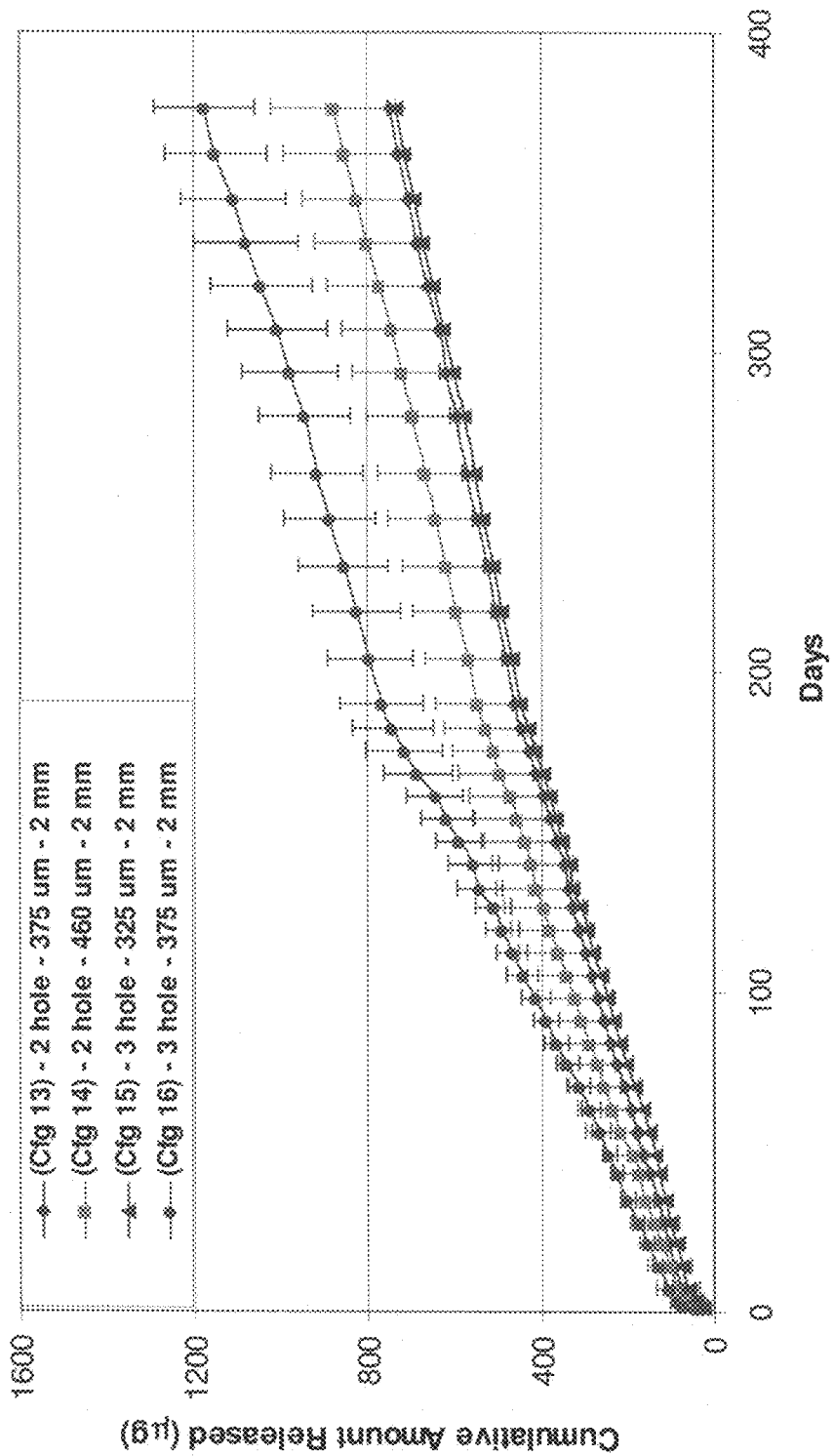
FIG. 10 is a graph showing the cumulative release profiles for sterile fluocinolone acetonide containing implants having hole configurations similar to those described in FIG. 8.
Figure 11:
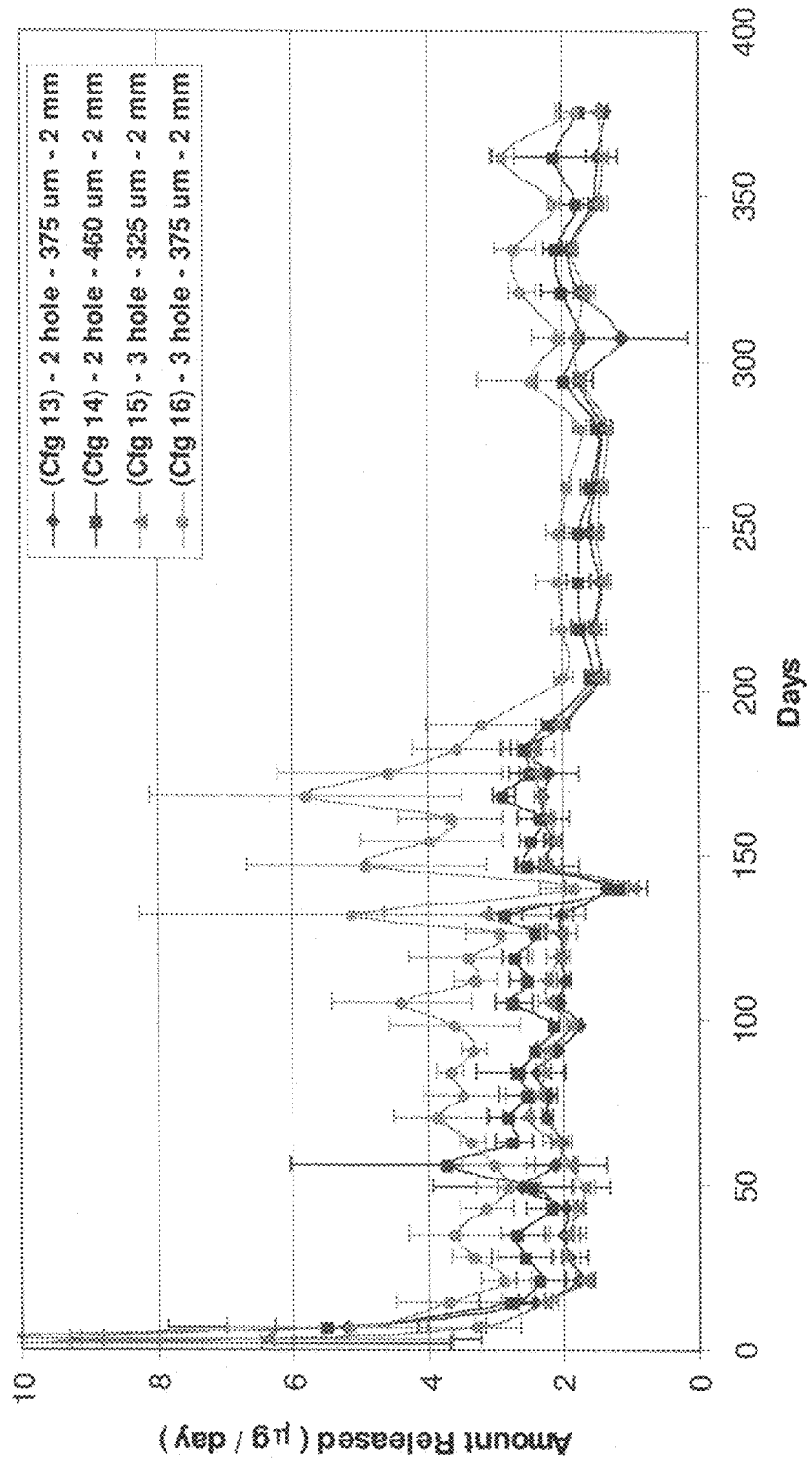
FIG. 11 is a graph showing the amount of fluocinolone released per day for the implants described in FIG. 10.

Of the 16 formulations prepared, 8 were screened for release testing (formulations #1-8). The same problem was encountered with the release medium as that of fluocinolone. The release medium was switched to 0.9% saline with 9 mL replacement at each time point. The release profiles are shown in FIG. 3.

Certain triamcinolone acetonide formulations had release periods of about 4-6 months. Of the eight formulations, five formulations exhibited 4 or more months of release, and two formulations exhibited release for more than 5 months.

Formulations prepared with RG755 (453-96), RG752 (453-114) and R202H (453-115) showed essentially zero to very slow release.

The formulation prepared with RG502H (453-113) had the fastest and perhaps smoothest release profile with minimal delay lasting close to 4 months.

The formulation prepared with RG502 (453-112) showed an equally fast release of 4 months, but there was a 2-3 weeks lag time.

The formulation prepared with RG503 (453-97) showed a release longer than 4 months, but it also had 4 weeks lag time.

Similar to the formulations in Example 1, the formulation prepared with a (1:1) mixture of RG502H and R202H lot (453-123) led to a desirable release profile approaching 5 to 6 months. This release profile was the most linear and the longest (>140 days).

Based on the data of Examples 1 and 2, polymer blends appeared to achieve a more desired controlled release rate relative to single polymers. Using a slow degrading poly(D,L-lactide), such as R202H, and mixing it with a fast degrading poly(D,L-lactide-co-glycolide), such as RG502H, is effective in controlling the release rate of both fluocinolone and triamcinolone acetonide.

Example 3

Manufacture and In Vitro Testing of Implants Containing Fluocinolone and a Polymeric Coating Silicone tubing (Specialty Silicone Fabricators, Inc, SSF-METN-755, P.N. OP-2) was cut to either 10 mm or 7 mm tubes to form an implant element. Holes of various sizes were drilled (Photomachining, Inc) in the cut tubes. The configuration of each tube was characterized by the number of holes, the diameter of holes and the distance between the holes, as well as the tube length and the sterility of the tube. Each drilled tube was glued on one end with silicone adhesive (Nusil Silicone Technology, MED-1511), and dried for 72 hours at ambient temperature and then packed with fluocinolone acetonide. Each of the 10 mm long tube contained 4 to 5 mg of fluocinolone, while each of the 7 mm long tubes contained 2 to 3 mg of fluocinolone. Finally, the other end of each tube was glued and dried for 72 hours. The implants did not include any additional excipients or release modifiers. A total of 30 different tube configurations were tested and are described in Table 3.

TABLE 3

Fluocinolone Reservoir Delivery Technology Configurations

| Configuration | Lot # | # Hole/Diam/Distance | Average Drug Load (µg) | Before or After γSterilization | Tube Length | Number of Replicates |
|---|---|---|---|---|---|---|
| 1 | 257-172-1 | 2 hole - 250 µm - 2 mm | 4526 (n = 3) | BS | 1 cm | 3 |
| 2 | 257-172-4 | 2 hole - 500 µm - 2 mm | 4667 (n = 3) | BS | 1 cm | 3 |
| 3 | 257-172-7 | 3 hole - 250 µm - 2 mm | 4508 (n = 3) | BS | 1 cm | 3 |
| 4 | 257-172-10 | 3 hole - 500 µm - 2 mm | 4437 (n = 3) | BS | 1 cm | 3 |
| 5 | 267-33-1 | 2 hole - 250 µm - 2 mm | 4699 (n = 1) | AS | 1 cm | 1 |
| 6 | 267-33-2 | 3 hole - 250 µm - 2 mm | 4536 (n = 1) | AS | 1 cm | 1 |
| 7 | 267-33-3 | 2 hole - 500 µm - 2 mm | 4457 (n = 1) | AS | 1 cm | 1 |
| 8 | 267-33-4 | 3 hole - 500 µm - 2 mm | 4214 (n = 1) | AS | 1 cm | 1 |

TABLE 3-continued

Fluocinolone Reservoir Delivery Technology Configurations

| Configuration | Lot # | # Hole/Diam/Distance | Average Drug Load (μg) | Before or After γSterilization | Tube Length | Number of Replicates |
|---|---|---|---|---|---|---|
| 9 | 267-140 | 2 hole - 375 μm - 2 mm | 5228 (n = 3) | BS | 1 cm | 3 |
| 10 | 267-140 | 2 hole - 460 μm - 2 mm | 4466 (n = 3) | BS | 1 cm | 3 |
| 11 | 267-140 | 3 hole - 325 μm - 2 mm | 4867 (n = 3) | BS | 1 cm | 3 |
| 12 | 267-140 | 3 hole - 375 μm - 2 mm | 4566 (n = 3) | BS | 1 cm | 3 |
| 13 | 285-1AS | 2 hole - 375 μm - 2 mm | 4663 (n = 3) | AS | 1 cm | 3 |
| 14 | 285-1AS | 2 hole - 460 μm - 2 mm | 4806 (n = 3) | AS | 1 cm | 3 |
| 15 | 285-1AS | 3 hole - 325 μm - 2 mm | 5168 (n = 3) | AS | 1 cm | 3 |
| 16 | 285-1AS | 3 hole - 375 μm - 2 mm | 4981 (n = 3) | AS | 1 cm | 3 |
| 17 | 285-54 | 2 hole - 250 μm - 2 mm | 2804 (n = 3) | AS | 0.7 cm | 3 |
| 18 | 285-54 | 2 hole - 500 μm - 2 mm | 2428 (n = 3) | AS | 0.7 cm | 3 |
| 19 | 285-54 | 3 hole - 375 μm - 2 mm | 3068 (n = 3) | AS | 0.7 cm | 3 |
| 20 | 285-54 | 3 hole - 500 μm - 2 mm | 2899 (n = 3) | AS | 0.7 cm | 3 |
| 21 | 285-126C | 2 hole - 250 μm - 1 mm | 2770 (n = 3) | BS | 0.7 cm | 3 |
| 22 | 285-126C | 2 hole - 375 μm - 1 mm | 2591 (n = 3) | BS | 0.7 cm | 3 |
| 23 | 285-126C | 2 hole - 375 μm - 2 mm | 3245 (n = 3) | BS | 0.7 cm | 3 |
| 24 | 285-126C | 2 hole - 500 μm - 1 mm | 2819 (n = 3) | BS | 0.7 cm | 3 |
| 25 | 285-126C | 3 hole - 500 μm - 1.5 mm | 2955 (n = 3) | BS | 0.7 cm | 3 |
| 26 | 285-126D | 2 hole - 250 μm - 1 mm | 2615 (n = 3) | AS | 0.7 cm | 3 |
| 27 | 285-126D | 2 hole - 375 μm - 1 mm | 2970 (n = 3) | AS | 0.7 cm | 3 |
| 28 | 285-126D | 2 hole - 375 μm - 2 mm | 2932 (n = 3) | AS | 0.7 cm | 3 |
| 29 | 285-126D | 2 hole - 500 μm - 1 mm | 2619 (n = 3) | AS | 0.7 cm | 3 |
| 30 | 285-126D | 3 hole - 500 μm - 1.5 mm | 2498 (n = 3) | AS | 0.7 cm | 3 |

Each of the 30 implants was placed into a 5 mL centrifuge vial with cap containing 1 mL of phosphate buffer-saline, pH 7.4 (PBS) at 37° C. Total replacement with equal volume of fresh medium was performed on day 1, 4, 7, 14, 28, and every week thereafter. Drug assay was performed on a Waters HPLC system, which included a 2690 (or 2696) Separation Module, and a 2996 Photodiode Array Detector. A Rainin C18, 4.6×100 mm column was used for separation and detector was set at 254 nm. The mobile phase was (50:50) acetonitrile-0.005M NaOAc/HOAc, pH 4.0 with flow rate of 1 mL/min and a total run time of 10 min per sample. Release rates were determined by calculating the amount of drug being released in a given volume of medium over time and expressed in μg/day. The release testing was performed on all 30 configurations in three replicates, except for configurations #5 to 8, for which only one sample of each was tested.

The implants studied varied in the number of holes (2 or 3), hole sizes (250, 325, 375, 460, or 500 μm), distance between the holes (1 mm, 1.5 mm, or 2 mm), length of the implant (1 cm or 0.7 cm), and before or after gamma sterilization, as presented in Table 3.

In general, all 30 implants exhibited an initial burst of drug release on the first day then tapered off to day 7 or later, and finally gradually settled into an equilibrium release range starting after day 14. The first eight configurations were 1 cm in length with drug load of approximately 4.5 mg±0.2 mg in each device, as shown in Table 3. Configurations 1 through 4 were non-sterile, while configurations 5 through 8 were sterile. The cumulative amount released (μg) as a function of time and the amount of release (μg) per day as a function of time are presented in FIGS. 4 through 7.

Configuration #1 (2 hole-250 μm), #2 (2 hole-500 μm), #3 (3 hole-250 μm), and #4 (3 hole-500 μm) gave an average release of 0.63±0.23, 1.72±0.52, 0.94±0.30, and 2.82 μg/day±0.41 μg/day, respectively from day 14 to day 487. These results were compared to their sterile counterparts, configuration #5, #6, #7, and #8, which gave an average release of 0.88, 1.10, 2.48, and 2.84 μg/day, respectively from day 14 to day 448. A good correlation between the number of holes in a configuration and its average daily release was observed for the first four configurations. For example, configuration #3 has 3 holes and configuration #1 has two holes of the same diameter as #3, and configuration #3 released 1½ times more fluocinolone per day than configuration #1. Similar results were obtained with configuration #4 and configuration #2.

In configuration #5 (2 hole-250 μm), #6 (2 hole-500 μm), #7 (3 hole-250 μm), and #8 (3 hole-500 μm), we see approximately a three fold increase in the release rates between configuration #7 and #5, and also between configuration #8 and #6. This was a two-fold increase comparing to the non-sterile counterparts. Configuration #5 (2 holes-250 μm) released an average of 1 μg/day, and configuration #7 (2 holes-500 μm) released an average of 3 μg/day.

Configurations #9 (2 hole-375 μm), #10 (2 hole-460 μm), #11 (3 hole-325 μm), and #12 (3 hole-375 μm) were made and were non-sterile, while configurations 13 through 16 were the sterile counterparts. The cumulative amount released (μg) as a function of time and the amount of release (μg) per day as a function of time are presented in FIGS. 8 through 11. Results from day 14 to day 397 showed an average release of 1.02±0.25, 1.22±0.29, 1.06±0.21, and 1.50±0.39 μg/day for configurations 9, 10, 11, and 12, respectively. Similarly, the data for configurations 13, 14, 15, and 16, which were the sterile counterparts, showed an average release of 1.92±0.23, 2.29±0.33, 1.94±0.18, and 3.15±0.64 μg/day, respectively. Each of the sterile-configurations appeared to be releasing twice as fast as its non-sterile counterpart.

Configuration #13 (2 hole-375 μm-2 mm apart) exhibited an average release of 1.92±0.23 μg/day from day 14 through day 376. Likewise, configuration #15 (3 hole-325 μm-2 mm apart) achieved an average release of 1.94±0.18 μg/day from day 14 through day 376. In the same period of time, configurations #14 and #16 achieved an average release of 2.29 μg±0.33 μg/day and 3.15 μg±0.64 μg/day, respectively. Furthermore, configurations #13 and #15 achieved a total release of 16.02%±0.78% and 14.22%±1.13%, respectively, after 376 days. Based on the release rate, the predicted life span of configurations #13 and #15 are 6.4 and 7.24 years, respectively.

Figure 12:
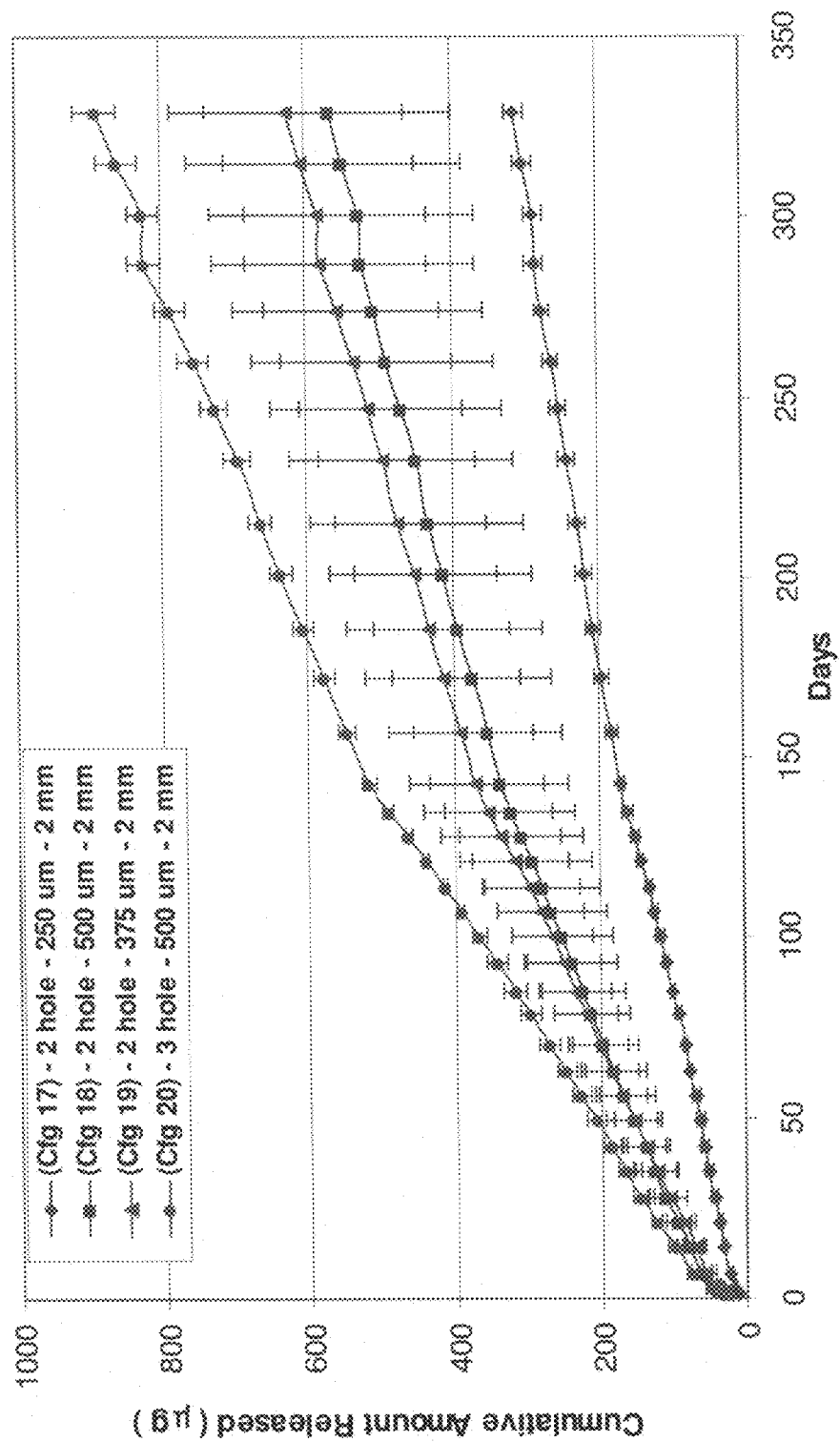
FIG. 12 is a graph showing the cumulative release profiles for sterile fluocinolone acetonide containing implants having different hole configurations.
Figure 13:
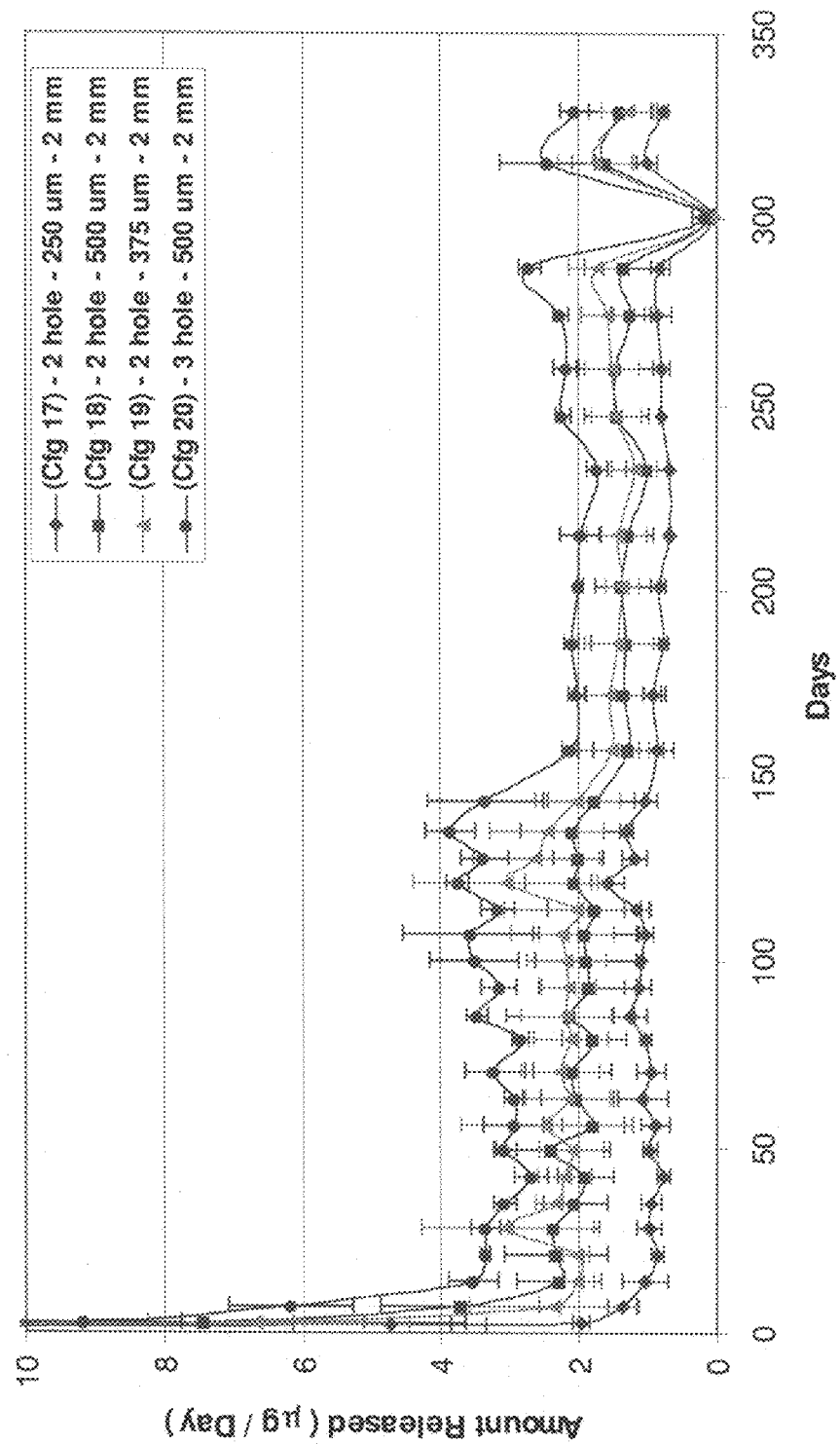
FIG. 13 is a graph showing the amount of fluocinolone released per day for the implants described in FIG. 12.
Figure 14:
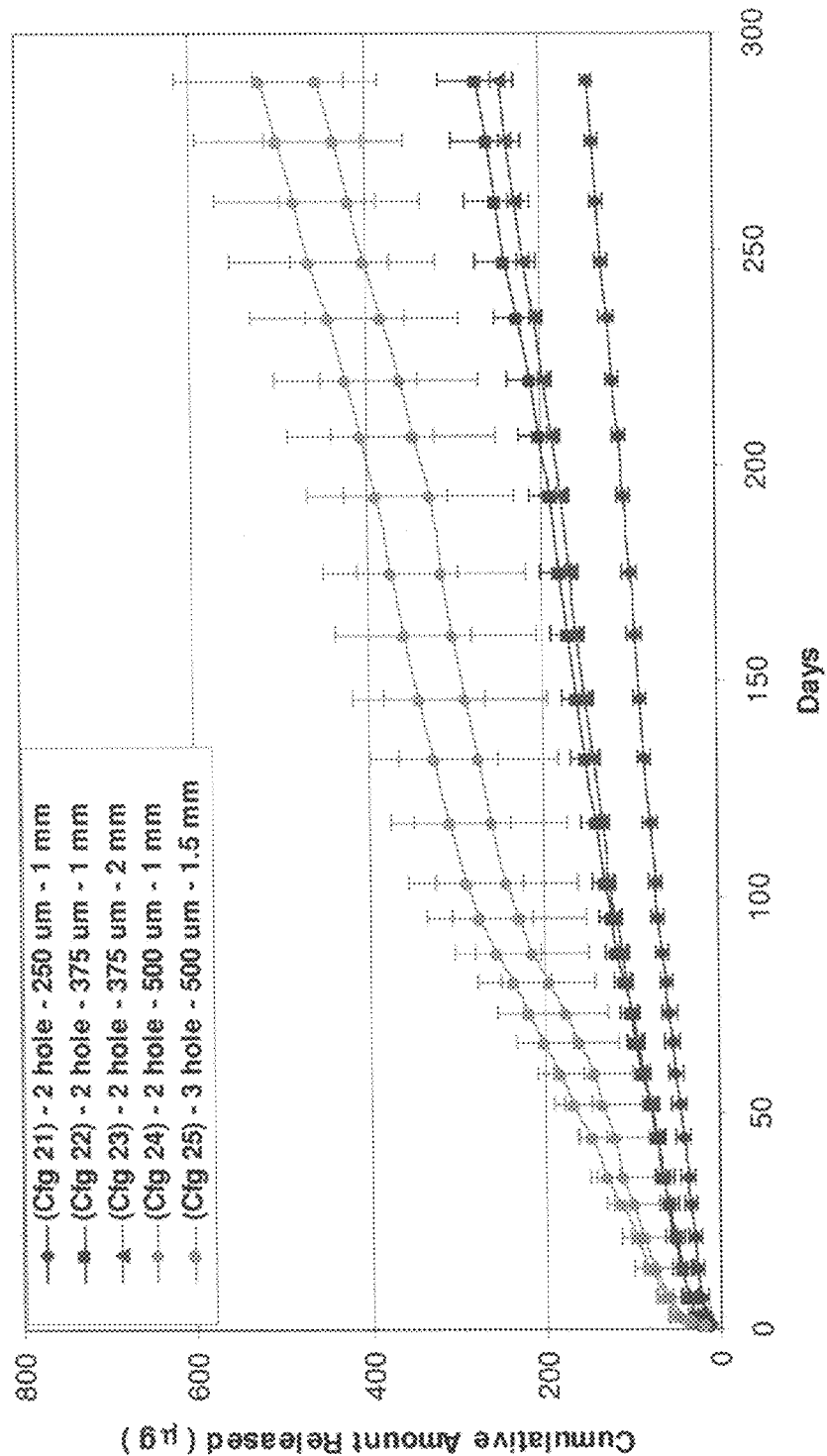
FIG. 14 is a graph showing the cumulative release profiles for non-sterile fluocinolone acetonide containing implants having different hole configurations.
Figure 15:
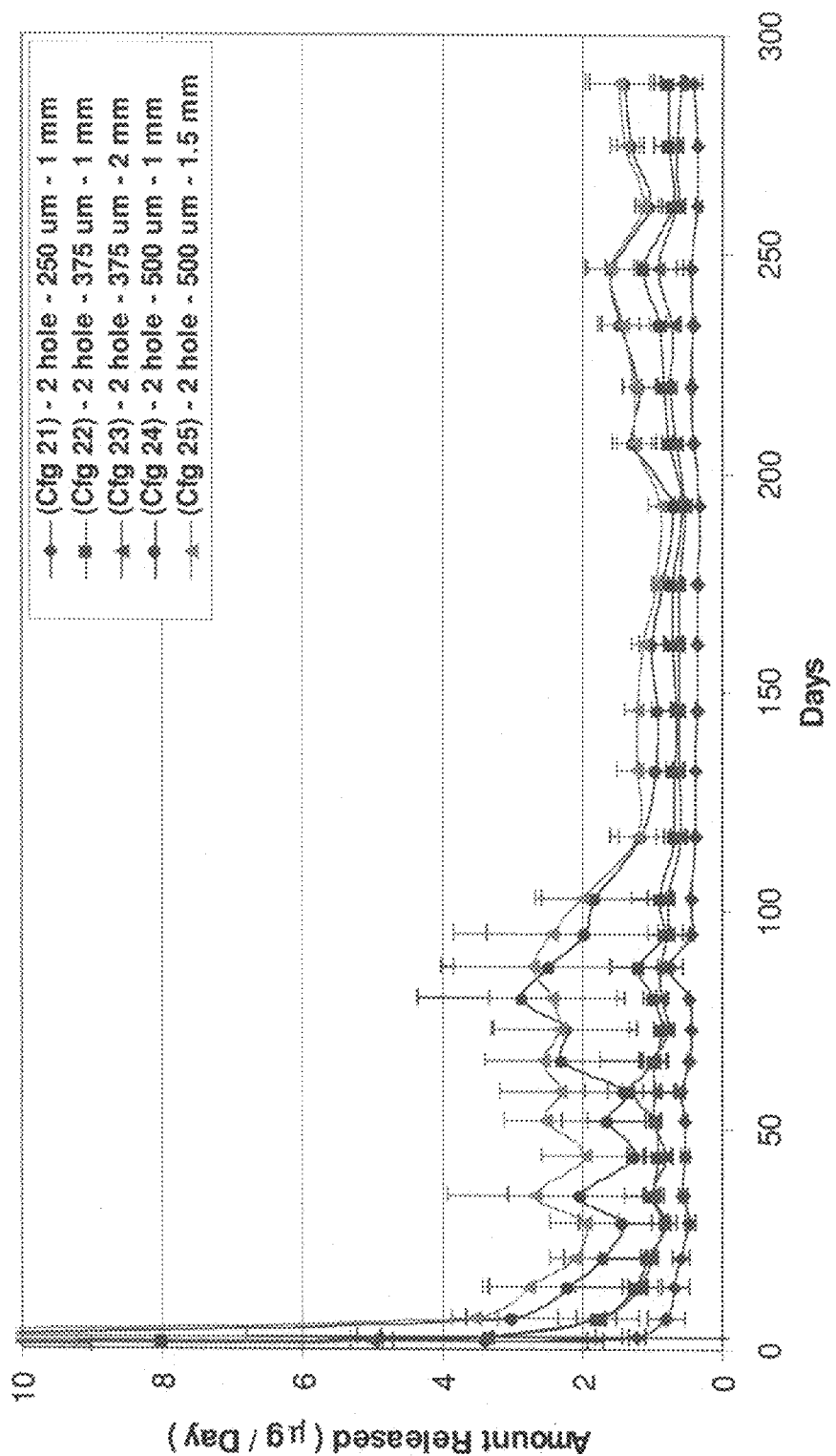
FIG. 15 is a graph showing the amount of fluocinolone released per day for the implants described in FIG. 14.
Figure 16:
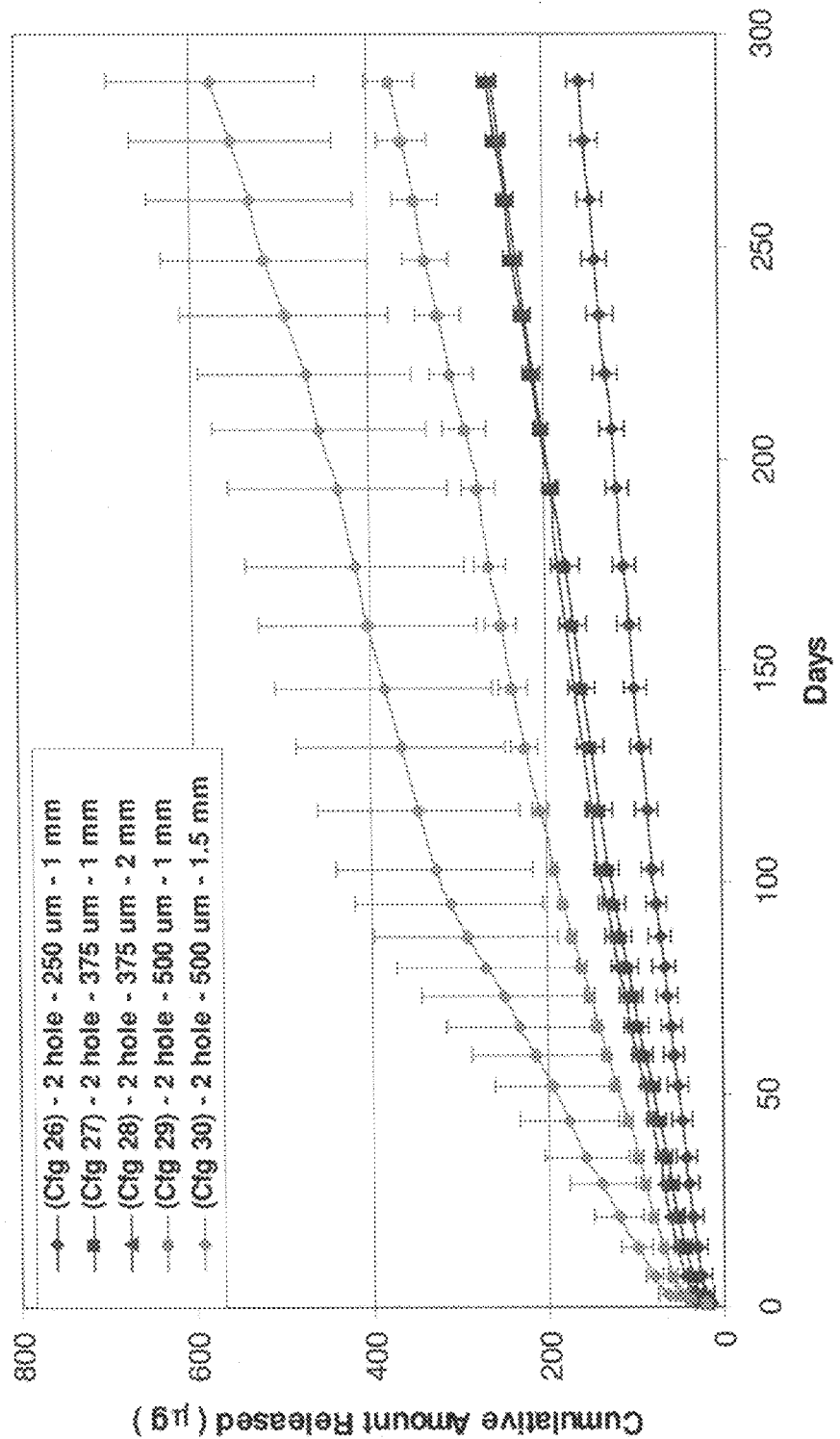
FIG. 16 is a graph showing the cumulative release profiles for sterile fluocinolone acetonide containing implants described in FIG. 14.
Figure 17:
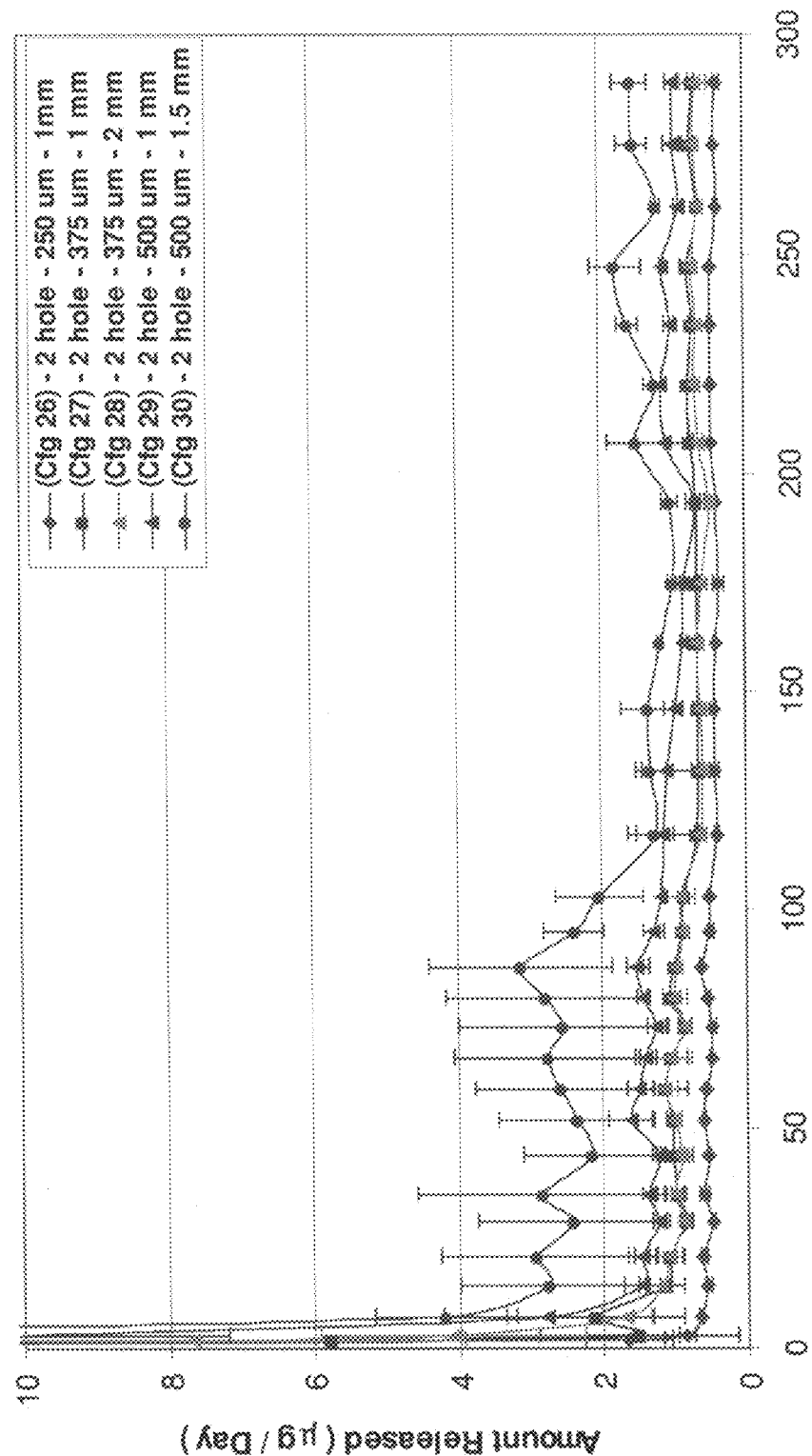
FIG. 17 is a graph showing the amount of fluocinolone released per day for the implants described in FIG. 16.
Figure 18:
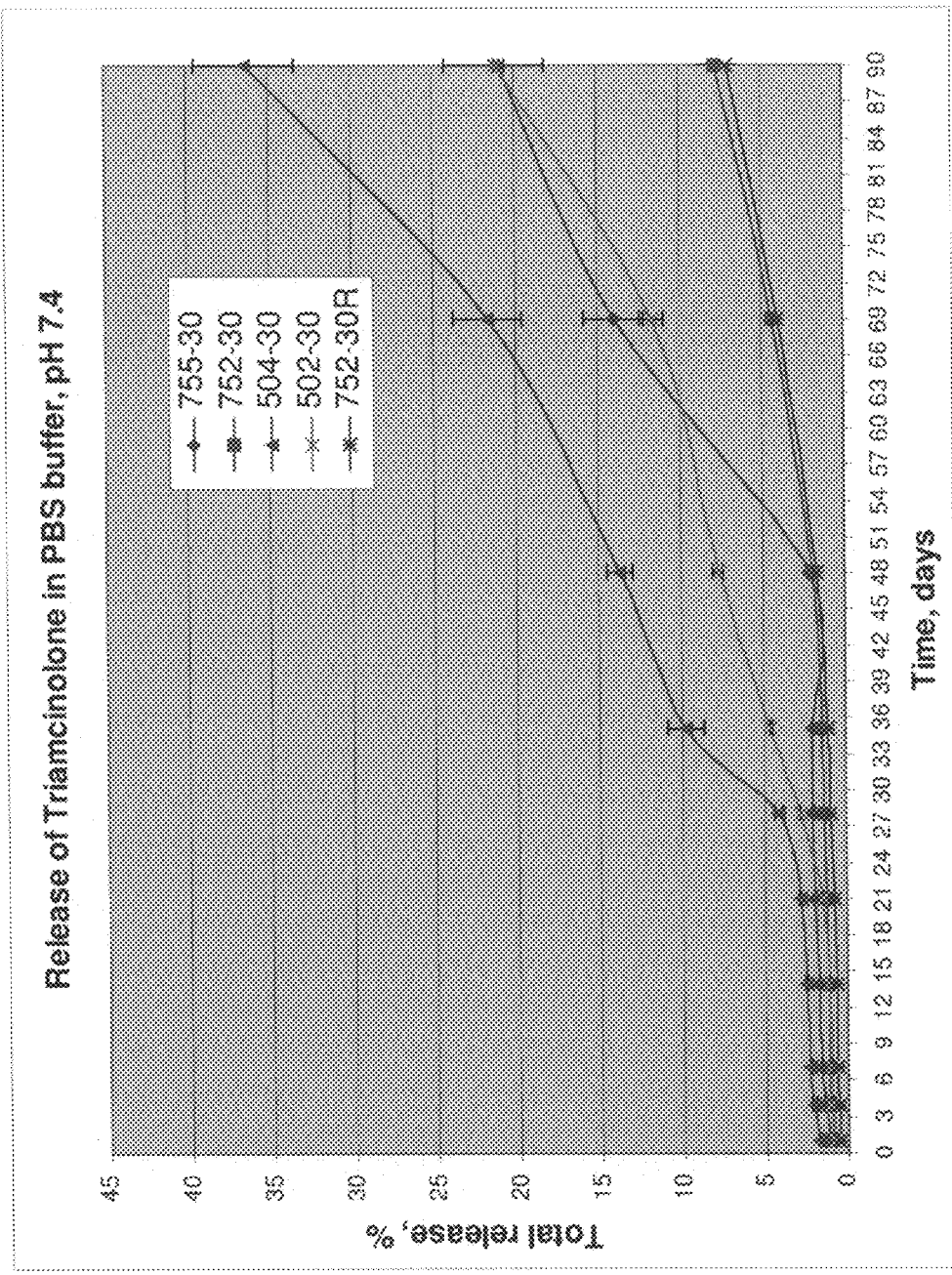
FIG. 18 is a graph showing the total percent release of triamcinolone as a function of time in phosphate buffered saline for implants containing 30% triamcinolone.
Figure 19:
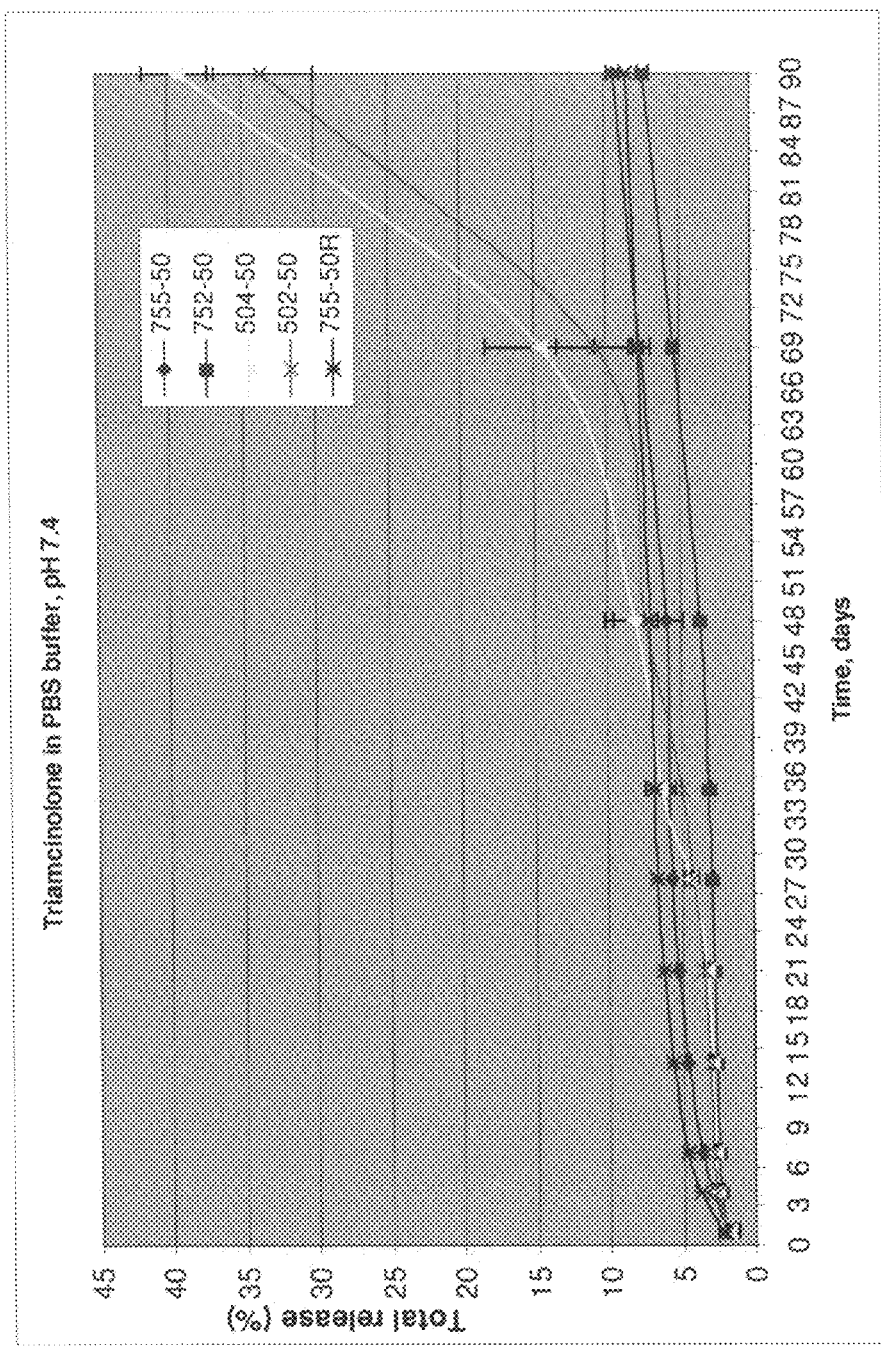
FIG. 19 is a graph showing the total percent release of triamcinolone as a function of time in phosphate buffered saline for implants containing 50% triamcinolone.
Figure 20:
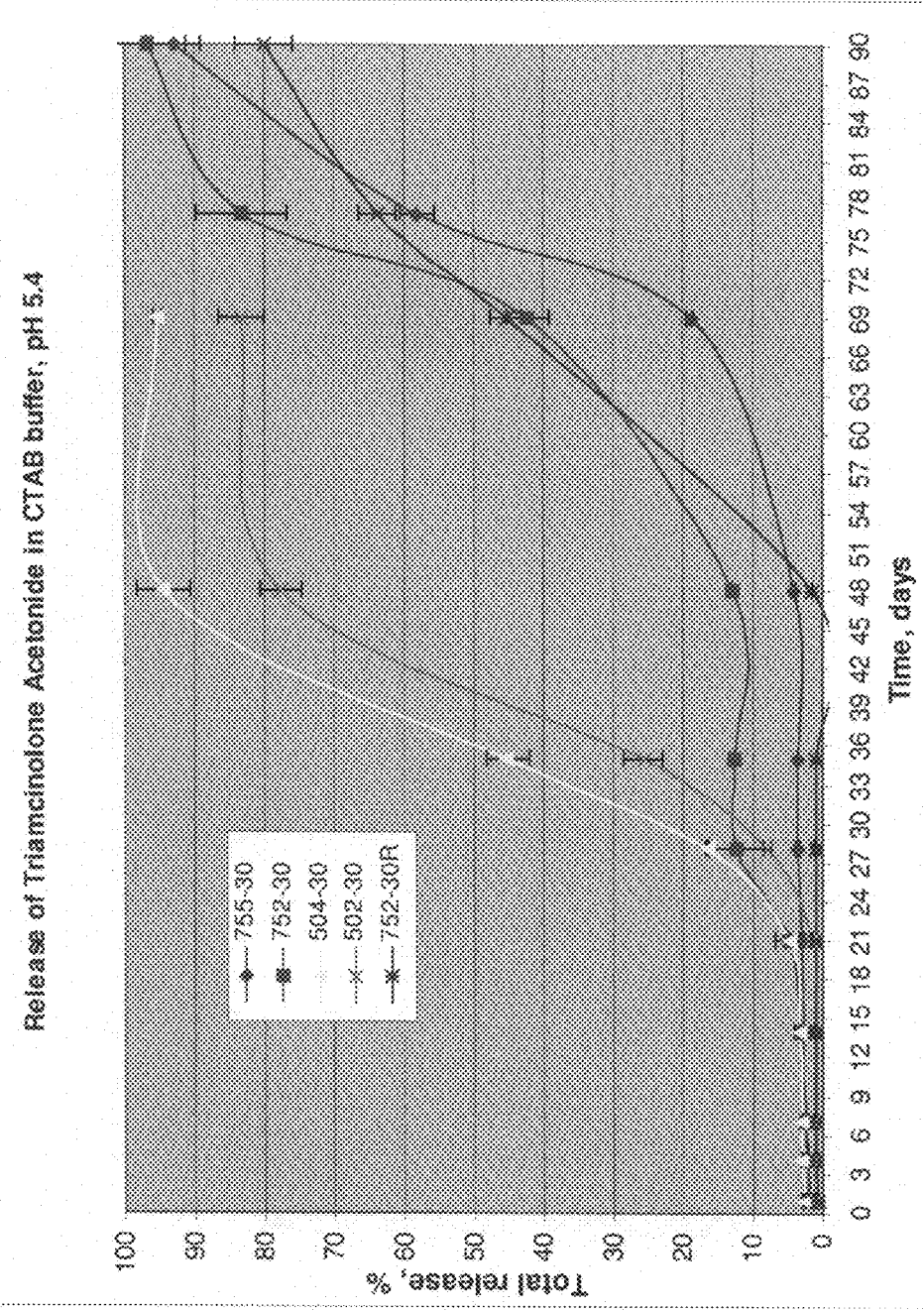
FIG. 20 is a graph showing the total percent release of triamcinolone as a function of time in citrate phosphate buffer for implants containing 30% triamcinolone.
Figure 21:
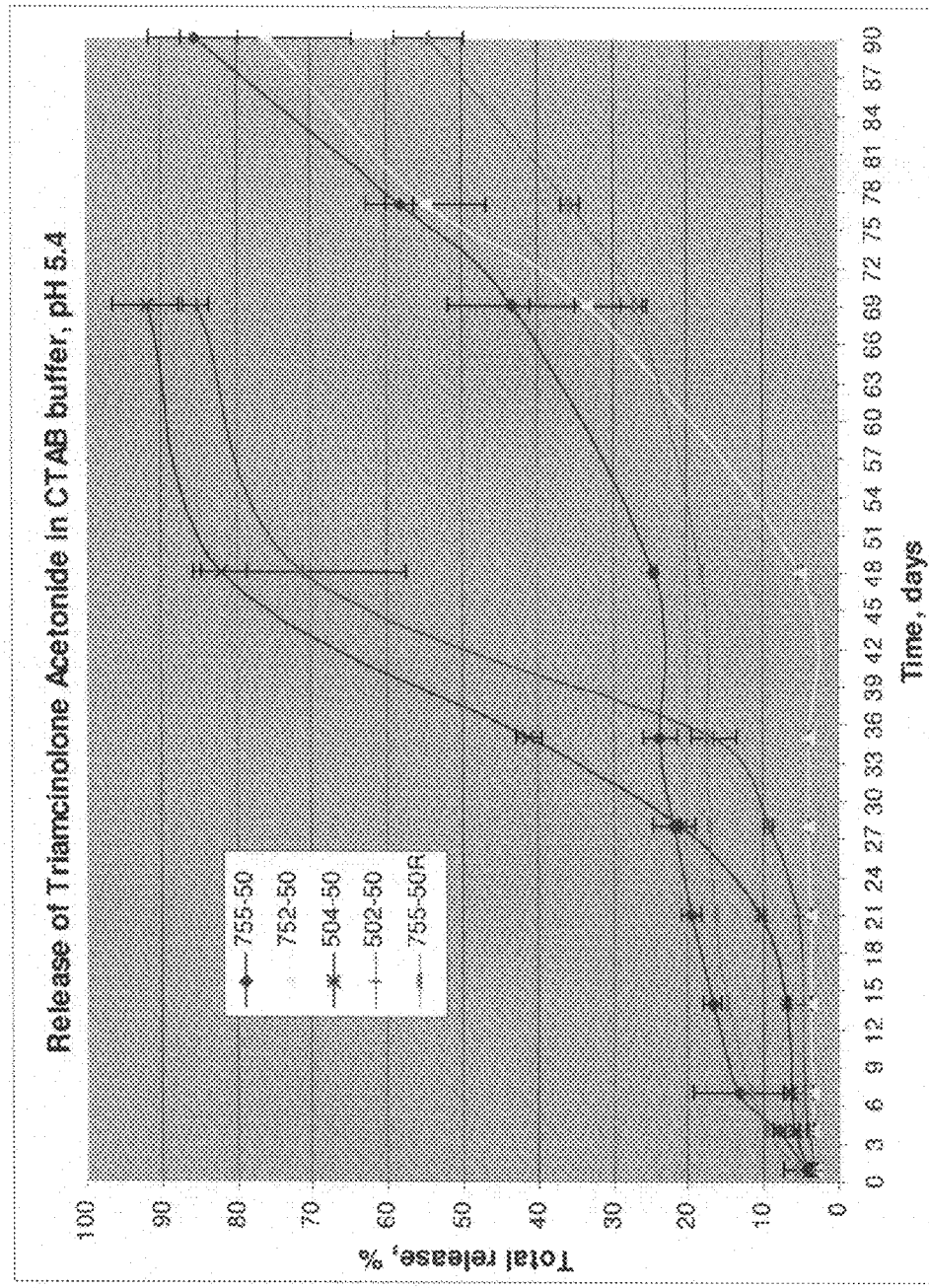
FIG. 21 is a graph showing the total percent release of triamcinolone as a function of time in citrate phosphate buffer for implants containing 50% triamcinolone.
Figure 22:
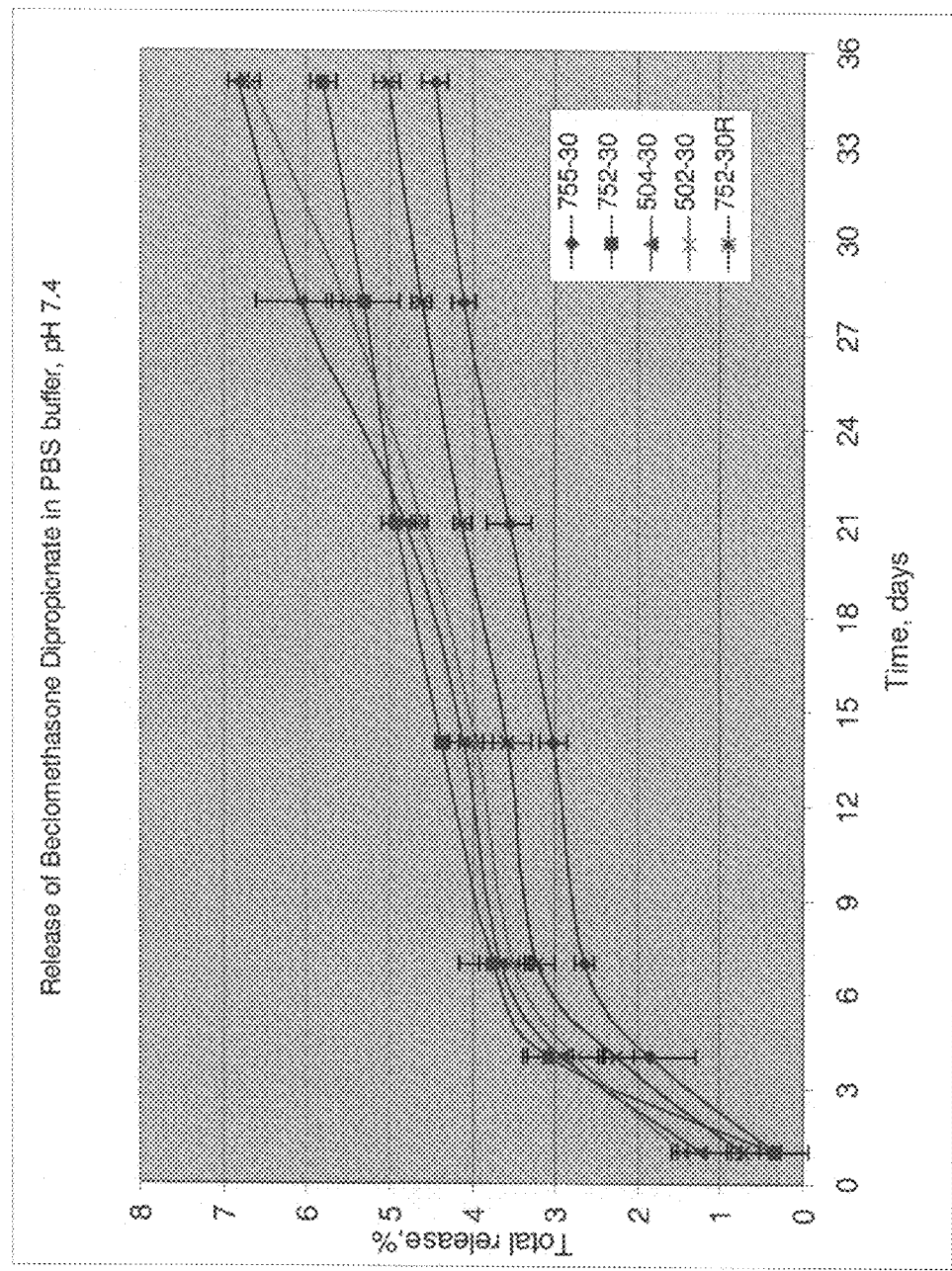
FIG. 22 is a graph showing the total percent release of beclomethasone propionate as a function of time in phosphate buffered saline for implants containing 30% triamcinolone.
Figure 23:
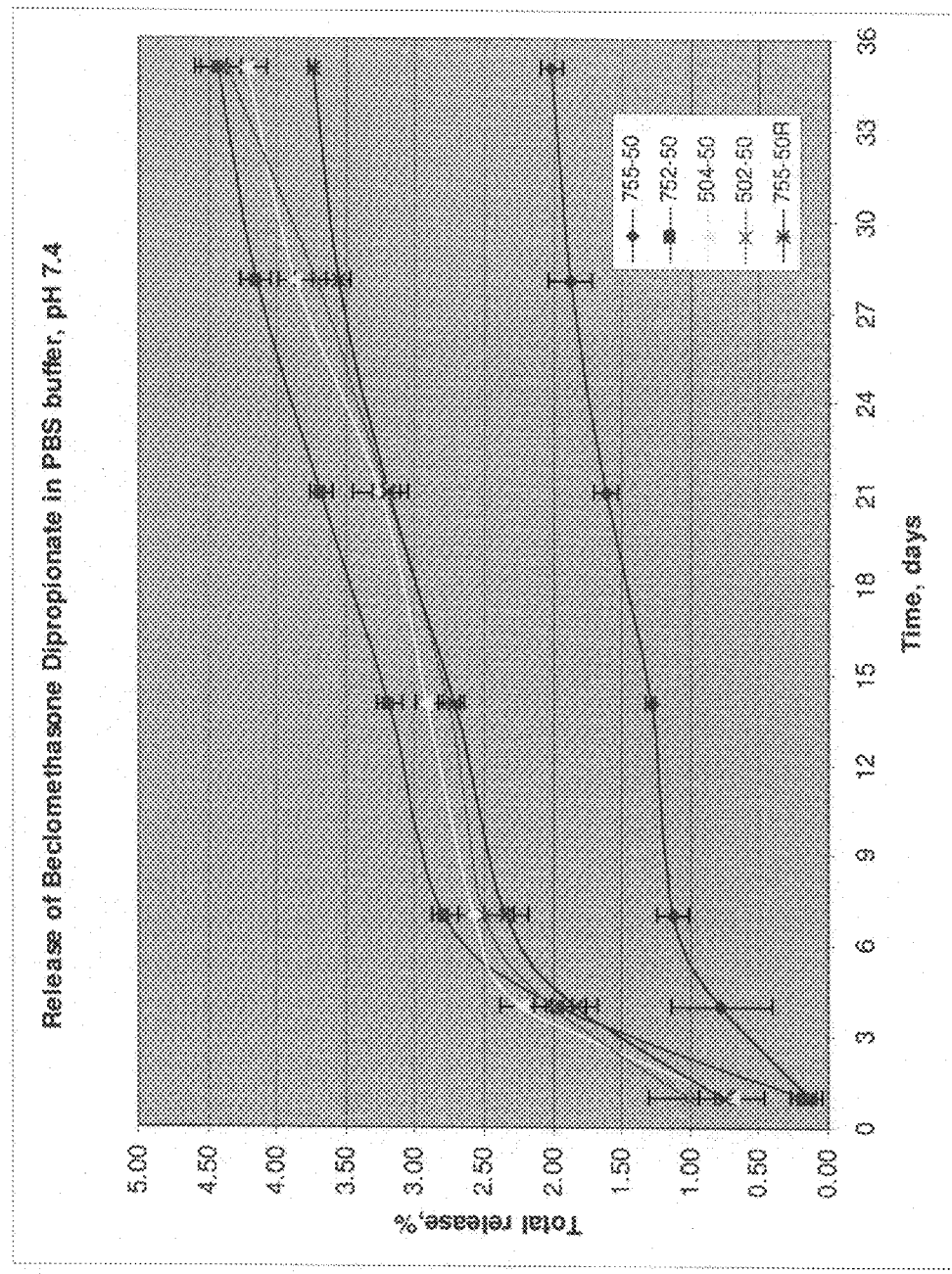
FIG. 23 is a graph showing the total percent release of beclomethasone propionate as a function of time in phosphate buffered saline for implants containing 50% triamcinolone.
Figure 24:
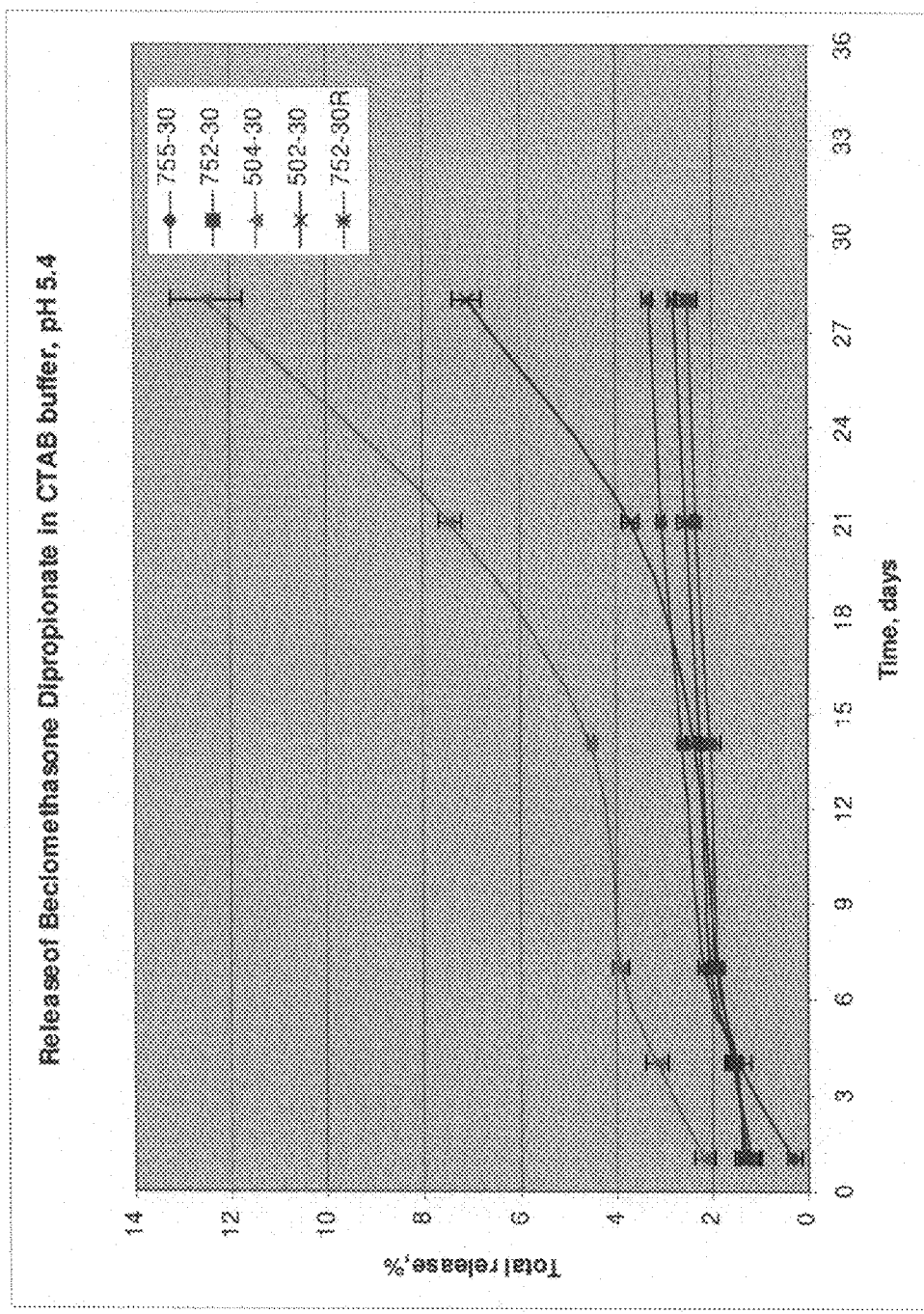
FIG. 24 is a graph showing the total percent release of beclomethasone propionate as a function of time in citrate phosphate buffer for implants containing 30% triamcinolone.
Figure 25:
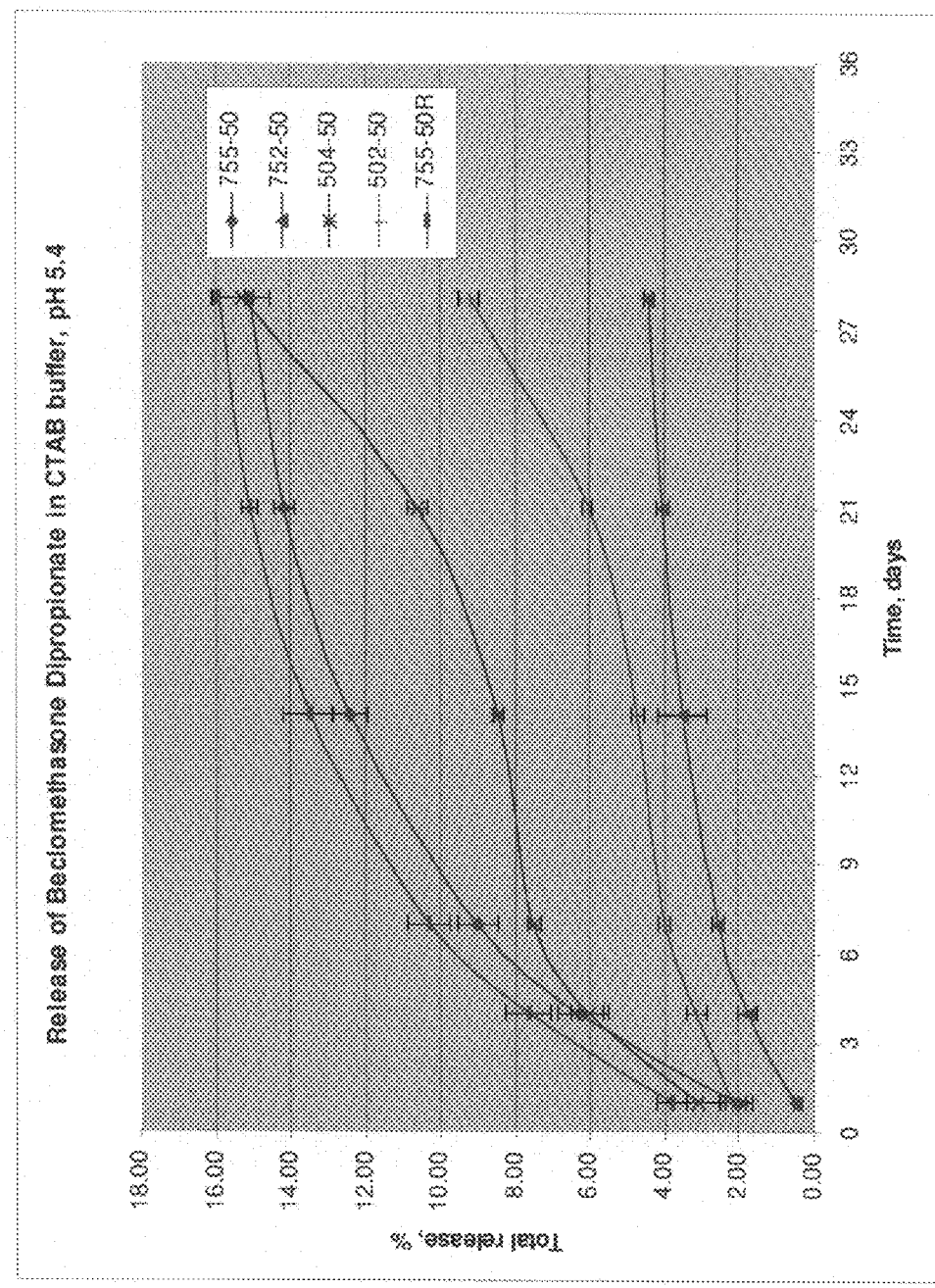
FIG. 25 is a graph showing the total percent release of beclomethasone propionate as a function of time in citrate phosphate buffer for implants containing 50% triamcinolone.

Implants were also manufactured to provide a fluocinolone release rate of about 0.5 μg/day. Tubular implants were manufactured to have a length of about 0.7 cm filled with approximately 2.8 mg±0.34 mg of drug and are identified as configurations 17, 18, 19, and 20. The cumulative amount of fluocinolone released (µg) as a function of time and the amount of release (µg) per day as a function of time are presented in FIGS. 12 and 13, respectively.

The results showed an average release of 0.95±0.14, 1.71±0.55, 1.93±0.56, and 2.76±0.27 µg/day, for configurations 17, 18, 19, and 20, respectively, from day 14 through day 329. Since the length of the tube for configurations 17, 18, 19, and 20 was shortened from 1.0 cm to 0.7 cm, approximately 0.15 cm of silicone tubing was removed from both ends. As a result, the holes became much closer to the end of the tube, to the extent that the glue almost touched the circumference of the holes during preparation. It was not clear whether this affected the release profiles. To circumvent this potential problem, configurations with holes much closer to each other toward the center and away from the ends were prepared.

The last ten configurations were 0.7 cm in length with drug load of approximately 2.69 mg±0.36 mg in each device. Configurations 21 through 25 were pre-sterile, while configurations 26 through 30 were sterile. The cumulative amount released (µg) as a function of time and the amount of release (µg) per day as a function of time are presented in FIGS. 14 through 17.

Results from day 14 to day 289 showed an average release of 1.01±0.23, 1.76±0.57, 1.73±0.30, 3.0±1.26, and 3.32±1.06 µg/day for configurations 21, 22, 23, 23, and 25, respectively. Similarly, the data for configurations 26, 27, 28, 29, and 30, which were the sterile counterparts, showed an average release of 0.48±0.03, 0.85±0.09, 0.82±0.08, 1.19±0.15, and 1.97±0.69 µg/day, respectively, from day 14 through day 289. Configuration #26 (2 holes-250 µm-1 mm apart) achieved an average release of 0.5 µg/day (e.g., 0.48±0.03 µg/day from day 14 through day 289) and a total release of 5.76%±0.32% over 289 days or close to 9½ months. Based on its release rate, it has a life span of 13.75 years. In general, the non-sterile configurations are approximately twice as fast as the sterile counterparts.

Example 4

Manufacture and In Vivo Testing of Intraocular Implants Containing Fluocinolone and a Polymer Coating An in vivo study was conducted with an implant as shown by configuration #29 in Example 3. The implant was manufactured as described in Example 3. Configuration #29 achieved an average release of 1.19±0.15 µg/day, and a total release of 14.28%±1.59% over 289 days when tested in vitro.

The in vivo study was conducted on four rabbits. The fluocinolone-containing implants were surgically implanted into the posterior segment (i.e., the vitreous) of the right eye (OD) and left eye (OS) of each rabbit. The aqueous humor (15-20 µL) and the vitreous humor (150-200 µL) were withdrawn for the first two rabbits, while the sampling for the remaining two rabbits was determined by a sampling schedule wherein the sampling days were days 7, 14, 21, 40, and 60, 90, and 120. The results of the in vivo study are shown in Table 4.

TABLE 4

Fluocinolone acetonide Levels in Vitreous Humor of Rabbit Eyes Posterior Segment Fluocinolone (ng/mL)

| | Day | | | | | | |
|---|---|---|---|---|---|---|---|
| | 7 | 14 | 21 | 40 | 60 | 90 | 120 |
| 8408D | 242.00 | | | | | | |
| 8408S | 88.60 | | | | | | |
| 8399D | 9.08 | 6.84 | 3.06 | | 4.56 | 10.26 | 15.18 |
| 8399S | 44.00 | 74.20 | 85.80 | | 83.60 | 75.60 | 44.00 |
| 8407D | | 105.80 | 87.20 | | 135.80 | 68.60 | 57.20 |
| 8407S | | 16.64 | 6.78 | | 14.92 | 6.62 | 3.46 |
| 8397D | | | | 44.00 | 42.20 | 32.40 | 24.20 |
| 8397S | | | | 40.80 | 22.60 | 23.00 | 24.80 |
| Average | 95.92 | 50.87 | 45.71 | 42.40 | 50.61 | 36.08 | 28.14 |
| SD | 102.68 | 47.16 | 47.13 | 2.26 | 50.19 | 29.46 | 19.49 |

The mean vitreous levels of fluocinolone were relatively higher in the first week and then remained at approximately between 30 and 50 ng/mL beyond the second week. Fluocinolone acetonide was not detected at any time point in the anterior chamber of all eyes.

Thus, by way of Examples 3 and 4, implants have been developed that can deliver fluocinolone at a substantially constant release rate of 2 µg/day or 0.5 µg/day for extended periods of time (e.g., for over 1-2 years).

Configuration #29 (2 hole-500 µm-1 mm) was used in the in vivo study and fluocinolone acetonide concentrations were measured between 0.026 µg/mL to 0.096 µg/mL over 120 days in the vitreous, while essentially no level was found in the aqueous humor.

It was noticed that the release profiles differed depending on when the implants were sterilized. For some configurations, the before sterilization release rates are about twice as fast as the after sterilization ones, and in other configurations, the reverse was observed. It is possible that sterilization may change the size of the holes in the implants. Two animals developed cataracts after day 120.

Example 5

Treatment of Uveitis with an Intraocular Implant Containing Fluocinolone Associated with a Biodegradable Polymer Matrix A 48 year old female presents with posterior uveitis. She complains of sensitivity to light and ocular pain. An implant containing 250 µg of fluocinolone acetonide and 250 µg of a combination of biodegradable polymers (R502H and R202H at a 1:2 ratio, as described above in Example 1) is placed in the vitreous of both of the woman's eyes using a trocar. After about 2 days, the woman begins to notice a decrease in ocular pain and light sensitivity. She also notices a decreased blurring of vision, and a decrease in floaters. Substantial relief from the uveitis symptoms is obtained within about 7 days, and persists for about three months.

Example 6

Treatment of Uveitis with an Intraocular Implant Containing Fluocinolone Associated with a Polymeric Coating A 62 year old male presents with posterior uveitis. An implant containing 250 µg of fluocinolone acetonide with a polymeric coating having two 500 µm diameter holes spaced 1 mm apart is implanted into the vitreous of both of the patient's eyes using a trocar. The patient reports a decrease in pain and improvement in vision within a week after implantation. The improvements persist for about two years. No cataracts develop over that time.

Example 7

Treatment of Macular Edema with a Steroid Containing Intraocular Implant

A 53 year old male with macular edema is treated by injecting a biodegradable implant into the vitreous of each of the patient's eyes using a syringe with a needle. The implants contain 500 µg of fluocinolone acetonide and 500 µg of PLGA. The patient reports a decrease in pain and improvement in vision within a week after implantation. The improvements persist for about two years. No cataracts develop over that time.

Example 8

Treatment of Macular Degeneration with a Steroid Containing Intraocular Implant An 82 year old female diagnosed with macular degeneration in her right eye is treated by intravitreal placement of a biodegradable implant containing 600 µg of fluocinolone acetonide and 500 µg of PLGA. The implant is placed near the fovea without interfering with the patient's vision. Further ophthalmic diagnosis indicates that macular degeneration is suspended, and the patient does not perceive further vision loss associated with macular degeneration. Throughout the treatment, intraocular pressure remains within acceptable limits.

Example 9

Effects of Polymer Properties and Drug Load on Intraocular Implants

This example describes effects of poly (lactide-co-glycolide) (PLGA) polymer properties and drug load on in-vitro drug release profiles of steroids from polymeric implants. More specifically, this example describes the effects of polymer molecular weight (MW), lactide-glycolide (LG) ratio, and steroid load on the release profile of triamcinolone acetonide (TA) or beclomethasone dipropionate (BD) from poly (D, L-lactide-co-glycolide) polymer implants containing triamcinolone acetonide (TA) or beclomethasone dipropionate (BD).

Drug release profiles of the present implants are related to the molecular weight (MW) of the polymer, such as PLGA in this example, the lactide-glycolide ratio (LG) of the polymer, and the drug load or amount of drug in the implant. Steroid release from the implants was examined in phosphate buffered saline (pH 7.4; PBS) or citrate phosphate buffer containing 0.1% cetytrimethylammonium bromide (pH 5.4; CTAB).

In short, the implants were made by melt extrusion, and the steroid release from the implant was assayed by HPLC after incubation at 37° C. in phosphate buffered saline pH 7.4 or citrate phosphate buffer with 0.1% cetyltrimethylammonium bromide pH 5.4. Triamcinolone release from the implants was monitored for 90 days, and beclomethasone dipropionate release from implants was monitored for 35 days.

The results of these experiments show that both steroids release much faster in the citrate buffer compared to the phosphate buffer. During the first 30 days, the release profiles of the two steroids are very similar even though triamcinolone acetonide is about 150 times more water soluble than beclomethasone dipropionate. Polymer properties have a minor effect on the release profile in this time frame or portion of the release profile (e.g., within approximately the first 30 days). In this early phase, the release appears to be controlled by the drug dissolution. The polymer properties become more important after the first 30 days or during a second time frame or portion of the release profile as the polymer's hydrolysis rate differences become more important.

Triamcinolone acetonide was obtained from Pharmacia Upjohn Co. Beclamethasone dipropionate was obtained from Sigma. PLGA polymers RG502, RG504, RG752, and RG755 were obtained from Boehringer-lngelheim Pharma GmbH & Co. (Germany). Saline solution (0.9% NaCl) was obtained from VWR Scientific. Cetyltrimethylammonium bromide (CTAB) was obtained from Aldrich.

The following equipment was used: a ball mill (model mm200; F. Kurt Retsch GmbH & Co., Germany); a turbula shaker (model T2F Nr.990720, Glen Mills, Inc., New Jersey); a piston extruder obtained from APS Engineering, Inc.; a compactor (model A-1024, Jamesville Tool & Manufacturing, Inc., Milton Wis.); a shaking water bath (model 50, Precision Scientific, Winchester, Va.); a high pressure liquid chromatograph (HPLC, model Alliance 2695, Equipped with a Waters 2497 Dual Wavelength Absorbance Detector, Waters, Inc., Milford, Mass.); and an oven (model 1330F, VWR Scientific, Cornelius, Oreg.).

In this example, implants were produced by an extrusion process. Steroids and polymer(s) were combined in a stainless steel ball-mill capsule along with two stainless steel mixing balls. The capsule was placed on the ball mill for five minutes at 20 cps. The capsule was removed from the ball mill and the content was stirred with a spatula; then placed back on the ball mill. This was repeated for two more five-minute cycles. The ball-mill capsule was then placed on a Turbula mixer for five minutes at 20 cps. The content of the capsule was transferred in small increments to an extruder barrel fitted with a die using a spatula and a small stainless steel funnel. After each increment, the powder was compacted in the extruder barrel with the compactor set at 50 psi. When the extruder barrel was full, it is transferred to the extruder and the extruder was heated to temperature and allowed to equilibrate. The polymer steroid mixture was extruded through the die at 0.025 in/min.; the resulting filament was cut into approximately four-inch lengths and placed into a 60-mL screw cap vial, which was placed in a laminated foil pouch with a desiccant pack.

The experimental conditions for the extrusions are shown in Table 5 and Table 6 for triamcinolone acetonide and beclamethasone dipropionate, respectively.

TABLE 5

Triamcinolone Acetonide/PLGA Extrusion Parameters

| Polymer | Polymer ratio, % | Drug Load, % | Compactor Press, psi | Diameter of Die, um | Extrusion Speed, "/min | Extrusion Temp, ° C. |
|---|---|---|---|---|---|---|
| RG752 | 100 | 30 | 50 | 720 | 0.0025 | 95 |
| RG752 | 100 | 50 | 50 | 720 | 0.0025 | 96 |
| RG755 | 100 | 30 | 50 | 720 | 0.0025 | 97 |
| RG755 | 100 | 50 | 50 | 720 | 0.0025 | 96 |
| RG502 | 100 | 30 | 50 | 720 | 0.0025 | 97 |
| RG502 | 100 | 50 | 50 | 720 | 0.0025 | 98 |
| RG504 | 100 | 30 | 50 | 720 | 0.0025 | 94 |

TABLE 5-continued

Triamcinolone Acetonide/PLGA Extrusion Parameters

| Polymer | Polymer ratio, % | Drug Load, % | Compactor Press, psi | Diameter of Die, um | Extrusion Speed, "/min | Extrusion Temp, ° C. |
|---|---|---|---|---|---|---|
| RG504 | 100 | 50 | 50 | 720 | 0.0025 | 98 |
| RG755 | 100 | 50 | 50 | 720 | 0.0025 | 101 |
| RG752 | 100 | 30 | 50 | 720 | 0.0025 | 87 |

TABLE 6

Beclomethasone/PLGA Extrusion Parameters

| Polymer | Polymer ratio, % | Drug Loading, % | Compactor Press, psi | Diameter of Die, um | Extrusion Speed, "/min | Extrusion Temp*, ° C. |
|---|---|---|---|---|---|---|
| RG755 | 100 | 30 | 50 | 720 | 0.0025 | 94 |
| RG755 | 100 | 50 | 50 | 720 | 0.0025 | 99-109 |
| RG752 | 100 | 30 | 50 | 720 | 0.0025 | 95-100 |
| RG752 | 100 | 50 | 50 | 720 | 0.0025 | 96 |
| RG504 | 100 | 30 | 50 | 720 | 0.0025 | 98 |
| RG504 | 100 | 50 | 50 | 720 | 0.0025 | 104-114 |
| RG502 | 100 | 30 | 50 | 720 | 0.0025 | 89-99 |
| RG502 | 100 | 50 | 50 | 720 | 0.0025 | 95-96 |
| RG755 | 100 | 50 | 50 | 720 | 0.0025 | 95 |
| RG752 | 100 | 30 | 50 | 720 | 0.0025 | 95 |

*The mixture of API (the active pharmaceutical ingredient, that is the drug used) and polymer were left in the extruder at 90□ for 10 min before extrusion was started.

The extruded filaments were cut into 1-mg weight rod-shaped implants (rods). Each rod was placed in a 60-mL vial with 50 mL of phosphate buffered saline pH 7.4 or citrate phosphate buffer pH 5.4 with 0.1% cetyltrimethylammonium bromide (CTAB) in an oscillating water bath (50 rpm) at 37° C. At each time point, the released steroid was assayed (n=6) by HPLC, and the solution was removed from the vial and replaced with fresh buffer. The steroid release was measured after the following days: 1, 4, 7, 14, 21, 28, 35, 48 69, 77, and 90.

Triamcinolone acetonide (TA) released from the PLGA (poly (lactide-co-glycolide) polymer implant was assayed by HPLC (Waters, Milford, Mass.) employing a Waters Symmetry C18, 4.6×75 mm, 3 μm column. The mobile phase was acetonitrile-water (35:65, v/v) with a flow rate of 1.0 mL/min and an injection volume of 20 μL. Ultraviolet detection of TA was done at 243 nm. The total run time was 10 min and the TA retention time was 4.0 min. Quantization was based on peak area and a triamcinolone acetonide standardization curve.

Beclomethasone dipropionate (BD) released from the PLGA polymer implant was assayed by HPLC (Waters, Milford, Mass.) employing a Discovery HS F5 C18, 4.6×150 mm, 5 μm column. The mobile phase was acetonitrile-water (85:15), v/v) with a flow rate of 0.8 mL/min and an injection volume of 30 μL. Ultraviolet detection of BD was done at 240 nm. The total run time was 5 min and BD retention time was 2.5 min. Quantization was based on peak area and a BD standardization curve.

The results from the design were analyzed qualitatively at three times during the dissolution—early, middle and late.

The triamcinolone acetonide release results are shown in Tables 7-10 and in FIGS. 18 to 21, respectively.

As shown, TA released into the CTAB buffer faster than it was released into the PBS buffer. Drug release rate can also be effected by pH and surfactant which can alter the polymer's hydrolysis rate and therefore the drug release rate.

The drug load in the polymer has the largest positive effect on the drug release rate compared to MW and LG ratio for the first 30 days. After the first 30 days, the LG ratio dominated the drug release rate and showed a negative effect. In other words, a higher LG ratio resulted in a slower drug release. Without wishing to be bound by any particular theory or mechanism of action, these effects may be related to high drug loading early in the dissolution resulting in more available drug at the polymeric implant's surface. As drug becomes less available, the drug release rate may be controlled by the hydrolysis of the polymer, which is faster for the lower LG ratio polymer.

Molecular weight of the polymer had a positive effect on drug release rate especially later in the dissolution—faster release was observed with higher MW polymers. While not wishing to be bound by any particular theory or mechanism of action, this may occur because the lower MW polymer pack more densely, and the higher MW polymer hydrolyze faster. Overall, the data show that early drug release is controlled by the drug load but the later in time drug release rate is controlled by the polymer hydrolysis rate.

TABLE 7

Triamcinolone Release Results in Phosphate Buffered Saline pH 7.4 for 30% Drug Load

| | Total release (%) | | | | | | Standard Deviation | | | | |
|---|---|---|---|---|---|---|---|---|---|---|---|
| | 755-30 | 752-30 | 504-30 | 502-30 | 752-30R | | 755-30 | 752-30 | 504-30 | 502-30 | 752-30R |
| 1 | 1.08 | 0.81 | 1.75 | 0.74 | 0.46 | 1 | 0.08 | 0.12 | 0.14 | 0.04 | 0.09 |
| 4 | 1.40 | 1.02 | 2.13 | 0.94 | 0.49 | 4 | 0.05 | 0.11 | 0.13 | 0.04 | 0.03 |
| 7 | 1.56 | 1.08 | 2.29 | 1.00 | 0.59 | 7 | 0.04 | 0.04 | 0.06 | 0.04 | 0.03 |
| 14 | 1.70 | 1.10 | 2.47 | 1.11 | 0.60 | 14 | 0.03 | 0.02 | 0.07 | 0.05 | 0.02 |
| 21 | 1.92 | 1.28 | 2.86 | 1.47 | 0.69 | 21 | 0.03 | 0.03 | 0.03 | 0.01 | 0.04 |
| 28 | 2.05 | 1.37 | 4.14 | 2.77 | 0.97 | 28 | 0.05 | 0.03 | 0.19 | 0.02 | 0.11 |
| 35 | 2.08 | 1.41 | 9.73 | 4.60 | 1.06 | 35 | 0.02 | 0.03 | 1.09 | 0.09 | 0.05 |
| 48 | 2.22 | 1.98 | 13.74 | 7.73 | 1.65 | 48 | 0.12 | 0.03 | 0.83 | 0.33 | 0.10 |
| 69 | 14.03 | 4.42 | 21.70 | 11.70 | 3.98 | 69 | 1.87 | 0.06 | 2.09 | 0.73 | 0.25 |
| 90 | 20.94 | 7.82 | 36.46 | 21.22 | 7.05 | 90 | 0.34 | 0.94 | 3.05 | 3.10 | 0.53 |

TABLE 8

Triamcinolone Release Results in Phosphate Buffered Saline pH 7.4 for 50% Drug Load

| | Total release (%) | | | | | | Standard Deviation | | | | |
|---|---|---|---|---|---|---|---|---|---|---|---|
| | 755-50 | 752-50 | 504-50 | 502-50 | 755-50R | | 755-50 | 752-50 | 504-50 | 502-50 | 755-50R |
| 1 | 1.83 | 2.01 | 1.88 | 1.97 | 2.20 | 1 | 0.35 | 0.15 | 0.72 | 0.09 | 0.16 |
| 4 | 2.93 | 2.32 | 2.56 | 2.57 | 3.75 | 4 | 0.09 | 0.05 | 0.32 | 0.08 | 0.14 |
| 7 | 3.68 | 2.44 | 2.74 | 2.84 | 4.62 | 7 | 0.15 | 0.05 | 0.10 | 0.04 | 0.16 |
| 14 | 4.66 | 2.58 | 2.93 | 3.09 | 5.68 | 14 | 0.12 | 0.06 | 0.08 | 0.05 | 0.11 |
| 21 | 5.23 | 2.73 | 3.16 | 3.46 | 6.21 | 21 | 0.09 | 0.03 | 0.09 | 0.03 | 0.04 |
| 28 | 5.60 | 2.87 | 4.29 | 4.23 | 6.62 | 28 | 0.05 | 0.06 | 0.56 | 0.08 | 0.05 |
| 35 | 5.75 | 2.98 | 6.37 | 4.92 | 6.84 | 35 | 0.01 | 0.05 | 1.01 | 0.04 | 0.03 |
| 48 | 5.92 | 3.70 | 8.07 | 7.44 | 7.04 | 48 | 0.04 | 0.09 | 1.58 | 2.65 | 0.03 |
| 69 | 7.69 | 5.35 | 14.47 | 10.79 | 7.84 | 69 | 0.79 | 0.25 | 3.75 | 2.60 | 0.08 |
| 90 | 9.42 | 7.38 | 39.38 | 33.66 | 8.59 | 90 | 0.47 | 0.37 | 2.45 | 3.63 | 0.08 |

TABLE 9

Triamcinolone Release Results in Citrate Phosphate Buffer pH 5.4 for 30% Drug Load

| | Total release (%) | | | | | | Standard Deviation | | | | |
|---|---|---|---|---|---|---|---|---|---|---|---|
| | 755-30 | 752-30 | 504-30 | 502-30 | 752-30R | | 755-30 | 752-30 | 504-30 | 502-30 | 752-30R |
| 1 | 1.79 | 1.93 | 2.50 | 1.07 | 0.69 | 1 | 0.19 | 1.11 | 0.12 | 0.05 | 0.05 |
| 4 | 2.18 | 1.93 | 2.85 | 1.12 | 0.74 | 4 | 0.03 | 0.00 | 0.02 | 0.04 | 0.03 |
| 7 | 2.35 | 2.22 | 3.03 | 1.13 | 0.86 | 7 | 0.06 | 0.26 | 0.04 | 0.02 | 0.01 |
| 14 | 2.61 | 3.05 | 3.23 | 1.21 | 0.94 | 14 | 0.05 | 1.18 | 0.02 | 0.03 | 0.03 |
| 21 | 3.00 | 4.62 | 4.73 | 1.59 | 0.96 | 21 | 0.21 | 2.06 | 0.04 | 0.02 | 0.02 |
| 28 | 3.45 | 12.44 | 16.60 | 7.99 | 1.00 | 28 | 0.27 | 3.92 | 0.27 | 0.64 | 0.03 |
| 35 | 3.57 | 12.59 | 45.16 | 25.70 | 1.00 | 35 | 0.07 | 0.06 | 2.99 | 2.69 | 0.00 |
| 48 | 4.05 | 12.99 | 94.39 | 77.56 | 1.46 | 48 | 0.27 | 0.04 | 3.90 | 2.92 | 0.04 |
| 69 | 18.96 | 42.24 | 95.24 | 83.21 | 45.40 | 69 | 0.48 | 3.20 | 0.50 | 3.24 | 2.29 |
| 77 | 58.09 | 83.17 | | | 63.83 | 77 | 2.48 | 6.49 | | | 2.71 |
| 90 | 92.97 | 96.82 | | | 79.93 | 90 | 3.88 | 5.73 | | | 4.08 |

TABLE 10

Triamcinolone Release Results in Citrate Phosphate Buffer pH 5.4 for 50% Drug Load

| | Total release (%) | | | | | | Standard Deviation | | | | |
|---|---|---|---|---|---|---|---|---|---|---|---|
| | 755-50 | 752-50 | 504-50 | 502-50 | 755-50R | | 755-50 | 752-50 | 504-50 | 502-50 | 755-50R |
| 1 | 4.32 | 3.14 | 4.10 | 3.10 | 5.63 | 1 | 1.01 | 0.63 | 0.14 | 0.14 | 1.76 |
| 4 | 7.96 | 3.38 | 5.77 | 4.08 | 9.39 | 4 | 0.76 | 0.00 | 0.36 | 0.08 | 0.09 |
| 7 | 13.26 | 3.46 | 6.24 | 4.42 | 11.52 | 7 | 5.93 | 0.05 | 0.17 | 0.03 | 0.07 |
| 14 | 16.75 | 3.60 | 6.79 | 4.77 | 14.79 | 14 | 1.16 | 0.03 | 0.13 | 0.03 | 0.15 |
| 21 | 19.60 | 3.80 | 10.34 | 5.25 | 16.43 | 21 | 1.23 | 0.03 | 0.32 | 0.03 | 0.12 |
| 28 | 21.91 | 3.90 | 20.94 | 9.17 | 17.21 | 28 | 2.78 | 0.02 | 0.14 | 0.55 | 0.11 |
| 35 | 23.75 | 4.02 | 41.21 | 16.58 | 17.59 | 35 | 2.20 | 0.03 | 1.66 | 3.08 | 0.06 |
| 48 | 24.50 | 5.02 | 82.11 | 71.13 | 18.38 | 48 | 0.34 | 0.19 | 3.58 | 13.62 | 0.10 |
| 69 | 43.48 | 33.38 | 91.91 | 85.27 | 27.09 | 69 | 8.47 | 7.52 | 4.47 | 1.67 | 1.65 |
| 77 | 58.17 | 54.68 | | | 35.62 | 77 | 1.78 | 7.97 | | | 1.13 |
| 90 | 85.58 | 75.87 | | | 54.43 | 90 | 5.86 | 11.33 | | | 4.57 |

The beclomethasone dipropionate release results are shown in Tables 11-14 and are plotted in FIGS. 22 to 25, respectively.

In these experiments, beclomethasone dipropionate release was examined for about one month. In this early timeframe (e.g., within about 1 month), the release profiles for BD and TA were similar even though BD is about 150 times less soluble than TA. Changing to an acidic media increased the amount of released BD slightly but not as much as the same medium change did for TA. The BD release did not increase with increase drug load in the phosphate buffer, but did in the CTAB buffer. The response to increasing LG ratio was the same for both steroids for the first month. The effect is relatively small in the first 30 days but increasing the LG ratio decreases the amount of drug released. The effect of MW was different for the two steroids; triamcinolone's release increased slightly with higher MW in both media, whereas beclomethasone's release decreased in PBS and increased in CTAB with increasing MW.

TABLE 11

Beclomethasone Dipropionate Release Results in Phosphate Buffered Saline pH 7.4 for 30% Drug Load

| | Total release (%) | | | | | | Standard Deviation | | | | |
|---|---|---|---|---|---|---|---|---|---|---|---|
| | 755-30 | 752-30 | 504-30 | 502-30 | 752-30R | | 755-30 | 752-30 | 504-30 | 502-30 | 752-30R |
| 1 | 0.31 | 0.34 | 1.23 | 1.46 | 0.72 | 1 | 0.05 | 0.41 | 0.35 | 0.06 | 0.19 |
| 4 | 1.86 | 3.07 | 2.90 | 2.75 | 2.27 | 4 | 0.57 | 0.28 | 0.48 | 0.34 | 0.22 |
| 7 | 2.64 | 3.74 | 3.64 | 3.52 | 3.22 | 7 | 0.12 | 0.43 | 0.28 | 0.26 | 0.22 |
| 14 | 3.03 | 4.36 | 4.12 | 3.95 | 3.58 | 14 | 0.17 | 0.09 | 0.16 | 0.21 | 0.28 |
| 21 | 3.56 | 4.92 | 4.80 | 4.61 | 4.13 | 21 | 0.27 | 0.18 | 0.18 | 0.08 | 0.11 |
| 28 | 4.11 | 5.32 | 6.09 | 5.53 | 4.62 | 28 | 0.14 | 0.44 | 0.51 | 0.16 | 0.12 |
| 35 | 4.45 | 5.80 | 6.82 | 6.68 | 5.03 | 35 | 0.16 | 0.16 | 0.13 | 0.11 | 0.15 |
| 48 | | | | | | 48 | | | | | |
| 69 | | | | | | 69 | | | | | |
| 90 | | | | | | 90 | | | | | |

TABLE 12

Beclomethasone Dipropionate Release Results in Phosphate Buffered Saline pH 7.4 for 50% Drug Load

| | Total release (%) | | | | | | Standard Deviation | | | | |
|---|---|---|---|---|---|---|---|---|---|---|---|
| | 755-50 | 752-50 | 504-50 | 502-50 | 755-50R | | 755-50 | 752-50 | 504-50 | 502-50 | 755-50R |
| 1 | 0.11 | 0.18 | 0.70 | 1.01 | 0.75 | 1 | 0.07 | 0.09 | 0.24 | 0.30 | 0.07 |
| 4 | 0.78 | 1.95 | 2.22 | 2.00 | 1.84 | 4 | 0.37 | 0.19 | 0.16 | 0.14 | 0.17 |
| 7 | 1.13 | 2.78 | 2.57 | 2.50 | 2.34 | 7 | 0.12 | 0.10 | 0.30 | 0.18 | 0.16 |
| 14 | 1.29 | 3.19 | 2.91 | 2.75 | 2.72 | 14 | 0.04 | 0.09 | 0.08 | 0.08 | 0.08 |
| 21 | 1.62 | 3.68 | 3.25 | 3.21 | 3.20 | 21 | 0.09 | 0.08 | 0.20 | 0.10 | 0.04 |
| 28 | 1.88 | 4.15 | 3.87 | 3.72 | 3.56 | 28 | 0.15 | 0.11 | 0.12 | 0.16 | 0.08 |
| 35 | 2.02 | 4.42 | 4.22 | 4.36 | 3.75 | 35 | 0.08 | 0.17 | 0.15 | 0.19 | 0.03 |
| 48 | | | | | | 48 | | | | | |
| 69 | | | | | | 69 | | | | | |
| 90 | | | | | | 90 | | | | | |

TABLE 13

Beclomethasone Dipropionate Release Results in Citrate Phosphate Buffer pH 5.4 for 30% Drug Load

| | Total release (%) | | | | | | Standard Deviation | | | | |
|---|---|---|---|---|---|---|---|---|---|---|---|
| | 755-30 | 752-30 | 504-30 | 502-30 | 752-30R | | 755-30 | 752-30 | 504-30 | 502-30 | 752-30R |
| 1 | 0.28 | 1.20 | 2.16 | 1.28 | 1.37 | 1 | 0.16 | 0.22 | 0.23 | 0.25 | 0.10 |
| 4 | 1.44 | 1.54 | 3.16 | 1.59 | 1.50 | 4 | 0.24 | 0.11 | 0.22 | 0.16 | 0.11 |
| 7 | 2.15 | 1.87 | 3.90 | 2.04 | 1.93 | 7 | 0.15 | 0.09 | 0.17 | 0.03 | 0.08 |
| 14 | 2.62 | 2.06 | 4.53 | 2.39 | 2.27 | 14 | 0.09 | 0.21 | 0.08 | 0.11 | 0.06 |
| 21 | 3.05 | 2.35 | 7.45 | 3.68 | 2.54 | 21 | 0.09 | 0.05 | 0.24 | 0.16 | 0.16 |
| 28 | 3.32 | 2.50 | 12.51 | 7.09 | 2.82 | 28 | 0.10 | 0.22 | 0.74 | 0.29 | 0.07 |

TABLE 14

Beclomethasone Dipropionate Release Results in Citrate Phosphate Buffer pH 5.4 for 50% Drug Load

| | Total release (%) | | | | | | Standard Deviation | | | | |
|---|---|---|---|---|---|---|---|---|---|---|---|
| | 755-50 | 752-50 | 504-50 | 502-50 | 755-50R | | 755-50 | 752-50 | 504-50 | 502-50 | 755-50R |
| 1 | 2.01 | 0.47 | 3.07 | 2.16 | 3.80 | 1 | 0.36 | 0.06 | 0.74 | 0.37 | 0.42 |
| 4 | 6.26 | 1.77 | 6.01 | 3.16 | 17.64 | 4 | 0.63 | 2.24 | 0.51 | 0.27 | 0.61 |
| 7 | 9.00 | 2.55 | 7.48 | 3.98 | 10.30 | 7 | 0.54 | 0.18 | 0.17 | 0.16 | 0.58 |
| 14 | 12.40 | 3.51 | 8.45 | 4.73 | 13.49 | 14 | 0.49 | 0.66 | 0.15 | 0.18 | 0.65 |
| 21 | 14.16 | 4.06 | 10.59 | 6.04 | 15.06 | 21 | 0.26 | 0.15 | 0.28 | 0.12 | 0.22 |
| 28 | 15.07 | 4.44 | 15.31 | 9.21 | 15.95 | 28 | 0.13 | 0.12 | 0.79 | 0.29 | 0.08 |

Based on these results, the release of low water soluble steroids from PLGA implants is primarily limited by the dissolution of the steroid in the first thirty days, and not the loading or amount of the steroid, or the polymer matrix properties. In the early part of the dissolution (e.g., during the first portion of the drug release profile), the release rates of the two steroids are very similar even though their solubilities are quite different. During this period the drug release rate appears to be controlled by the steroid dissolution with the polymer properties having a minor effect. Later in the dissolution (e.g., during a second portion of the drug release profile), the steroid release is more dependent on polymer properties as the hydrolysis rates of the polymers become more important. Changing to a lower pH media with a lower surface tension increases the amount released for both steroids.

Example 10

Treatment of Uveitis with an Intraocular Implant Comprising Fluocinolone and Timolol Although the patient of Example 5 experiences relief from the symptoms of uveitis with the implant containing fluocinololone acetonide, the intraocular pressure in the eye of the patient increases with time.

An implant containing 250 μg of fluocinolone acetonide, 250 μg of a combination of biodegradable polymers (R502H and R202H in a 1:2 ratio) and 500 μg of timolol, an antiglaucoma drug, is substituted for the implant of Example 5 that contains fluocinololone acetonide without an antiglaucoma drug. The patient experiences relief from the symptoms of uveitis, and the intraocular pressure of the patient remains within acceptable limits. The implant comprising a steroid and an antiglaucoma drug, timolol, provides relief from the symptoms of uveitis while maintaining acceptable intraocular pressure over extended periods of time.

Example 11

Treatment of Macular Edema with a First Intraocular Implant Comprising Fluocinolone and a Second Intraocular Implant Comprising Timolol Although the patient of Example 7 experiences a decrease in pain and improvement in vision after implantation of the implant containing fluocinolone acetonide and PLGA, the intraocular pressure in the eye of the patient increases over time.

A second implant containing 1 mg of timolol and 250 μg of combination of biodegradable polymers (R502H and R202H in a 1:2 ratio) is implanted in the eye of the patient. The intraocular pressure of the patient decreases, and the patient continues to have improvement in vision and decrease in pain.

Example 12

Treatment of Uveitis with an Intraocular Implant Comprising Alternating Layers of Fluocinolone and Timolol A 56 year old male presents with posterior uveitis. An implant containing alternating layers of fluinololone acetonide and brimonidine is formed, where the implant contains a total of 250 μg of flucinololone associated with 250 μg of a combination of biodegradable polymers (R502H and R202H in a 1:2 ratio) and 500 μg of timolol associated with 500 μg of PLGA.

The implant is injected into the vitreous of each of the patient's eyes using a syringe with a needle. The patient reports improvement in vision, and the intraocular pressure remains within acceptable limits.

Example 13

Treatment of Anterior Uveitis with an Intraocular Implant Comprising Dexamethasone and a Second Implant Comprising Timolol Uveitis, a term originally coined to describe inflammation of the uveal tract (iris, ciliary body, choroid, the middle layer of the eye), comprises a group of diverse disease affecting not only the uvea, but also the retinal, optic nerve and vitreous. The current International Uveitits Study Group classification separates uveitis by anatomical location of the disease according to the major visible signs. One of the most common forms of uveitis is anterior uveitis, which affects the area of the iris (irititis), ciliary body (cyclitis) and aqueous humor. Uveitis can also be classified by its duration as acute or chronic (more than three months in duration) and recurrent. The causes of uveitis are diverse and include infection (viral, parasitic, fungal and bacterial), traumatic injury to the eye, and systemic or local autoimmune diseases, although most cases are idiopathic.

Although the topical administration of steroids is the current mainstay of therapy for anterior uveitis, a periocular injection of steroids may also be added in the patient is not responding adequately or in the disease is severe. Additionally, oral corticosteroids may be given if topical administration is ineffective.

Adverse effects from topical steroid use include elevated IOP, optic nerve damage, and cataract formation or progression. Additional risks from periocular injection include globe rupture, fibrosis of the extraocular muscles, and ptosis (eyelid droop) with repeated injections. Systemic absorption from depot periocular administration does occur as well. Side effects of systemic steroid treatment include hypertension, hyperglycemia, gastrointestinal hemorrhage, osteoporosis, and psychosis.

A 52 year old female presents with persistent, non-infectious posterior uveitis in the right eye. Following diagnosis, the patient is given ophthalmic gatifloxacin at an antibacterial concentration, and told to instill a drop on the right eye 4 times a day (QID) for 3 days. On the third day, the patient is administered a first biodegradable polymeric implant containing 700 μg of micronized dexamethasone in a 60:40 weight ration of drug to polymer. The polymer portion of the implant comprises a combination of biodegradable polymers (R502H and R202H in a 1:2 ratio).

At the same time, the patient is also co-administered a first biodegradable polymeric implant containing 700 μg of micronized brimonidine tartrate in a 60:40 weight ration of drug to polymer (R502H and R202H in a 1:2 ratio). The second biodegradable polymeric implant is associated with a polymer coating that is impermeable to the vitreous and containing a plurality of holes, drilled through the polymer coating with a laser, to allow the brimonidine to permeate into the vitreous.

Both implants are simultaneously injected into the eye of the female patient by intracameral injection through the pars plana using an applicator system comprising a 22 gauge needle.

The patient is then monitored weekly for six weeks following implantation of the dexamethasone and brimonidine implants. At each monitoring visit the patient's right eye is carefully examined for signs or abnormalities; the features observed include the eyelid, conjunctiva, cornea, anterior chamber, iris color, lens status, vitreous cells, and retina, including macula, and the optic nerve. The patient's intraocular pressure is also monitored.

At the end of the six week period, the patient has improved vision compared to her situation prior to the insertion of the implants, and the inflammation associated with the uveal tract is absent. The intraocular pressure in the eye of the patient remains within normal levels; no significant increase in degeneration of the retina or optic nerve is seen during the treatment regimen.

Example 14

Treatment of Anterior Uveitis with an Intraocular Implant Comprising Alternating Layers of Dexamethasone and Timolol Intermediate uveitis is characterized by inflammation of the middle of the eye, including the vitreous and peripheral retina. Pars planitis is considered a subset of intermediate uveitis and is characterized by the presence of "snowbanking" over the pars plana and ora serrata. Some ophthalmologists believe that patients with pars planitis have a more severe disease, for example with more macular edema, than other patients with intermediate uveitis.

Vision loss associated with intermediate uveitis is usually due to cystoid macular edema, inflammatory vitreal haze and debris, and cataract. The former two conditions are usually responsive to treatment with anti-inflammatory agents, including anti-inflammatory steroids.

Example 15

Treatment of Intermediate Uveitis with an Intraocular Implant Comprising Dexamethasone and Brimonidine A 56 year old male presents with intermediate uveitis in both eyes, in each case showing involvement of the vitreous (vitreal haze). Following diagnosis, the patient is given ophthalmic gatifloxacin at an antibacterial concentration, and told to instill a drop on the right eye 4 times a day (QID) for 3 days. On the third day, the patient is administered a biodegradable polymeric implant containing 500 µg of micronized dexamethasone and 500 µg brimonidine in a 60:40 weight ration of drug to polymer, and comprising interleaved alternative layers of drug. The polymer portion of the implant comprises a combination of biodegradable polymers (R502H and R202H in a 1:2 ratio).

The implant is injected through the pars plana into the vitreous of each of the patient's eyes using an applicator with a 22 gauge needle. The patient is monitored weekly for six weeks following administration of the implant. The primary indication of efficacy is clearing of vitreal haze, giving rise to increased visual acuity.

At the end of the six-week monitoring period the patient reports improvement in vision, and tests an improvement of 3 lines in visual acuity. Observation shows no trace of vitreal haze remaining, and the intraocular pressure remains within acceptable limits.

Example 16

Intravitreal Delivery of 350 µg or 700 µg Dexamethasone in a Biodegradable PLGA Intraocular Implant An experiment was carried out to study the in vivo release profile of dexamethasone from an intravitreal, biodegradable PLGA implant. New Zealand rabbits were used for this study. The test animals were given an intravitreal injection of a double extruded PLGA implant which comprised dexamethasone substantially homogenously distributed throughout the PLGA polymeric matrix. The implants contained either 350 µg or 700 µg of dexamethasone. The implant which contained 350 µg of dexamethasone weighed about 0.6 mg, while the implant which contained 700 µg of dexamethasone weighed about 1.2 mg. Plasma, aqueous humor, vitreous humor and retinal tissue was collected from either 5 or 6 animals for each dose at the following days post-administration of the implant not the vitreous: at 2, 8, 15, 22, 29, 32, 36, 41, 46, 56, 71, 86, 101, 121, 151, and 181 days. Control tissue samples were taken from the untreated eye of each animal at each time point. Plasma samples were taken from each animal prior to euthanasia. The remaining plasma and tissue samples were collected at necropsy.

Figure 26:
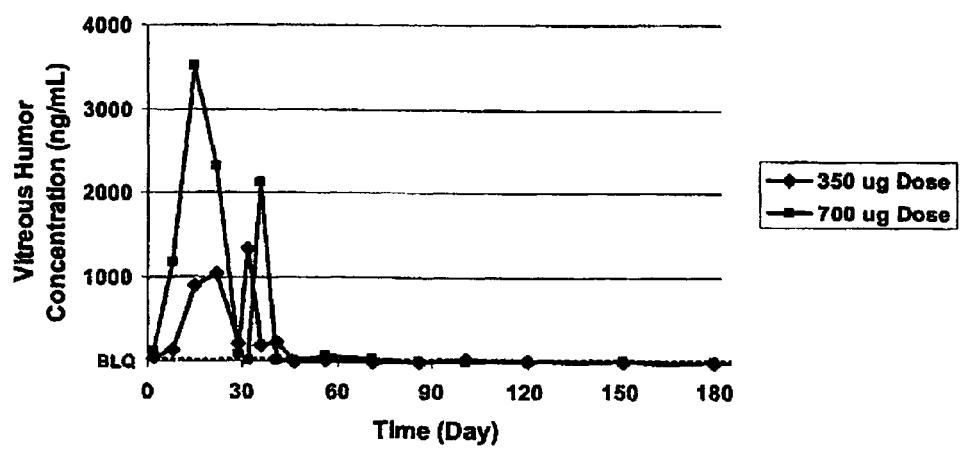
FIG. 26 is a graph showing the concentration of dexamethasone in rabbit vitreous humor following intravitreal administration of a polylactide-polyglycolide (PLGA) filamentous biodegradable intraocular implant containing either 350 ug or 700 ug of dexamethasone. The vitreous humor concentrations are monitored over a 180 day time period.
Figure 27:
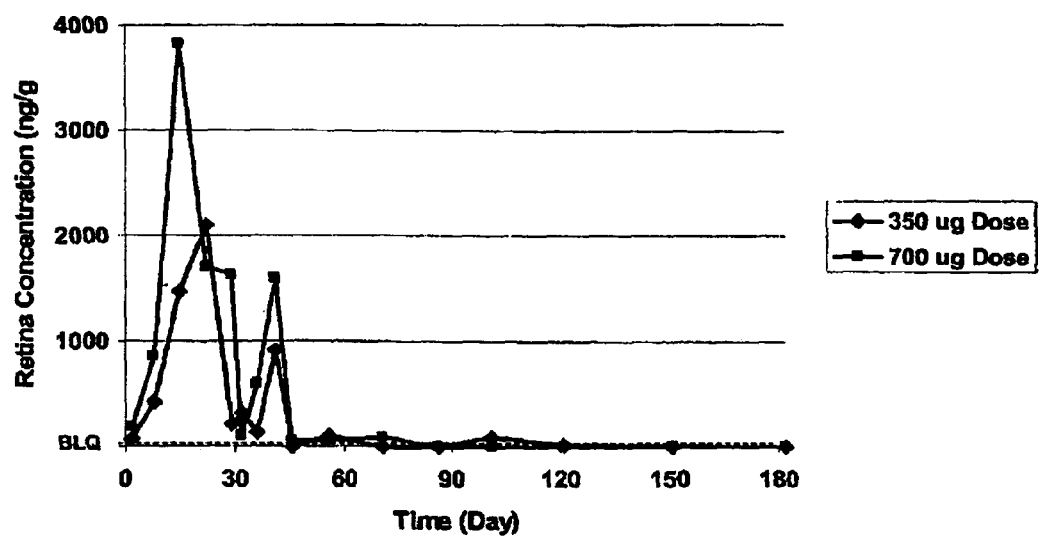
FIG. 27 is a graph showing the concentration of dexamethasone in rabbit retina following intravitreal administration of a polylactide-polyglycolide (PLGA) filamentous biodegradable intraocular implant containing either 350 ug or 700 ug of dexamethasone. The retinal concentrations are monitored over a 180 day time period.
Figure 28:
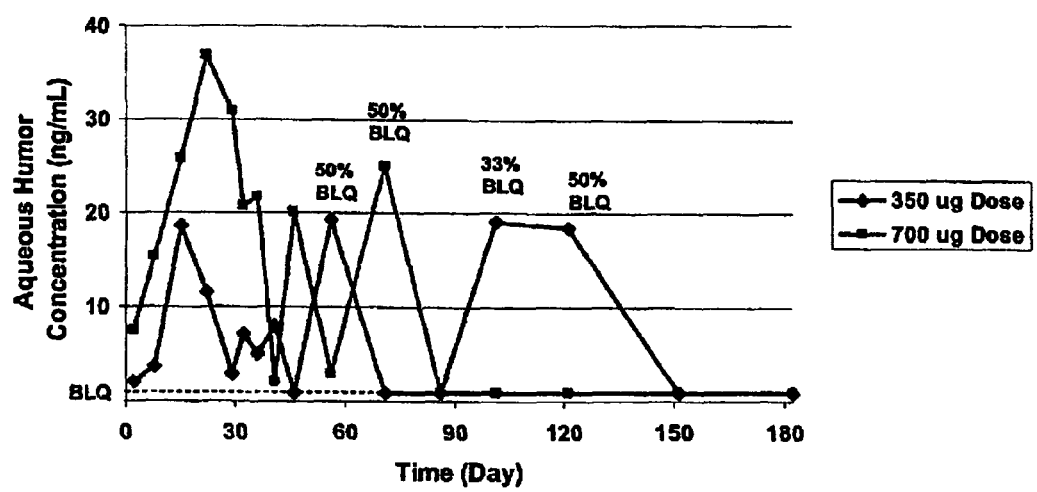
FIG. 28 is a graph showing the concentration of dexamethasone in the aqueous humor following intravitreal administration of a polylactide-polyglycolide (PLGA) filamentous biodegradable intraocular implant containing either 350 ug or 700 ug of dexamethasone. The aqueous humor concentrations are monitored over a 180 day time period.
Figure 29:
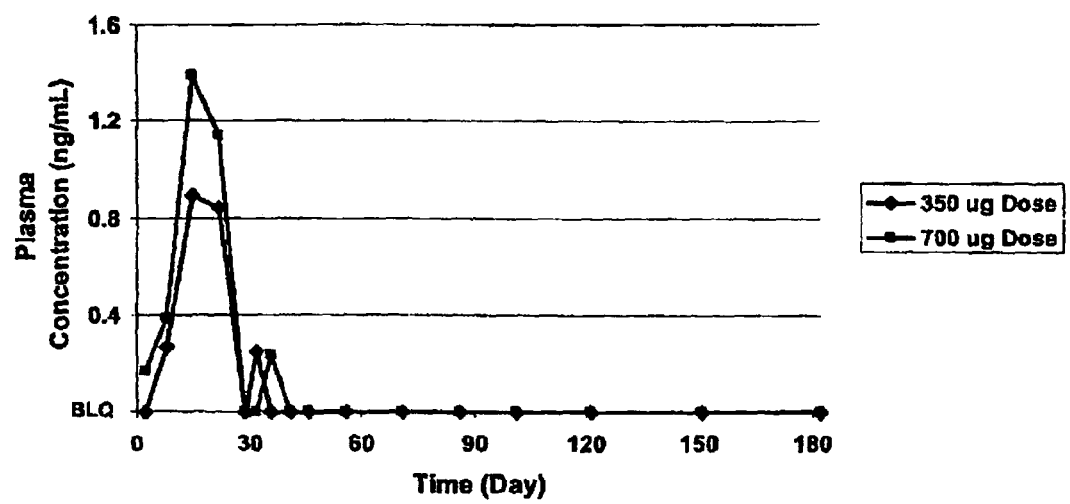
FIG. 29 is a graph showing the concentration of dexamethasone in rabbit plasma following intravitreal administration of a polylactide-polyglycolide (PLGA) filamentous biodegradable intraocular implant containing either 350 ug or 700 ug of dexamethasone. The blood plasma concentrations are monitored over a 180 day time period.
Figure 30:
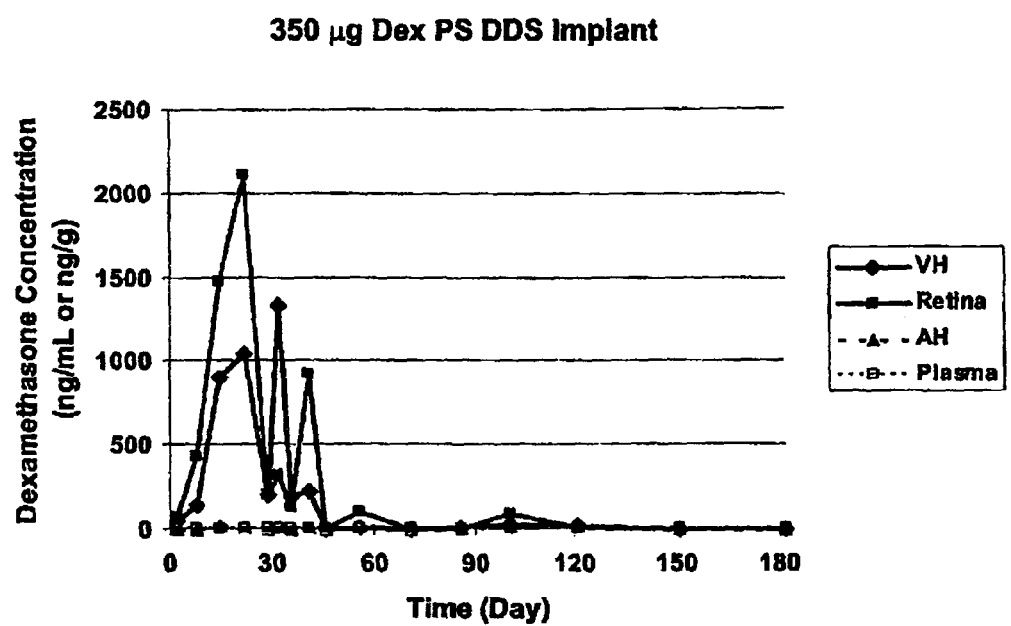
FIG. 30 is a composite graph showing the concentration of dexamethasone over a 180 day period in rabbit aqueous humor, vitreous humor, retina and plasma following intravitreal administration of a polylactide-polyglycolide (PLGA) filamentous biodegradable intraocular implant containing 350 ug of dexamethasone.
Figure 31:
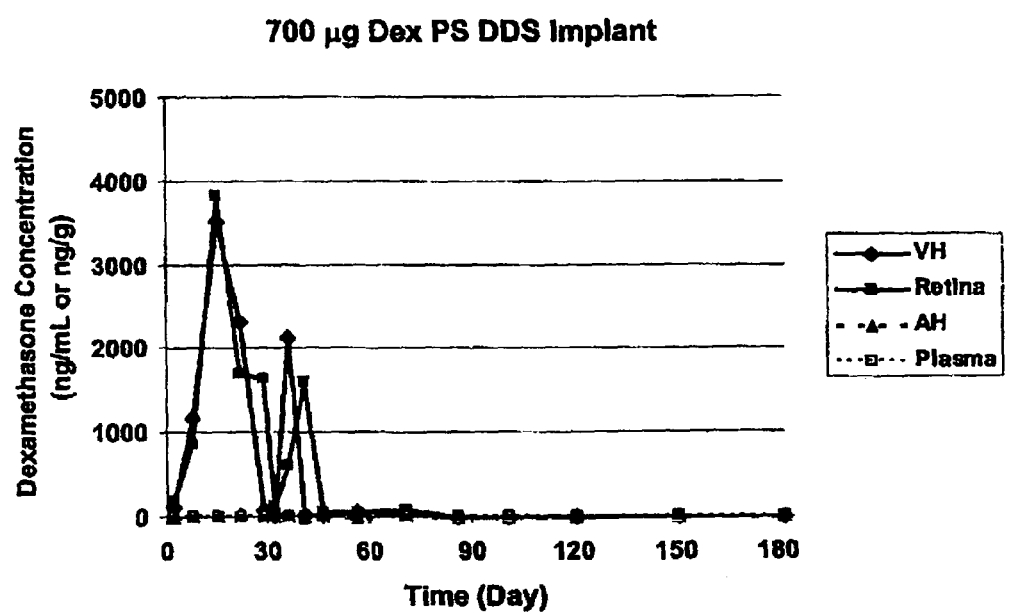
FIG. 31 is a composite graph showing the concentration of dexamethasone over a 180 day period in rabbit aqueous humor, vitreous humor, retina and plasma following intravitreal administration of a polylactide-polyglycolide (PLGA) filamentous biodegradable intraocular implant containing 700 ug of dexamethasone.

FIGS. 26-31 show the results of this study. FIG. 26 shows the dexamethasone concentrations for both the 350 µg dose and the 700 µg dose in the vitreous humor over a 180 day period as a function of time. FIG. 27 shows the dexamethasone concentrations in the retina for both the 350 µg dose and the 700 µg dose over a 180 day period as a function of time. FIG. 28 shows the dexamethasone concentrations in the aqueous humor for both the 350 µg dose and the 700 µg dose over a 180 day period as a function of time. FIG. 29 shows the dexamethasone concentrations in the blood plasma for both the 350 µg dose and the 700 µg dose over a 180 day period as a function of time. FIG. 30 shows the dexamethasone concentrations in the vitreous humor, aqueous humor, retina and the plasma for the 350 µg dose over a 180 day period as a function of time. FIG. 31 shows the dexamethasone concentrations in the vitreous humor, aqueous humor, retina and the plasma for the 700 µg dose over a 180 day period as a function of time.

The result of this experiment showed that a pulsed or biphasic delivery of dexamethasone to the vitreous humor and the retina was provided by the 350 µg and 700 µg PLGA implants used. Retinal drug levels were approximately twice the levels seen in the vitreous humor. Aqueous humor and plasma levels of drug were negligible. Pulsed delivery provides a means to avoid deleterious side effects of continuous steroid exposure to ocular tissues, such as glaucoma and cataract effects.

Example 17

Intermittent or Pulsed Delivery of Dexamethasone in PLGA to the Vitreous Versus Other Corticosteroid Delivery Means A study was carried out to examine free drug levels in the vitreous and in the retina upon intravitreal delivery of 700 µg dexamethasone in a biodegradable PLGA filamentous (rod shaped) implant to rabbit eyes. In this study the experimentally obtained dexamethasone data for the 700 µg dose described in Example 16 was compared to published data for intraocular delivery of two other corticosteroids.

It is known that the effect of treatment of an ocular condition by intravitreal injection of. Kenalog wanes between the three and six month after the intravitreal administration of the Kenalog. See eg Kang S W et al., *Macular grid photocoagulation after intravitreal triamcinolone acetonide for diffuse diabetic macular edema*, Arch Ophthalmol. 2006 May; 124 (5):653-8. On the other hand, as shown by Table 1 in U.S. patent application Ser. No. 11/292,544, filed Dec. 2, 2005, use of the Example 16 implant (Posurdex) can provide an improved visual acuity for at least six months after intravitreal placement of the implant.

In one published report, patients received an intravitreal injection of 4 mg Kenalog® (100 µl of a 40 mg/ml triamcinolone acetonide (TA) aqueous suspension also containing sodium chloride as a tonicity agent, 10 mg/ml benzyl alcohol as a preservative, 7.5 mg/ml of carboxymethylcellulose sodium and 0.4 mg/ml of polysorbate 80 as a resuspension aid) and after a median of 5 days, vitreous taps showed a mean free drug concentration of 1.13 microgram/ml, which decreased in an approximately linear fashion over the first two weeks and over the third week post administration. Inoue, M.; et al., *Vitreous Concentrations Of Triamcinolone Acetonide In Human Eyes After Intravitreal Or Subtenon Injection*. AM. J. OPHTHALMOL. 2004; 138:1046-8.

Additionally, preclinical data upon intravitreal placement of Retisert® (a 0.59 mg non-biodegradable fluocinolone acetonide implant with microcrystalline cellulose, polyvinyl alcohol and magnesium stearate, available from Bausch and Lomb, Inc.) showed vitreous free drug levels of 0.10-0.21 microgram/ml over a 1-year period. Jaffe G J, et al., *Safety And Pharmacokinetics Of An Intraocular Fluocinolone Acetonide Sustained Delivery Device*, INVEST. OPHTHALMOL. VIS. SCI. 2000; 41:3569-75.

Since fluocinolone acetonide has about 5 times the potency of triamcinolone acetonide, its corticosteroid equivalence is from about 0.50 to about 1.05 microgram/ml (Schimmer B. P. and Parker K. L. ACTH: *Adrenocortical Steroids and their Synthetic Analogs*, $10^{th}$ ed. in THE PHARMALOGICAL BASIS OF THERAPEUTICS 1657 (Hardman J. G. and Limbard L. L., editors, McGraw-Hill, 2001). The relative potencies and equivalent doses of various corticosteroids are well known. See eg Table 59-2 on page 1466 of Goodman & Gilman's The Pharmacological Basis of Therapeutics, ninth edition, McGraw Hill (1996).

Data obtained with the Posurdex® 700 ug implant (Allergan, Inc.) (dexamethasone in a polylactide-polyglycolide biodegradable implant; see e.g. U.S. patent application Ser. Nos. 10/340,237 and 10/918,597 ((hereby incorporated by reference herein in their entirety)) show vitreous free drug levels present as early as 2 days post-injection into a mammalian posterior segment. These levels range from about 1.17 to about 3.52 microgram/ml (corticosteroid equivalence to TA is between about 5.85 to about 17.20 microgram/ml (Ibid, Schimmer et al.) between 8 and 22 days, with lower levels detectable for a total of 3-4 months. As stated in Example 16, retinal drug concentrations were found to be nearly double the vitreous levels.

The experimental Posurdex® data and published triamcinolone and fluocinolone data are plotted on the graph shown in FIG. 26. This figure shows the relative differences in free vitreous drug concentrations (adjusted for potency as explained above) for the 3 corticosteroids and different modes of intravitreal injection.

Systemic pulse dosing with corticosteroids has been used to treat asthma, renal graft rejection, lupus nephritis, rheumatoid arthritis as well as other autoimmune and inflammatory diseases. Additionally, oral and intravenous pulsed corticosteroids have been used to treat acute optic neuritis. See eg. Beck R. W., et al., *A randomized, controlled trial of corticosteroids in the treatment of acute optic neuritis. The Optic Neuritis Study Group*, N Engl J Med. 1992 Feb. 27; 326(9): 634-5.

Chronic (i.e. not pulsed) low level dosing of corticosteroids can have deleterious effects on the immune response. Contrarily, the immunologic effects of pulse corticosteroid dosing can result in apoptosis of inflammatory cells (Migita K, et al., supra, and Turcotte, J. G., et al., *Rejection Crises In Human Renal Transplant Recipients: Control With High Dose Methylprednisolone Therapy*, Arch. Surg. 1972; 105:230-6).

Thus, the Cmax levels observed in blood following pulse intravenous corticosteroid dosing can be is 10-15 µg/ml, which is, apparently high enough to cause in vivo apoptosis of T-lymphocytes. Migita, K., et al., *Apoptosis Induction In Human Peripheral Blood T Lymphocytes By High-Dose Steroid Therapy*. TRANSPLANTATION 1997; 63:583-7. The plasma Cmax level achievable by systemic pulse dosing of corticosteroids is shown by line D on FIGS. 33 and 34. Significantly, the intravitreal concentration of dexamethasone (corticosteroid equivalents) obtained using the Example 16 implants (the Posurdex implants) can also be between 10-15 µg/ml. See graphs A in FIGS. 32-34. FIG. 34 illustrates that this intravitreal concentration of dexamethasone (10-15 µg/ml) can be maintained for about two weeks (see FIGS. 32-34), and as postulated by Migita, supra, can be sufficient to cause apoptosis of lymphocytes, and thereby provide a sustained anti-inflammatory effect. Besides lymphocytes, high dose pulsing of systemic corticosteroids has been shown to cause apoptosis of other inflammatory cells, including eosinophils, mast cells and B-cells. See eg. Andreau K., et al., *Induction of apoptosis by dexamethasone in the B cell lineage*, Immunopharmacology 1998 July:40(1):67-76, and; Druilhe A., et al., *Glucocorticoid-induced apoptosis in human eosinophils: mechanisms of action*, Apoptosis 2003 October; 8(5):481-95.

It is surprising and unexpected that a biodegradable (i.e. PLGA polymer matrix) intravitreal implant can be made which can release an anti-inflammatory steroid (such as dexamethasone) in a pulsatile manner and at level in intravitreal fluid sufficient to cause apoptosis of an inflammatory cell in the posterior chamber of the eye because to do so the implant must have a particular geometry to make it suitable for implantation in the vitreous (i.e. a cyclindrical shape with a diameter of about 0.5 mm and a length of from about 3 mm to about 6 mm), must contain enough dexamethasone to provide a sustained release of a therapeutic amount of the dexamethasone over a multi-month period, and must comprise a biodegradable polymer (such as a PLGA) formulated (i.e. by a double extrusion process) to provide the desired in vivo pulsatile release characteristics.

Apoptosis of inflammatory cells by intravitreal use of the biodegradable implants disclosed herein may account for the remnant effect that can be obtained (see U.S. application Ser. No. 11/292,544, filed Dec. 2, 2005 and patent application Ser. No. 10/837,357, filed Apr. 30, 2004, hereby incorporated by reference herein), as illustrated by FIG. 35. For example, in the Phase 2 Posurdex® trials there was no diminution of visual acuity with the 700 µg implant between the 3- and 6-month visits. The concentrations of dexamethasone in the retina are in the range that may affect endothelial cell and fibroblast proliferation, both relevant cell types in proliferative diabetic retinopathy.

In a preferred embodiment of the present invention the intravitreal implant can (as shown by FIGS. 26-35) provide a pulsatile release of an anti-inflammatory steroid by first providing a high dose release of an anti-inflammatory steroid (i.e. sufficient to cause apoptosis of an inflammatory cell) followed by a lower sustained dose, with all the steroid having been released from the implant in vivo over a period of no more than about 6 months to 8 months so as to reduce the incidence of adverse side effects such as elevated intraocular pressure and cataract formation. Preferably the implant releases all the steroid in vivo over a period of about 4 months to about 6 month after intravitreal implantation and most preferably over a period of about 2 months to about 4 months after intravitreal implantation of the implant.

The present invention also encompasses the use of any and all possible combinations of the therapeutic agents disclosed herein in the manufacture of a medicament, such as a drug delivery system or composition comprising such a drug delivery system, to treat one or more ocular conditions, including those identified above.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A biodegradable intraocular implant comprising:
a combination of biodegradable poly(D,L,-lactide-co-glycolide) and poly(D,L,-lactide) polymers in a 1:2 ratio, respectively, and an alpha-2 adrenergic receptor agonist and a steroid in a 60:40 weight ratio of drug to polymer, wherein the alpha-2 adrenergic agonist and steroid are arranged in interleaved alternate layers;
wherein the alpha-2 adrenergic receptor agonist is selected from the group consisting of apraclonidine, clonidine, oxymetazoline, epinephrine, norepinephrine, dexmedetomidine, mivazerol, xylazine, medetomidine, and brimonidine; and
wherein the steroid is selected from the group consisting of cortisone, prednisolone, fluorometholone, dexamethasone, medrysone, loteprednol, fluazacort, hydrocortisone, betamethasone, prednisone, methylprednisolone, triamcinolone hexacatonide, paramethasone acetate, triamcinolone acetonide, diflorasone, fluocinonide, and mixtures thereof.

2. The intraocular implant of claim 1, wherein the alpha-2 adrenergic receptor agonist is brimonidine and the steroid is dexamethasone.

* * * * *

UNITED STATES PATENT AND TRADEMARK OFFICE
CERTIFICATE OF CORRECTION

PATENT NO.       : 8,802,128 B2
APPLICATION NO.  : 11/491353
DATED            : August 12, 2014
INVENTOR(S)      : Michael R. Robinson et al.

It is certified that error appears in the above-identified patent and that said Letters Patent is hereby corrected as shown below:

On the Title Page

On the Page 3, in column 1, Item (56), under "Other Publications", line 9, delete "Substained" and insert -- Sustained --, therefor.

On the Page 3, in column 1, Item (56), under "Other Publications", line 58, delete "Aminopeptidease" and insert -- Aminopeptidase --, therefor.

On the Page 4, in column 1, Item (56), under "Other Publications", line 30, delete "Polyactic" and insert -- Polylactic --, therefor.

On the Page 4, in column 1, Item (56), under "Other Publications", line 30, delete "Biogradable" and insert -- Biodegradable --, therefor.

On the Page 4, in column 2, Item (56), under "Other Publications", line 4, delete "Biogradable" and insert -- Biodegradable --, therefor.

On the Page 4, in column 2, Item (56), under "Other Publications", line 10, delete "Acetysalicyclic" and insert -- Acetylsalicylic --, therefor.

On the Page 5, in column 2, Item (56), under "Other Publications", line 66, delete "Introcular" and insert -- Intraocular --, therefor.

In the Specification

In column 7, line 4, delete "dexamethasonedexamethasone" and insert -- dexamethasone --, therefor.

In column 7, line 14, delete "microcystaline" and insert -- microcrystalline --, therefor.

In column 7, line 15, delete "Retiserte" and insert -- Retisert® --, therefor.

In column 9, line 59, delete "opthalmia;" and insert -- ophthalmia; --, therefor.

In column 10, line 29, delete "and or" and insert -- and/or --, therefor.

In column 10, line 48, delete "diproprionate." and insert -- dipropionate. --, therefor.

Signed and Sealed this
Seventh Day of April, 2015

Michelle K. Lee
*Director of the United States Patent and Trademark Office*

CERTIFICATE OF CORRECTION (continued)
U.S. Pat. No. 8,802,128 B2

In column 10, line 51-52, delete "beclamethasone diproprionate." and insert -- beclomethasone dipropionate. --, therefor.

In column 14, line 38, delete "acteonide" and insert -- acetonide --, therefor.

In column 15, line 33, delete "and or" and insert -- and/or --, therefor.

In column 16, line 7, delete "pentantoate" and insert -- pentanoate --, therefor.

In column 16, line 14, delete "poly(butylnethacrylate)," and insert -- poly(butylmethacrylate), --, therefor.

In column 20, line 38, delete "bioerodable" and insert -- bioerodible --, therefor.

In column 21, line 37, delete "loradatine," and insert -- loratadine, --, therefor.

In column 21, line 41-42, delete "trimprazine" and insert -- trimeprazine --, therefor.

In column 21, line 42, delete "chiorcyclizine," and insert -- chlorcyclizine, --, therefor.

In column 21, line 46, delete "cefutoxime," and insert -- cefuroxime, --, therefor.

In column 21, line 63, delete "flurometholone," and insert -- fluorometholone, --, therefor.

In column 21, line 65-66, delete "riamcinolone hexacatonide," and insert -- triamcinolone hexacetonide, --, therefor.

In column 22, line 2, delete "duanorubicin," and insert -- daunorubicin, --, therefor.

In column 22, line 14, delete "valciclovir," and insert -- valacyclovir, --, therefor.

In column 22, line 19, delete "cryotpxanthin, astazanthin," and insert -- cryptoxanthin, astaxanthin, --, therefor.

In column 22, line 21, delete "quercitin," and insert -- quercetin, --, therefor.

In column 24, line 11, delete "serpignous" and insert -- serpiginous --, therefor.

In column 24, line 17, delete "telangiectasis," and insert -- telangiectasia, --, therefor.

In column 24, line 20, delete "angitis," and insert -- angiitis, --, therefor.

In column 24, line 42, delete "Biefti's" and insert -- Bietti's --, therefor.

In column 24, line 63, delete "subconjuctival" and insert -- subconjunctival --, therefor.

In column 25, line 2-3, delete "subconjuctival" and insert -- subconjunctival --, therefor.

In column 26, line 50-51, delete "cholinomimetrics," and insert -- cholinomimetics, --, therefor.

In column 26, line 54, delete "pilocarpone," and insert -- pilocarpine, --, therefor.

In column 26, line 67, delete "sympathomimetrics" and insert -- sympathomimetics --, therefor.

In column 27, line 4, delete "oufflow." and insert -- outflow. --, therefor.

In column 27, line 6, delete "dexmedatomidine," and insert -- dexmedetomidine, --, therefor.

In column 27, line 66, delete "adrenoreceptor" and insert -- adrenoceptor --, therefor.

In column 27, line 67, delete "adrenoreceptor" and insert -- adrenoceptor --, therefor.

In column 28, line 62, delete "PGF2$_\alpha$" and insert -- PGF2α --, therefor.

In column 29, line 3, delete "uveoscieral" and insert -- uveoscleral --, therefor.

CERTIFICATE OF CORRECTION (continued)
U.S. Pat. No. 8,802,128 B2

In column 29, line 22, delete "PGF2$_\alpha$," and insert -- PGF2α --, therefor.

In column 30, line 35, delete "oufflow." and insert -- outflow. --, therefor.

In column 30, line 39, delete "oufflow" and insert -- outflow --, therefor.

In column 30, line 60, delete "beclamethasone diproprionate," and insert -- beclomethasone dipropionate, --, therefor.

In column 31, line 6, delete "pilocarpone," and insert -- pilocarpine, --, therefor.

In column 31, line 7, delete "apracionidine," and insert -- apraclonidine, --, therefor.

In column 31, line 8, delete "metipranilol," and insert -- metipranolol, --, therefor.

In column 31, line 8-9, delete "dorzolamine," and insert -- dorzolamide, --, therefor.

In column 31, line 12, delete "dexmedatomidine," and insert -- dexmedetomidine, --, therefor.

In column 33, line 6, delete "of," and insert -- off, --, therefor.

In column 34, line 29, delete "Flucinolone" and insert -- Fluocinolone --, therefor.

In column 36, line 62, delete "were." and insert -- were --, therefor.

In column 40, line 34, delete "three fold" and insert -- threefold --, therefor.

In column 43, line 57, delete "cetytrimethylammonium" and insert -- cetyltrimethylammonium --, therefor.

In column 44, line 12, delete "Beclamethasone" and insert -- Beclomethasone --, therefor.

In column 44, line 14, delete" Boehringer-Ingelheim" and insert -- Boehringer Ingelheim --, therefor.

In column 44, line 52-53, delete "Beclamethasone" and insert -- Beclomethasone --, therefor.

In column 45, line 38, delete "48" and insert -- 48, --, therefor.

In column 51, line 23-24, delete "fluocinololone" and insert -- fluocinolone --, therefor.

In column 51, line 30, delete "fluocinololone" and insert -- fluocinolone --, therefor.

In column 51, line 62, delete "flucinololone" and insert -- fluocinolone --, therefor.

In column 51, line 64, delete "flucinololone" and insert -- fluocinolone --, therefor.

In column 52, line 16, delete "Uveitits" and insert -- Uveitis --, therefor.

In column 52, line 20, delete "(irititis)," and insert -- (iritis), --, therefor.

In column 54, line 61, delete "of." and insert -- of --, therefor.

In column 55, line 30, delete "PHARMALOGICAL" and insert -- PHARMACOLOGICAL --, therefor.

In column 56, line 36, delete "cyclindrical" and insert -- cylindrical --, therefor.

In the Claims

In column 57, line 18, in claim 1, delete "poly(D,L,-lactide" and insert -- poly(D,L-lactide --, therefor.

In column 57, line 19, in claim 1, delete "poly(D,L,-lactide" and insert -- poly(D,L-lactide --, therefor.

In column 58, line 14, in claim 1, delete "hexacatonide," and insert -- hexacetonide, --, therefor.